(12) United States Patent
Vleugels

(10) Patent No.: US 11,367,517 B2
(45) Date of Patent: *Jun. 21, 2022

(54) GESTURE-BASED DETECTION OF A PHYSICAL BEHAVIOR EVENT BASED ON GESTURE SENSOR DATA AND SUPPLEMENTAL INFORMATION FROM AT LEAST ONE EXTERNAL SOURCE

(71) Applicant: MEDTRONIC MINIMED, INC., Northridge, CA (US)

(72) Inventor: Katelijn Vleugels, San Carlos, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 71 days.

This patent is subject to a terminal disclaimer.

(21) Appl. No.: 16/886,353

(22) Filed: May 28, 2020

(65) Prior Publication Data
US 2020/0294645 A1 Sep. 17, 2020

Related U.S. Application Data

(63) Continuation-in-part of application No. 16/667,641, filed on Oct. 29, 2019, and a continuation-in-part of application No. 16/667,650, filed on Oct. 29, 2019.
(Continued)

(51) Int. Cl.
*G16H 20/13* (2018.01)
*G06F 3/01* (2006.01)
(Continued)

(52) U.S. Cl.
CPC ......... *G16H 20/13* (2018.01); *A61B 5/14532* (2013.01); *G06F 3/017* (2013.01); *G06N 7/005* (2013.01); *G06V 40/20* (2022.01)

(58) Field of Classification Search
CPC .................. G16H 20/13; G06F 3/017
See application file for complete search history.

(56) References Cited

U.S. PATENT DOCUMENTS

| 4,755,173 A | 7/1988 | Konopka et al. |
| 5,391,250 A | 2/1995 | Cheney, II et al. |
| (Continued) | | |

OTHER PUBLICATIONS

Oliver Amft, et al., On-Body Sensing Solutions for Automatic Dietary Monitoring, Wearable Computing and Healthcare, 2009, Pervasive Computing, Published by IEEE CS, pp. 62-70.
(Continued)

*Primary Examiner* — David E Choi
(74) *Attorney, Agent, or Firm* — Carter, DeLuca & Farrell LLP

(57) ABSTRACT

An automated medication dosing and dispensing system includes: gesture sensors to detect physical movement of a user; computer-readable storage media with program code instructions; and at least one processor. The instructions are configurable to cause the at least one processor to perform a method that involves: detecting, based on analysis of gesture sensor readings obtained from the gesture sensors, an occurrence of a gesture-based physical behavior event; calculating an initial confidence level for the detected occurrence of the gesture-based physical behavior event; deriving a final confidence level, for the detected occurrence of the gesture-based physical behavior event, from the initial confidence level and from external information obtained from at least one source of data that is distinct from the gesture sensors; and adjusting medication dosage and/or medication dispensing parameters in response to the detected occurrence of the gesture-based physical behavior event and the final confidence level.

20 Claims, 32 Drawing Sheets

Related U.S. Application Data

(60) Provisional application No. 62/932,370, filed on Nov. 7, 2019, provisional application No. 62/753,819, filed on Oct. 31, 2018.

(51) Int. Cl.
*G06N 7/00* (2006.01)
*A61B 5/145* (2006.01)
*G06V 40/20* (2022.01)

(56) References Cited

U.S. PATENT DOCUMENTS

| | | |
|---|---|---|
| 5,485,408 A | 1/1996 | Blomquist |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Van Antwerp et al. |
| 6,017,328 A | 1/2000 | Fischell et al. |
| 6,186,982 B1 | 2/2001 | Gross et al. |
| 6,246,992 B1 | 6/2001 | Brown |
| 6,248,067 B1 | 6/2001 | Causey, III et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,591,876 B2 | 7/2003 | Safabash |
| 6,641,533 B2 | 11/2003 | Causey, III et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian, Jr. et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode, Jr. et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Mair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 8,391,104 B2 * | 3/2013 | de la Huerga ... G06K 19/07762 368/10 |
| 10,790,054 B1 * | 9/2020 | Vleugels ................ G16H 20/60 |
| 2007/0123819 A1 | 5/2007 | Mernoe et al. |
| 2010/0160861 A1 | 6/2010 | Causey, III et al. |
| 2011/0022224 A1 * | 1/2011 | Park ..................... A61J 7/0409 700/232 |
| 2014/0349257 A1 | 11/2014 | Connor |
| 2015/0199484 A1 | 7/2015 | Morris et al. |
| 2016/0030683 A1 * | 2/2016 | Taylor ..................... A61M 5/32 604/151 |
| 2016/0232811 A9 | 8/2016 | Connor |
| 2017/0213014 A1 | 7/2017 | Su |
| 2017/0220751 A1 * | 8/2017 | Davis ................ A61B 5/14503 |
| 2017/0220772 A1 * | 8/2017 | Vleugels ................ A61B 5/16 |
| 2018/0169334 A1 | 6/2018 | Grosman et al. |
| 2018/0353698 A1 | 12/2018 | Saint et al. |
| 2019/0015596 A1 * | 1/2019 | Saint ................... A61M 5/3202 |
| 2020/0118665 A1 * | 4/2020 | Bender ................. G06N 7/005 |
| 2020/0357503 A1 * | 11/2020 | Sugaya ................ A61B 5/6887 |

OTHER PUBLICATIONS

Tri Vu, et al., Wearable Food Intake Monitoring Technologies: A Comprehensive Review, MDPI Journal, Sep. 23, 2016, pp. 1-28.

* cited by examiner

GESTURE-BASED DETECTION OF A PHYSICAL BEHAVIOR EVENT BASED ON GESTURE SENSOR DATA AND SUPPLEMENTAL INFORMATION FROM AT LEAST ONE EXTERNAL SOURCE

CROSS-REFERENCE TO RELATED APPLICATIONS

This application is a continuation-in-part of U.S. patent application Ser. No. 16/667,641, filed Oct. 29, 2019, which claims the benefit of U.S. provisional patent application No. 62/753,819, filed Oct. 31, 2018. This application is also a continuation-in-part of U.S. patent application Ser. No. 16/667,650, filed Oct. 29, 2019, which claims the benefit of U.S. provisional patent application No. 62/753,819, filed Oct. 31, 2018. This application also claims the benefit of U.S. provisional patent application No. 62/932,370, filed Nov. 7, 2019.

TECHNICAL FIELD

This disclosure relates generally to medication dispensing or management and more particularly to methods and apparatus for using sensors for tracking patient activity and deriving patient activity related to food intake for use in providing reminders to the patient or a caregiver about medication needs and/or signaling to a medication dispensing device to dispense a medication.

BACKGROUND

For some medical conditions, such as Type 1 diabetes, the scheduling and dosing of medication such as insulin depends on various factors such as the patient's current blood sugar levels and whether the patient is eating or drinking, and the contents of what is being consumed. Thus, knowing when someone has started, or is about to start, eating or drinking is relevant in the treatment of individuals with diabetes who are on an insulin regimen. Other parameters that further quantify the eating or drinking activities, such as the duration or pace of eating or drinking can also be relevant as the medication regimen might vary based on duration and/or pace.

Millions of people have Type 1 diabetes, a condition wherein a person's body does not produce insulin. The human body breaks down consumed carbohydrates into blood glucose, which the body uses for energy. The body needs to convert that blood glucose from the bloodstream into glucose the cells of the body and does this using the hormone insulin. A person with Type 1 diabetes does not generate their own insulin in sufficient quantities to regulate blood sugar and may require insulin injections to maintain safe blood sugar levels.

Insulin can be provided by a micrometering system that injects a specific amount of insulin over time. For example, a Type 1 diabetes patient might need to regularly check their blood sugar levels and manually inject the correct dosage of insulin needed at the start of a meal so that their body is able to convert the glucose that is put into their bloodstream as a result of a meal into glucose stored into body cells. Both overdosing and underdosing can lead to adverse conditions and long-term complications. Manual management of a microdosing system or injecting insulin are treatment regimens and often require timing and dosing that can vary. This can make managing the disease difficult, especially where the patient is a younger child.

One approach is a "hybrid" closed-loop dosing system that makes continuous, or periodic near-continuous, blood glucose readings and microdoses the patient autonomously based on those readings, except when the patient eats or drinks. To deal with the latter, the hybrid system accepts patient input signaling when the patient is going to start eating or drinking. Without this added information, the dosing system would be too slow to respond, as there are considerable delays in glucose readings and insulin diffusion. Manual meal announcements introduce a significant burden on the patient and poor compliance results in degraded glycemic control. Missed pre-meal insulin boluses are a significant contributor to poor glycemic control in Type 1 diabetes patients.

Improved methods and apparatus for automated eating or drinking event detection and signaling a dosing system and/or reminder messaging to patients, caregivers, and health professionals are needed.

BRIEF SUMMARY

An automated medication dispensing system might comprise sensors to detect movement and other physical inputs related to a user of the automated medication dispensing system, a processor for executing program code and for processing data received from the sensors, including a set of sensor readings wherein at least one sensor reading of the set of sensor readings measures a movement of a body part of the user, an event detection module for determining, from the set of sensor readings, gestures of the user, storage for event-specific parameters, initialized for a food intake event, and storage for an event state value, wherein the event state value is one of an out-of-event state or an in-event state, with the event state value initialized to the out-of-event state. The program code might comprise: a) program code for determining, from the set of sensor readings, a first potential gesture of the user including a gesture type of the first potential gesture, wherein some of the gesture types are members of a first set of gesture types, b) program code for determining a confidence level related to the first potential gesture, wherein the confidence level relates to a level of confidence that the gesture type of the first potential gesture was correctly determined, c) program code for modifying and recording, wherein if the confidence level is above or at a threshold and the gesture type is a member of the first set of gesture types, modifying the event state value from the out-of-event state to the in-event state and recording the first potential gesture as a first gesture of the food intake event, d) program code for determining, from the confidence level and/or the event state value, an inferred event for which a medication administration message is to be sent, and e) program code for outputting the medication administration message to the user as to a medication administration need.

The automated medication dispensing system might output a secondary message to additional destinations beyond the user as to the medication administration need. The additional destinations might comprise communication devices of a friend of the user, a health care provider of the user, and/or a first responder. The automated medication dispensing system might update a medication log and/or inventory in response to the inferred event, signal to an input of an insulin management system, and/or signal to an input of a meal-aware artificial pancreas.

In some embodiments, an event detection system includes sensors to detect movement and other physical inputs related to a user, which the event detection system can process to identify gestures of the user, a method of further processing comprising:

providing storage for event-specific parameters, initialized for a food intake event;

providing storage for an event state value, wherein the event state value is one of an out-of-event state or an in-event state, with the event state value initialized to the out-of-event state;

determining, using a processor in the event detection system, a set of sensor readings, wherein at least one sensor reading of the set of sensor readings measures a movement of a body part of the user;

determining, from the set of sensor readings, a first potential gesture of the user including a gesture type of the first potential gesture, wherein some of the gesture types are members of a first set of gesture types;

determining a confidence level related to the first potential gesture, wherein the confidence level relates to a level of confidence that the gesture type of the first potential gesture was correctly determined;

if the confidence level is above or at a threshold and the gesture type is a member of the first set of gesture types:

(a) modifying the event state value from the out-of-event state to the in-event state; and (b) recording the first potential gesture as a first gesture of the food intake event; and outputting a message to a patient as to a medication administration need.

The method might further comprise providing storage for additional event-specific parameters, including a drinking event, a smoking event, a personal hygiene event, and/or a medication related event. An external trigger time might be determined from when the food intake event is inferred to have started, when the food intake event is inferred to be ongoing, and/or when the food intake event is inferred to have concluded. A computer-based action in response to the food intake event might be one or more of (a) obtaining other information to be stored in memory in association with data representing the food intake event, (2) interacting with the user to provide information or a reminder, (3) interacting with the user to prompt for user input, (4) sending a message to a remote computer system, and/or (5) sending a message to another person.

The method might comprise recording the food intake event in a food log, and/or updating an inventory database in response to the food intake event.

A system for sensing wearer activity might comprise:

at least one sensor of an electronic device worn by a wearer for sensing the wearer activity or portions thereof including a movement of a body part of the wearer;

storage for event-specific parameters, initialized for a food intake event;

storage, within the electronic device, for an event state value, wherein the event state value is one of an out-of-event state or an in-event state, with the event state value initialized to the out-of-event state;

a processor in the electronic device that determines a set of sensor readings from the at least one sensor; and program code, stored in the electronic device or in a component of the system in communication with the electronic device, executable by the processor in the electronic device or another processor, comprising:

a) program code for determining, from the set of sensor readings, a first potential gesture of the wearer including a gesture type of the first potential gesture, wherein some of the gesture types are members of a first set of gesture types;

b) program code for determining a confidence level related to the first potential gesture, wherein the confidence level relates to a level of confidence that the gesture type of the first potential gesture was correctly determined;

c) program code for determining if the confidence level is above or at a threshold and the gesture type is a member of the first set of gesture types and when the confidence level is above or at the threshold and the gesture type is a member of the first set of gesture types, modifying the event state value from the out-of-event state to the in-event state and recording the first potential gesture as a first gesture of the food intake event;

d) program code for determining, from a set of additional sensor readings, additional gestures of the wearer, each having a respective gesture type;

e) program code for determining if the event state value is the in-event state and when the event state value is the in-event state, recording the first gesture and the additional gestures as a gesture sequence of the food intake event and deriving the event-specific parameters from at least some gestures of the gesture sequence; and f) outputting a message to a patient as to a medication administration need.

The system might comprise controls for changing the electronic device to a higher performance state when the event state value is modified from the out-of-event state to the in-event state, wherein the higher performance state comprises one or more of additional power supplied to sensors, a reduced latency of a communications channel, and/or an increased sensor sampling rate. A sensor might comprise one or more accelerometers that measures movement of an arm of the wearer and a gyroscope that measures rotation of the arm of the wearer.

Using gesture sensing technology, an event detection system can trigger and external device to gather further information. In a specific embodiment, the external device is a near-field communication (NFC) reader and various objects having NFC tags thereon are detected. Where those objects are food/beverage related, the event detection system can determine what the gestures are related to. For example, food/beverage containers might have NFC tags embedded in the product packaging and a food intake monitoring system might automatically determine that gestures are related to an eating event, then signal to an NFC reader to turn on and read nearby NFC tags, thereby reading the NFC tags on the products being consumed so that the gestures and the event are associated with a specific product.

In other variations, other wireless technology can be used. In some variations, the external device is a module integrated within a housing that also houses the event detection system.

An event detection system might include sensors to detect movement and other physical inputs related to a user, which the event detection system can process to identify gestures of the user, and possibly also determine, using historical data, machine learning, rule sets, or other techniques for processing data to derive an inferred event related to the user sensed by the sensors. For example, sensors might detect audio signals near the mouth of the user, which the event detection system can use in inferring an event, such as an event related to a user's eating or drinking activities. Other non-hand sensors might also be used, such as motion sensors, temperature sensors, audio sensors, etc.

Example gestures might be a food intake gesture, a sip gesture, or some other gesture. An inferred event might be an eating event, a smoking event, a personal hygiene event, a medication related event, or some other event the user is inferred to be engaging in. A gesture might represent some movement of the user, such as hand gestures that can be detected using a wrist-worn device so as to be non-intrusive or minimally intrusive and that can operate with no or minimal user intervention.

When an event is inferred to have started, to be ongoing, and/or to have concluded, the event detection system can take actions related to that event, such as obtaining other information to be stored in memory in association with the data representing the event, interacting with the user to provide information or reminders or to prompt for user input, sending a message to a remote computer system, sending a message to another person, such as a friend, health care provider, first responder, or other action(s). In a specific example, once the event detection system infers that an event has started, it signals to an ancillary sensor system or an ancillary processing system to take an action such as gathering more information, sending communication or a processing task. The event detection system might create a data record for an event once a new event is detected and populate that data record with details of the event that the event detection system is able to determine, such as details about gestures that are involved in that event. The ancillary sensor system or ancillary processing system might populate that data record with ancillary data about the event, such as the ancillary data described herein.

The event detection system and ancillary sensor system and/or ancillary processing system can be used as part of a monitoring system with one or more applications, such as food logging, inventory tracking/replenishment, production line monitoring/QC automation, medication adherence, insulin therapy, supporting a meal-aware artificial pancreas, and other applications.

A sensing device monitors and tracks food intake events and details. A processor, appropriately programmed, controls aspects of the sensing device to capture data, store data, analyze data and provide suitable feedback related to food intake. More generally, the methods might include detecting, identifying, analyzing, quantifying, tracking, processing and/or influencing, related to the intake of food, eating habits, eating patterns, and/or triggers for food intake events, eating habits, or eating patterns. Feedback might be targeted for influencing the intake of food, eating habits, or eating patterns, and/or triggers for those. Feedback might also be targeted to remind the user to take one or more actions. The sensing device can also be used to track and provide feedback beyond food-related behaviors and more generally track behavior events, detect behavior event triggers and behavior event patterns and provide suitable feedback. The event detection system might be implemented with hardware and/or software.

An automated medication dosing and dispensing system includes: sensors to detect physical movement of a user of the automated medication dosing and dispensing system; computer-readable storage media comprising program code instructions; and at least one processor, wherein the program code instructions are configurable to cause the at least one device to perform a method. The method involves the steps of: detecting, based on analysis of sensor readings obtained from the sensors, occurrences of gesture-based physical behavior events; storing historical event information corresponding to the detected occurrences of gesture-based physical behavior events; processing the stored historical event information to predict a future occurrence of a physical behavior event of interest; and adjusting medication dosage, medication dispensing parameters, or both medication dosage and medication dispensing parameters in response to the predicted future occurrence of the physical behavior event of interest.

Also disclosed here is a method of operating an automated medication dosing and dispensing system having sensors that detect movement of a user. An embodiment of the method involves the steps of: obtaining sensor readings from the sensors; detecting, based on analysis of the obtained sensor readings, occurrences of gesture-based physical behavior events; storing historical event information corresponding to the detected occurrences of gesture-based physical behavior events; processing, with at least one processor of the automated medication dosing and dispensing system, the stored historical event information to predict a future occurrence of a physical behavior event of interest; and adjusting medication dosage, medication dispensing parameters, or both medication dosage and medication dispensing parameters in response to the predicted future occurrence of the physical behavior event of interest.

Also disclosed here is a method of operating an automated medication dosing and dispensing system having sensors that detect movement. An embodiment of the method involves the steps of: obtaining sensor readings from the sensors, the sensor readings indicating movement of at least one body part of the user; detecting, based on analysis of the obtained sensor readings, occurrences of gesture-based physical behavior events; storing historical event information corresponding to the detected occurrences of gesture-based physical behavior events; receiving at least one ancillary input from a detection system that is distinct from the sensors; processing, with at least one processor of the automated medication dosing and dispensing system, the stored historical event information and the at least one ancillary input to predict a future occurrence of a physical behavior event of interest; and adjusting medication dosage, medication dispensing parameters, or both medication dosage and medication dispensing parameters in response to the predicted future occurrence of the physical behavior event of interest.

An automated medication dosing and dispensing system includes: gesture sensors to detect physical movement of a user of the automated medication dosing and dispensing system; computer-readable storage media comprising program code instructions; and at least one processor, wherein the program code instructions are configurable to cause the at least one processor to perform a method. An embodiment of the method involves the steps of: detecting, based on analysis of gesture sensor readings obtained from the gesture sensors, an occurrence of a gesture-based physical behavior event; calculating an initial confidence level for the detected occurrence of the gesture-based physical behavior event; deriving a final confidence level, for the detected occurrence of the gesture-based physical behavior event, from the initial confidence level and from external information obtained from at least one source of data that is distinct from the gesture sensors; and adjusting medication dosage, medication dispensing parameters, or both medication dosage and medication dispensing parameters in response to the detected occurrence of the gesture-based physical behavior event and the final confidence level.

Also disclosed here is a method of operating an automated medication dosing and dispensing system having gesture sensors that detect physical movement of a user. An embodiment of the method involves the steps of: obtaining gesture sensor readings from the gesture sensors; detecting, based on analysis of the obtained gesture sensor readings, an occurrence of a gesture-based physical behavior event;

calculating an initial confidence level for the detected occurrence of the gesture-based physical behavior event; deriving a final confidence level, for the detected occurrence of the gesture-based physical behavior event, from the initial confidence level and external information obtained from at least one source of data that is distinct from the gesture sensors; and adjusting medication dosage, medication dispensing parameters, or both medication dosage and medication dispensing parameters in response to the detected occurrence of the gesture-based physical behavior event and the final confidence level.

An automated medication dosing and dispensing system includes: gesture sensors to detect physical movement of a user of the automated medication dosing and dispensing system; computer-readable storage media comprising program code instructions; and at least one processor, wherein the program code instructions are configurable to cause the at least one processor to perform a method. An embodiment of the method involves the steps of: maintaining default event declaration criteria for use in determining whether a gesture-based physical behavior event of interest has occurred or is likely to occur; obtaining gesture sensor readings from the gesture sensors; deriving final event declaration criteria, for use in determining whether the gesture-based physical behavior event of interest has occurred or is likely to occur, from the default event declaration criteria and from external information obtained from at least one source of data that is distinct from the gesture sensors; and analyzing the obtained gesture sensor readings to determine whether the final event declaration criteria is satisfied. When the obtained gesture sensor readings satisfy the final event declaration criteria, the method declares a detection of the gesture-based physical behavior event of interest, and adjusts medication dosage, medication dispensing parameters, or both medication dosage and medication dispensing parameters in response to the declaring.

Also disclosed here is a method of operating an automated medication dosing and dispensing system having gesture sensors that detect physical movement of a user. An embodiment of the method involves the steps of: maintaining default event declaration criteria for use in determining whether a gesture-based physical behavior event of interest has occurred or is likely to occur; obtaining gesture sensor readings from the gesture sensors; deriving final event declaration criteria, for use in determining whether the gesture-based physical behavior event of interest has occurred or is likely to occur, from the default event declaration criteria and from external information obtained from at least one source of data that is distinct from the gesture sensors; and analyzing the obtained gesture sensor readings to determine whether the final event declaration criteria is satisfied. When the obtained gesture sensor readings satisfy the final event declaration criteria, the method declares a detection of the gesture-based physical behavior event of interest, and adjusts medication dosage, medication dispensing parameters, or both medication dosage and medication dispensing parameters in response to the declaring.

An automated medication dosing and dispensing system includes: gesture sensors to detect physical movement of a user of the automated medication dosing and dispensing system; a measurement sensor to generate sensor data indicative of a physiological characteristic of the user; a measurement sensor processor to process the sensor data generated by the measurement sensor; computer-readable storage media comprising program code instructions; and at least one processor, wherein the program code instructions are configurable to cause the at least one processor to perform a method. An embodiment of the method involves the steps of: detecting, based on analysis of gesture sensor readings obtained from the gesture sensors, an occurrence of a gesture-based physical behavior event; providing, to at least one of the measurement sensor and the measurement sensor processor, event information corresponding to the detected occurrence of the gesture-based physical behavior event; and adjusting an operating parameter of the at least one of the measurement sensor and the measurement sensor processor, in accordance with the provided event information.

Also disclosed here is a method of operating an automated medication dosing and dispensing system comprising gesture sensors to detect physical movement of a user, a measurement sensor to generate sensor data indicative of a physiological characteristic of the user, and a measurement sensor processor to process the sensor data. An embodiment of the method involves the steps of: obtaining gesture sensor readings from the gesture sensors; detecting, based on analysis of the obtained gesture sensor readings, an occurrence of a gesture-based physical behavior event; and providing, to at least one of the measurement sensor and the measurement sensor processor, event information corresponding to the detected occurrence of the gesture-based physical behavior event. The event information is formatted to control adjustment of an operating parameter of the at least one of the measurement sensor and the measurement sensor processor, in accordance with the provided event information.

Also disclosed here is a method of operating an automated medication dosing and dispensing system comprising gesture sensors to detect physical movement of a user, a measurement sensor to generate sensor data indicative of a physiological characteristic of the user, and a measurement sensor processor to process the sensor data. An embodiment of the method involves the steps of: obtaining gesture sensor readings from the gesture sensors; detecting, based on analysis of the obtained gesture sensor readings, an occurrence of a gesture-based physical behavior event; providing, to at least one of the measurement sensor and the measurement sensor processor, event information corresponding to the detected occurrence of the gesture-based physical behavior event; and adjusting one or more operating parameters of at least one of the measurement sensor and the measurement sensor processor, in accordance with the provided event information.

The following detailed description together with the accompanying drawings will provide a better understanding of the nature and advantages of the present invention.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

Various embodiments in accordance with the present disclosure will be described with reference to the drawings, in which.

DETAILED DESCRIPTION

Figure 1:
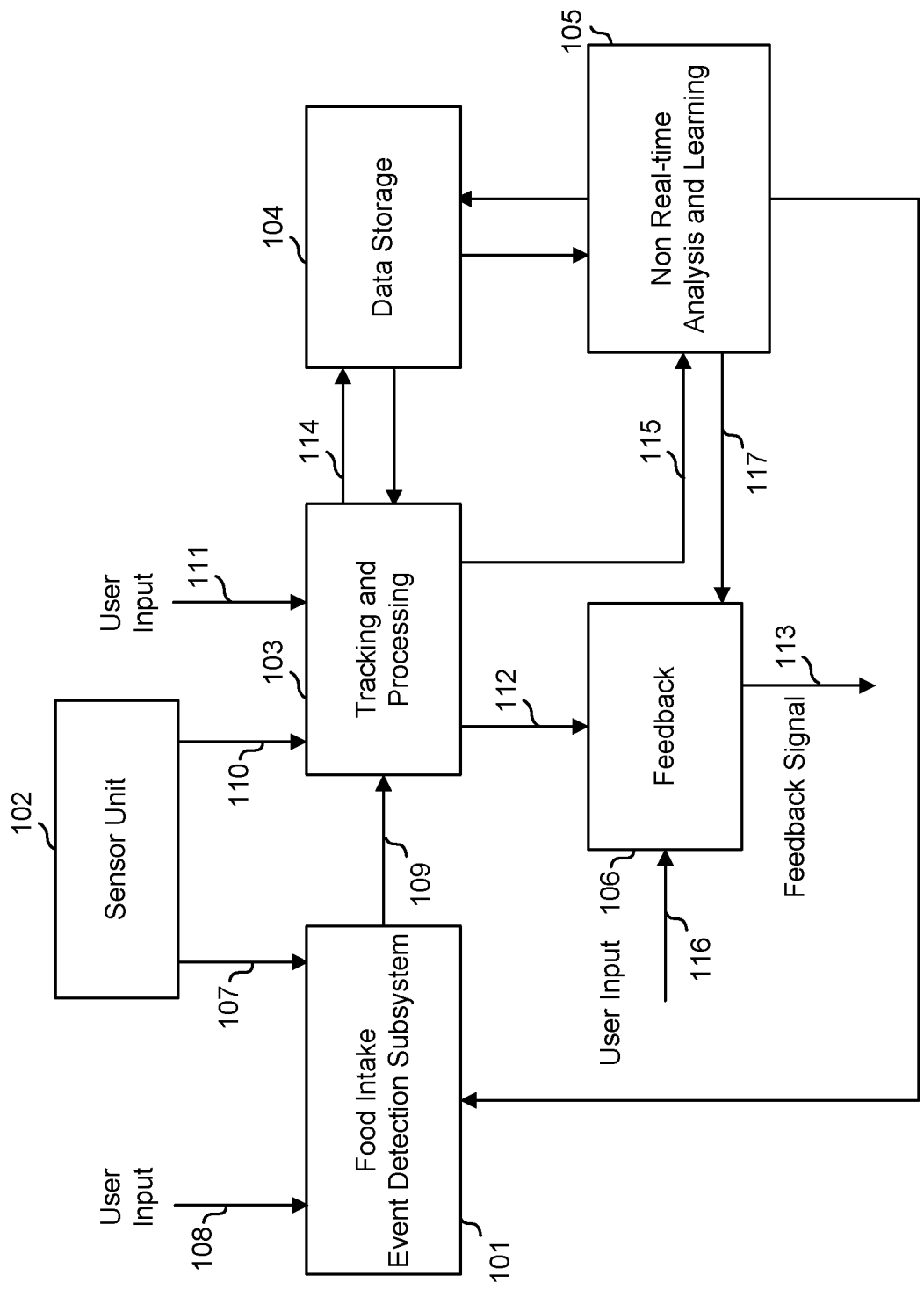
FIG. 1 illustrates an event monitoring system.

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

Various examples are provided herein of devices that a person would use to monitor, track, analyze and provide feedback on food intake, the intake process and timing and other relevant aspects of a person's eating, drinking and other consumption for various ends, such as providing diet information and feedback. The data related to food intake process might include, timing of the eating process, pace of eating, time since last food intake event, what is eaten, estimates of the contents of what is eaten, etc. Such devices can be integrated with a medication dosing system.

Overview

As will be described in greater detail herein, a patient management system comprising a novel digital health app and a wearable sensing apparatus that interacts with the app can provide for a fully autonomous artificial pancreas system and that can dramatically improve quality of life for people with Type 1 diabetes. This patient management system can remind patients to take or administer their medication but can also provide for hybrid or autonomous management of medication dosing, such as for example insulin dosing. This patient management system can promote mindful eating and proper hydration.

Through a combination of fine motor detection and artificial intelligence technology, the patient management system detects high impact moments and allows individuals to better manage their health, all based on insights that are captured automatically and non-intrusively from analyzing their wrist movements and other sensor inputs. Response actions might include sending bolus reminders to patients and/or their caregivers. Early meal detection capabilities can provide unique insights into eating behaviors are critical components towards the realization of an autonomous artificial pancreas system.

The patient management system might have an open data and software architecture. This might allow for other companies, researchers and developers to make use of the patient management system and the data it generates, perhaps via an API that allows for seamless integration with third-party applications and platforms.

In a specific use, the patient management system serves as a mealtime medication reminder that messages the patient as to the need to initiate an insulin dose. The patient management system might have a multi-level messaging capability. For example, where the patient is messaged about the need to take an action, and the patient does not respond, the patient management system might send a message to a caregiver to indicate that the patient did or did not take the expected action in response to the detection of the start of an eating event or did not take action for a mealtime insulin administration. A fully autonomous closed-loop artificial pancreas system, can be in part enabled by the patient management system and its ability to provide automated real-time or near real-time information of a patient's eating behavior, coupled with novel control processes, thus potentially enabling a true "set and forget" closed-loop insulin delivery system.

The patient management system might be useful for a person concerned about their diet for other reasons. People with Type 1 diabetes are usually on an insulin therapy where, based on their food intake and other factors, they administer the proper insulin dosage. While the cause of Type 1 diabetes may not be directly linked to a person's eating behavior, a person with Type 1 diabetes needs to carefully track his or her food intake in order to manage his or her insulin therapy. Such patients will also benefit from easier to use and more discreet methods for food intake tracking. In some embodiments of the patient management system, the sensing device is part of a feedback-driven automated insulin delivery therapy system. Such a system might include continuous monitoring of a patient's glucose levels, a precision insulin delivery system, and the use of insulin that has a faster absorption rate, that would further benefit from information that can be extracted from automated and seamless food intake tracking, such as the tracking of carbohydrates and sugar intake. The devices might also be useful for wellness programs and the like.

Data Collection

Data can be obtained from some stationary device having sensors and electronics, some mobile device having sensors and electronics that is easily moved and carried around by a person, and/or from wearable devices having sensors and electronics that a person attaches to their person or clothing, or is part of the person's clothing. In general, herein such devices are referred to as sensing devices. The data might be raw sensor data provided by the sensors capable of outputting data, or the data might be processed, sampled, or organized in some way so as to be data derived from the outputs of sensors.

Herein, the person having such a device and who's consumption is being monitored is referred to as the user but it should be understood that the device might be used unchanged in situations where the person consuming, the person monitoring, and the person evaluating feedback need not all be the same person. Herein, what is consumed is referred to as food intake, but it should be clear that these devices can be used to more generally track consumption and consumption patterns. A behavior tracking/feedback system as described herein might comprise one or more wearable devices and might also comprise one or more additional devices that are not worn. These additional devices might be carried by the wearer or kept nearby so that they can communicate with the wearable devices. The behavior tracking/feedback system might also comprise remote elements, such as a remote cloud computing element and/or remote storage for user information.

A wearable device might be worn at different locations on the wearer's body (i.e., the person monitoring their behavior) and the wearable device might be programmed or configured to account for those differences, as well as differences from wearer to wearer. For example, a right-handed person may wear the device around his right wrist whereas a left-handed person may wear the device around his left wrist. Users may also have different preferences for orientation. For example, some users may want the control buttons on one side, whereas other users may prefer the control buttons on the opposite side. In one embodiment, the user may manually enter the wrist preference and/or device orientation.

In another embodiment, the wrist preference and/or device orientation may be determined by asking the user to perform one or more pre-defined gestures and monitoring the sensor data from the wearable device corresponding to the user performing the pre-defined gesture or set of gestures. For example, the user may be asked to move his hand towards his mouth. The change in accelerometer sensor readings across one or more axes may then be used to determine the wrist and device orientation. In yet another example, the behavior tracking/feedback system may process the sensor readings from the wearable device while the user is wearing the device for a certain duration of time. Optionally, the behavior tracking/feedback system may further combine the sensor readings with other data or metadata about the wearer, to infer the wrist and device orientation. For example, the behavior tracking/feedback system may monitor the user for one day and record the accelerometer sensor readings across one or more of the axes.

Since the movement of the lower arm is constrained by the elbow and upper arm, some accelerometer readings will be more frequent than others based on the wrist and device orientation. The information of the accelerometers can then be used to determine the wrist and/or device orientation. For example, the mean, minimum, maximum and/or standard deviation of the accelerometer readings could be used to determine the wrist and/or device orientation.

In some embodiments, sensing devices can sense, without requiring user interaction, the start/end of a food intake event, the pace of eating, the pace of drinking, the number of bites, the number of sips, the estimation of fluid intake, and/or estimation of portion sizing. Operating with less human intervention, no human intervention, or only intervention not apparent to others will allow the devices to scale well with different meal scenarios and different social situations. Sensing might include capturing details of the food before it is consumed, as well as user actions that are known to accompany eating, such as repeated rotation of an upper arm or other hand-to-mouth motions. Sensors might include an accelerometer, a gyroscope, a camera, and other sensors.

Using the devices can provide a person with low friction-of-use to detect, quantify, track and provide feedback related to the person's food intake content as well as the person's food intake behavior. Such methods have the potential of preventing, treating and, in certain cases, even curing diet-related diseases. Such devices can improve efficacy, accuracy and compliance, and reduce the burden of usage and to improve social acceptance. The devices can operate autonomously with no, or very minimal, human intervention, and do not interfere in an invasive or otherwise significant negative way with a person's normal activities or social interactions or intrude on the person's privacy. The devices are able to handle a wide range of meal scenarios and dining settings in a discreet and socially-acceptable manner, and are capable of estimating and tracking food intake content and quantity as well as other aspects of eating behavior. The devices can provide both real-time and non-real-time feedback to the person about their eating behavior, habits and patterns.

It is generally known and understood that certain eating behaviors can be linked to, triggered by or otherwise be influenced by physical, mental or environmental conditions such as for example hunger, stress, sleep, addiction, illness, physical location, social pressure, and exercise. These characteristics can form inputs to the processing performed by or for the devices.

A food intake event generally relates to a situation, circumstance or action whereby a person eats, drinks or otherwise takes into his or her body an edible substance. Edible substances may include, but are not limited to, solid foods, liquids, soups, drinks, snacks, medications, vitamins, drugs, herbal supplements, finger foods, prepared foods, raw foods, meals, appetizers, main entrees, desserts, candy, breakfast, sports or energy drinks. Edible substances include, but are not limited to, substances that may contain toxins, allergens, viruses, bacteria or other components that may be harmful to the person, or harmful to a population or a subset of a population. Herein, for readability, food is used as an example of an edible substance, but it should be understood that other edible substance might be used instead of food unless otherwise indicated.

Eating habits and patterns generally relate to how people consume food. Eating habits and patterns may include, but are not limited to, the pace of eating or drinking, the size of bites, the amount of chewing prior to swallowing, the speed of chewing, the frequency of food intake events, the amount of food consumed during a food intake event, the position of the body during a food intake event, possible movements of the body or of specific body parts during the food intake event, the state of the mind or body during a food intake event, and the utensils or other devices used to present, handle or consume the food. The pace of eating or drinking might be reflected in the time between subsequent bites or sips.

Triggers generally relate to the reasons behind the occurrence of a food intake event, behind the amount consumed and behind how it is consumed. Triggers for food intake events and for eating habits or patterns may include, but are not limited to, hunger, stress, social pressure, fatigue, addiction, discomfort, medical need, physical location, social context or circumstances, odors, memories or physical activity. A trigger may coincide with the food intake event for which it is a trigger. Alternatively, a trigger may occur outside the food intake event window, and might occur prior to or after the food intake event at a time that may or may not be directly related to the time of the food intake event.

In some embodiments of the sensing device or system, fewer than all of the features and functionality presented in this disclosure are implemented. For example, some embodiments may focus solely on detection and/or processing and tracking of the intake of food without intending to steer the user to modify his or her food intake or without tracking, processing or steering eating habits or patterns.

In many examples herein, the setting is that an electronic device is provided to a user, who wears the electronic device, alone or while it is in communication with a nearby support device that might or might not be worn, such as a smartphone for performing operations that the worn electronic device offloads. In such examples, there is a person wearing the electronic device and that person is referred to as the "wearer" in the examples and the system comprises a worn device and may include other components that are not worn and are nearby and components that are remote, preferably able to communicate with the worn device. Thus, the wearer wears the electronic device, and the electronic device includes sensors, which sense environment about the wearer. That sensing can be of ambient characteristics, body characteristics, movement and other sensed signals as described elsewhere herein.

In many examples, functionality of the electronic device might be implemented by hardware circuitry, or by program code instructions that are configurable to be executed by at least one hardware processor in the electronic device, or a combination. Where it is indicated that a processor does something, it may be that the processor is caused to perform tasks as a consequence of executing instructions read from an instruction memory (e.g., a storage medium that includes program code instructions) wherein the instructions provide for performing that thing. In this regard, the program code instructions are configurable to cause the processor (or the host device) to perform certain methods, processes, or functions as defined by the executed instructions. While other people might be involved, a common example here is where the wearer of the electronic device is using that electronic device to monitor their own actions, such as gestures, behavior events comprising a sequence of gestures, activities, starts of activities or behavior events, stops of activities or behavior events, etc. Where it is described that a processor performs a particular process, it may be that part of that process is done separate from the worn electronic device, in a distributed processing fashion. Thus, a description of a process performed by a processor of the electronic device need not be limited to a processor within the worn electronic device, but perhaps a processor in a support device that is in communication with the worn electronic device.

Patient Management System

A patient management system might comprise a novel digital health app that runs on a device such as a smartphone or a dedicated device that can communicate with a wearable sensing apparatus worn by a person. The wearable sensing apparatus interacts with the app to provide for hybrid or autonomous management of insulin dosing and reminders.

In an example of a use of such a system, a person—referred to herein as a "patient"—has been diagnosed with Type 1 diabetes that requires external insulin to be provided to the patient. The insulin could be given in the form of injectable insulin using for example a pen or syringe, or via an insulin pump or a similar insulin dosing and dispensing device that is attached to the patient's body to introduce measured amounts of insulin into the patient's body. The dose amount and timing can be a function of when the patient is eating, begins eating, is imminently going to be eating, has been eating and will continue to eat, or has finished eating. A wearable device, capable of discerning gestures from movements and sensor data outputs, can determine, possibly without specific patient intervention, when an eating event has started, or is about to start, as well as the pace, duration and likely conclusion of an eating event. From this determination, the wearable device (or an ancillary device in communication with the wearable device, such as a full-function smartphone) would send a signal to the insulin dosing and dispensing device indicating some details of the eating/drinking and/or would send a message to the patient, a caretaker, and/or a health professional. In a different embodiment, the wearable device may communicate with an ancillary device such as a full-function smartphone, the smartphone may process the information received from the wearable, possibly combined with inputs from one or more other devices such as a continuous glucose monitoring ("CGM") device to determine insulin dosing amounts and/or timing and communicate dosing information back to the patient or to a insulin dispensing device that is attached to the patient.

For example, the wearable device might determine that the patient has started eating and from the pace of eating and a determined likely duration of the event, could signal to a dosing and delivery device some information about the eating event, which the delivery device could use to start a delivery of insulin to the patient. In addition, or instead, the wearable device could send a message relating to the eating event and the parameters measured. For example, the wearable device might communicate with a nearby smartphone that is running an app that is paired to that wearable device and send a message, perhaps as a cellular telephone network text message (e.g., SMS message) to a prestored number assigned to the patient, where the message says something like "A food event has been detected. Be sure to activate your insulin dosing and delivery device to dose insulin."

If the patient is the operator of the smartphone, perhaps the app could message the patient directly, without having to send a network text message. The message could be displayed on the phone, on the wearable device of the patient or on another electronic device with which the patient interacts. In some cases, it might be useful to have more than one recipient of the message. For example, where the patient needs or uses caregiver assistance, whether due to age (young or old) or for other reasons, the wearable device messaging can also go to the caregiver. Where useful or needed, this information can be provided to a health care professional, perhaps to monitor patient regimen compliance.

As used herein, an event might be described as an "eating event" or a "food intake event" rather than an eating event and/or a drinking event" for readability, but it should be understood that, unless otherwise indicated, a teaching herein related to an eating event or food intake event may equally apply to a drinking event.

Gesture-sensing technology can be used to automatically detect a gesture event without user prompting or interaction, such as gestures to indicate events when someone is eating or drinking from their hand gestures using motion sensors (accelerometer/gyroscope) in a wrist-worn wearable device or ring. This detection can occur in real time to deduce key insights about the consumption activity such as, for example, a start time of a consumption event, an end time of the consumption event, a consumption method, metrics associated with pace of consumption, metrics associated with quantities consumed, and metrics associated with frequency of consumption, location of consumption, etc. The gesture-sensing technology can be used for other activities and behaviors such as smoking, dental hygiene, hand hygiene, etc.

The gesture-sensing technology can automatically (i.e., without requiring user intervention) detect when someone is eating or drinking from their hand gestures using motion sensors (accelerometer/gyroscope) in a wrist-worn wearable device or ring. The motion sensors may also be embedded in another device generally worn on the arm, around the wrist, hand or fingers. The motion sensors could also be embedded into a tattoo or implanted into the patient's body. This detection can occur in real time or in near real time. The worn device might be combined with off-device processing and communication functionality, as might be found in a portable communication device. This off-device processing might be used for more complex processing tasks, such as deducing insights about a consumption activity such as, for example, start time, end time, consumption method, metrics associated with pace of consumption, metrics associated with quantities consumed, metrics associated with frequency of consumption, location of consumption, etc.

The start of each meal can be a critical moment for someone living with Type 1 diabetes. In an example of disease management, at the beginning of each meal, the patient (or caregiver, etc.) needs to decide whether and how much insulin to inject and an action needs to be taken based on that decision (e.g., an action of injecting insulin).

The patient management system can provide for early meal detection capabilities and provide powerful "nudges" that can help the patient and/or insulin dosing device with information for decision making and action taking. For example, the patient management system might send real-time reminders to administer insulin at start of meal. Forgetting to bolus is one of the main reasons for poor glycemic control, particularly among adolescents. The patient management system can prompt patients to check their blood sugar level at the start and/or end of a meal and can support easy logging. Logging might be handled from the wearable component of the system and it might be as discrete as the patient performing a wrist gesture to signal that the requested action (e.g., administering insulin or checking blood sugar level) has been performed or other movements that can serve as data entry actions.

Health care providers can survey their patients "in-the-moment", yielding more accurate and actionable insights (e.g., assess difficulty estimating carbs, emotions, need for help).

The patient management system can track, more generally, eating and drinking activities with seconds'-level accuracy, making it possible, for example, to correlate blood glucose levels and bolusing (insulin administration) actions back to exact eating times. This can be used in personalized nutrition research and in the development of personalized nutrition plans. This information may be an integral part of personalized diabetes care pathways.

The patient management system can be used in studies of the impact of real-time bolus reminders on medication adherence and glycemic control. Data sharing could occur in real-time or not in real-time. Data sharing could be with caregivers, health care professionals or, with appropriate privacy safeguards, provided as part of a larger data set to researchers and medical device developers.

One part of the patient management system is the app, which might provide a user interface to be used by the patient. This app could provide the ability to send real-time bolus reminders to the patient and a monitoring service that allows real-time alerts (notifications or text) to be sent to one or more destinations (e.g., telephone numbers, e-mail addresses, URLs, etc.) for remote caregivers and others. This could, for example, allow parents to remotely monitor their young Type 1 diabetes children's eating activities and responses to messages or alerts.

In some approaches, a patient manually informs an insulin delivery system when he or she is eating or is about to eat. Based on this input, the insulin delivery system will then start insulin delivery in one or multiple doses. This is not ideal, since the user needs to take the action of informing the insulin delivery system. It would be better if no action by the user were required. Alternatively, an insulin delivery system could infer the occurrence of a food intake event from monitoring changes in the patient's blood glucose levels. Direct blood glucose level measurement can be impractical. Interstitial glucose levels can be measured automatically and periodically using a continuous glucose monitoring device and those levels are often used as a proxy for blood glucose levels. However, interstitial glucose level measurements can be delayed by 20 minutes or more. This is too late to achieve good glycemic control and so interstitial fluid measurements can be less than ideal to inform an insulin delivery system.

There is a need for automatic detection of food intake events to inform an insulin delivery system and allow insulin delivery systems to operate without or with reduced human intervention. The patient management system can be used as a medication reminder system in general or more specifically, an insulin therapy system.

An example of a patient management system will now be described.

Upon the detection of an actual or imminent start of a food intake event, a message/alert may be sent to the patient to remind him or her to take his/her medication. The medication could be insulin or other medication, such as medications that need to be taken before, during, or after eating a meal. In certain cases, it may be desirable to have a delay between the detection of an actual or imminent start of a food intake event and the time when the alert is sent and this can be tuned as needed. For example, instead of sending an alert at the start of a food intake event, an alert may be sent after the system has detected that five, ten or some other certain number of bites or sips has been consumed. In another example, an alert might be sent one minute, five minutes or some other certain fixed time after the system has detected an actual or imminent start of a food intake event. The timing of the alert may also depend at least in part on the confidence level of the patient management system that an actual or imminent start of food intake event has occurred. The alert might be sent when or some time after the patient management system has found conditions which, historically, preceded an eating event. Based on historical data recorded by the patient management system from the patient's past eating events, the patient management system might be able to determine that a notification or reminder is needed ten minutes before a meal, at the start of a meal, or during the meal. The patient management system might also be programmed to deal with "snooze" events, wherein the patient is notified with an alert and the patient indicates that the patient management system should resend the reminder at a defined time in the near future, such as at a defined period of time after the initial alert or reminder or at a defined number of bites after the initial alert or reminder.

When the patient management system sends a message/alert to the patient, one or more persons or one or more systems may also be notified via ancillary messaging. The other person(s) or system(s) may be notified of the actual, probable or imminent start of a food intake event. If the message/alert to the patient included a mechanism for the patient to respond, the other person(s) or system(s) may be informed of the patient's response. The other person(s) or system(s) may also be informed if the patient failed to respond. This might be helpful in the case of parents and/or caregivers who support a patient.

In some cases, the patient management system might be programmed to accept different inputs from the patient. For example, the patient management system might have a user interface to accept from the patient an indication that a meal has concluded, that the meal will have zero, many, or some measure of carbohydrates.

As with the patient messaging, for this ancillary messaging, there may be a delay between the detection of an actual or imminent start of a food intake event and the time when the alert is sent. Instead of sending an alert at the start of a food intake event, an alert may be sent after the system has detected that a certain number of bites or sips have been consumed. There may be a delay between sending the alert to the patient and notifying the other person(s) or system(s). If the message/alert to the patient included a mechanism for the patient to respond, there may be a delay between the patient responding to the message/alert and the other person(s) or system(s) being informed of the person's response or failure to respond.

One or more other persons may be notified via a message that is sent over a cellular network. For example, a text message on his or her phone or other mobile or wearable device.

An insulin therapy system will now be described.

The detection of an actual, probable or imminent start of a food intake event as described herein can be used to inform an insulin delivery system. Upon receiving a signal indicating an actual, probable or imminent start of a food intake event, the insulin delivery system may calculate or estimate the adequate dosage of insulin to be administered and the schedule for delivery of the insulin.

The insulin delivery system may use other parameters and inputs in calculating or estimating the dosing and frequency. For example, the insulin delivery system may use current or prior glucose level readings, fluctuations in glucose level readings, parameters derived from glucose level readings or insulin-on-board (i.e., the insulin that was administered at an earlier time but is still active in the patient's body). Examples of parameters derived from glucose level readings could be the current slope (i.e. first derivative), the second or higher order derivative of a glucose level reading, the maximum, mean, minimum value of the glucose level readings in a certain time window preceding the current food intake event, etc.

The insulin delivery system may also include parameters related to the meal activity itself, such as the duration of the meal, the pace of eating, the amounts consumed. The insulin delivery system may also use other sensor inputs such as heart rate, blood pressure, body temperature, hydration level, fatigue level, etc. and can obtain these from its own sensors or obtain some of them from other devices the patient might be using for this or for other purposes.

The insulin delivery system may also include other inputs, such as current or past physical activity levels, current or past sleep levels, and current or past stress levels. The insulin delivery system may also include specific personal information such as gender, age, height, weight, etc. The insulin delivery system may also include information related to a patient's insulin needs. This could be information entered or configured by the patient, by a caregiver or by a health record or healthcare maintenance system. Information related to a patient's insulin needs may also be derived from historical data collected and stored by the insulin delivery system. For example, the amounts of insulin delivered by the insulin delivery system in a period of time preceding the current food intake event.

In another embodiment, the insulin delivery system may take into account the amounts of insulin and delivery schedule associated with one or more prior food intake events that occurred at or around the same time of day and/or the same day of week, or within a defined time window around the current time of day. An insulin delivery system may also take into account a patient's current location.

Additional parameters related to the food intake event can also be used to inform an insulin delivery system. An insulin delivery system may use such parameters to calculate or estimate an adequate dosage of insulin to be delivered and/or the schedule for the insulin delivery. Such parameters may include, but are not limited to duration of eating or drinking, amounts of food or drinks consumed, pace of eating, amount of carbohydrates consumed, eating method or type of utensils or containers used. Some of these additional parameters (e.g., duration or pace) may be computed by the food intake tracking and feedback system without requiring any user intervention. In other cases, a user intervention, input or confirmation by the user may be necessary.

An insulin delivery system may also use parameters related to past food intake events to calculate or estimate the adequate insulin dosage and insulin delivery schedule. The insulin delivery system may also include parameters related to past food intake events, including parameters related to the time, location, duration, pace of eating or drinking, amounts consumed, eating method, utensils used, content consumed etc. Other parameters are also possible. For example, an insulin delivery system may take into account the duration of one or more past food intake events and/or average pace of eating for one or more past food intake events. In certain embodiments, the insulin delivery system might only consider parameters related to past food intake events that occurred within a specific time window prior to the current food intake event. In certain embodiments, the insulin delivery system might only consider parameters from past food intake events that occurred at or around the same time of day and/or the same day of week of the current food intake event. In certain embodiments, the insulin delivery system might only take into account parameters from one or more past food intake events that occurred at or near the same location as the current food intake event.

In certain embodiments, the insulin delivery system may look at the impact of past insulin dosages and delivery schedules on blood glucose readings or on other sensor outputs that are used as a proxy for the blood glucose readings, such as for example the interstitial glucose readings, to calculate or estimate the insulin dosage and determine the delivery schedule of a current food intake event.

An insulin delivery system may continuously or periodically process its logic and update the logic for insulin dosing and/or insulin delivery scheduling accordingly based on one or more of the parameters described above.

The patient management system can be generalized beyond insulin, to administration of a medication or substance that needs to be administered in conjunction with a food intake event, especially if the amount of medication or other substance is related to parameters associated with the food intake event.

A filter can be applied to determine if the meal is part of a qualified/applicable meal category.

The patient management system might be programmed to perform continuous, or periodic and frequent, evaluation during a meal and adjust the schedule or insulin amounts upwards or downwards based on observed changes in blood glucose level readings (or proxies thereof, such as interstitial glucose level readings). In one specific embodiment, insulin delivery may be suspended if a glucose level reading is below a certain threshold, or if a predictive algorithm embodied in executable program code executed by the patient management system outputs a prediction that a glucose reading will be below a certain level at a future time if the current amounts and schedule are executed.

In this manner, the patient management system can send notifications and send signals to an insulin delivery device, while taking into account the start of eating, the pace of eating, the anticipated end of eating, the duration of eating and other factors. For example, the patient management system might instruct the insulin delivery device to deliver insulin at the start of eating and during eating, using various inputs, such as heart rate, eating rate, body temperature, etc. to make adjustments. In this manner, the patient management system can be part of a meal-aware, autonomous or semi-autonomous artificial pancreas.

DESCRIPTION OF THE FIGURES

FIG. 1 shows a high level functional diagram of a dietary tracking and feedback system in accordance with an embodiment. A system for dietary tracking and feedback may in part include one or more of the following: a food intake event detection subsystem 101, one or more sensors 102, a tracking and processing subsystem 103, a feedback subsystem 106, one or more data storage units 104 and a learning subsystem 105 that might perform non-real-time analysis. In some embodiments, elements shown in FIG. 1 are implemented in electronic hardware, while in others some elements are implemented in software and executed by a processor. Some functions might share hardware and processor/memory resources and some functions might be distributed. Functionality might be fully implemented in a sensor device such as wrist worn wearable device, or functionality might be implemented across the sensor device, a processing system that the sensor device communicates with, such as a smartphone, and/or a server system that handles some functionality remote from the sensor device.

For example, a wearable sensor device might make measurements and communicate them to a mobile device, which may process the data received from the wearable sensor device and use that information possibly combined with other data inputs, to activate tracking and processing subsystem 103. The tracking and processing subsystem 103 may be implemented on the mobile device, on the wearable sensor device, or on another electronic device. The tracking and processing subsystem 103 may also be distributed across multiple devices such as for example across the mobile device and the wearable sensor device. The communication might be over the Internet to a server that further processes the data. Data or other information may be stored in a suitable format, distributed over multiple locations or centrally stored, in the form recorded, or after some level of processing. Data may be stored temporarily or permanently.

A first component of the system illustrated in FIG. 1 is the food intake event detection subsystem 101. A role of food intake event detection subsystem 101 is to identify the start and/or end of a food intake event and communicate an actual, probable or imminent occurrence of an event. An event could, for example, be an event related to a specific activity or behavior. Other examples of an event that may be detected by event detection subsystem 101 could be an operator on a production line or elsewhere performing a specific task or executing a specific procedure. Yet another example could be a robot or robotic arm performing a specific task or executing a specific procedure on a production arm or elsewhere.

In general, the device detects what could be the start of a food intake event or the probable start of a food intake event, but the device would work sufficient for its purposes so long as the device reasonably determines such start/probable start. For clarity, that detection is referred to as a "deemed start" of a food intake event and when various processes, operations and elements are to perform some action or behavior in connection with the start of a food intake event, it would be acceptable for those various processes, operations and elements to take a deemed start as the start even if occasionally the deemed start is not in fact a start of a food intake event.

In one embodiment, the detection and/or signaling of the occurrence of the deemed start of a food intake event coincides with the deemed start of a food intake event. In another embodiment, it may occur sometime after the deemed start of the food intake event. In yet another embodiment, it may occur sometime before the deemed start of the food intake event. It is usually desirable that the signaling is close to the deemed start of the food intake event. In some embodiments of the current disclosure, it may be beneficial that the detection and/or signaling of the deemed start of a food intake event occurs ahead of the start of said food intake event. This may for example be useful if a message or signal is to be sent to the user, a healthcare provider or caregiver ahead of the start of the food intake event as a coaching mechanism to help steer a user's food intake decisions or eating habits.

Methods for event detection may include, but are not limited to, detection based on monitoring of movement or position of the body or of specific parts of the body, monitoring of arm movement, position or gestures, monitoring of hand movement, position or gestures, monitoring of finger movement, position or gestures, monitoring of swallowing patterns, monitoring of mouth and lips movement, monitoring of saliva, monitoring of movement of cheeks or jaws, monitoring of biting or teeth grinding, monitoring of sound and other signals from the mouth, the throat and the digestive system. Methods for detection may include visual, audio or any other types of sensory monitoring of the person and/or his or her surroundings.

The monitored signals may be generated by the dietary tracking and feedback system. Alternatively, they may be generated by a separate system but be accessible to the dietary tracking and feedback system through an interface. Machine learning and other data analytics techniques may be applied to detect the start or probable start of a food intake event from the input signals being monitored.

In one example, the food intake detection system 101 may monitor the outputs of accelerometer and/or gyroscope sensors to detect a possible bite gesture or a possible sip gesture. Such gestures might be determined by a gesture processor that uses machine learning to distill gestures from sensor readings. The gesture processor might be part of the processor of the worn device or in another part of the system.

Gesture detection machine learning techniques as described elsewhere herein may be used to detect a bite gesture or sip gesture, but other techniques are also possible. The food intake detection system 101 may further assign a confidence level to the detected bite gesture or sip gesture. The confidence level corresponds to the likelihood that the detected gesture is indeed a bite or sip gesture. The food intake detection system may determine that the start of a food intake event has occurred based on the detection of a gesture and its confidence level without any additional inputs. For example, the food intake event detection system 101 may decide that the start of a food intake event has occurred when the confidence level of the bite or sip gesture exceeds a pre-configured threshold.

Alternatively, when a possible bite or sip gesture has been detected, the food intake event detection system 101 may use additional inputs to determine that the start or probable start of a food intake event has occurred. In one example, the food intake event detection system 101 may monitor other gestures that are close in time to determine if the start of a food intake event has occurred. For example, upon detection of a possible bite gesture, the food intake event detection system 101 may wait for the detection of another bite gesture within a certain time window following the detection of the first gesture and/or with a certain confidence level before determining that the start of a food intake event had occurred.

Upon such detection, the food intake detection system 101 may place one or more circuits or components into a higher performance mode to further improve the accuracy of the gesture detection. In another example, the food intake event detection system 101 may take into consideration the time of the day, or the location of the user to determine if the start or probable start of a food intake event has taken place. The food intake event detection system may use machine learning or other data analytics techniques to improve the accuracy and reliability of its detection capabilities. For example, training data obtained from the user and/or from other users at an earlier time may be used to train a classifier. Training data may be obtained by asking for user confirmation when a possible bite or sip gesture has been detected. A labeled data record can then be created and stored in memory readable by the gesture processor that includes the features related to the gesture, along with other contextual features, such as time of day or location. A classifier can then be trained on a labeled dataset comprised of multiple labeled data records set of labeled data records, and the trained classifier model can then be used in a food intake event detection system to more accurately detect the start of a food intake event.

In another embodiment, the food intake detection subsystem may use triggers to autonomously predict the probable start of a food intake event. Methods for autonomous detection of a probable start of a food intake event based on triggers may include, but are not limited to, monitoring of a person's sleep patterns, monitoring of a person's stress level, monitoring of a person's activity level, monitoring of a person's location, monitoring of the people surrounding a person, monitoring of a person's vital signs, monitoring of a person's hydration level, monitoring of a person's fatigue level. In some cases, the food intake detection subsystem may monitor one or more specific trigger signals or trigger events over a longer period of time and, in combination with the non-real-time analysis and learning subsystem 105 apply machine learning or other data analytics techniques to predict the probable occurrence of a start of a food intake event.

For example, without any additional information, it can be very difficult to predict when a user will eat breakfast. However, if the system has a record over a number of days of the user's wake up time and the day of the week, the system can use that historical pattern in determining a likely time for the user to eat breakfast. Those records might be determined by the system, possibly with feedback from the user about their accuracy or those records might be determined by the user and input via a user interface of the system. The user interface might be the worn device itself or, for example, a smartphone app. As a result, the system can process correlations in the historical data to predict the time or time window that the user is most likely to have breakfast based on the current day of week and at what time the user woke up. Other trigger signals or trigger events may also be used by the non-real-time analysis and learning subsystem 105 to predict the time that a user will eat breakfast.

In another example, the non-real-time analysis and learning system 105 may, over a certain period of time record the stress level of a user. The stress level may, for example, be determined by monitoring and analyzing the user's heart rate or certain parameters related to the user's heart rate. The stress level may also be determined by analyzing a user's voice. The stress level may also be determined by analyzing the content of a user's messages or electronic communication. Other methods for determining the stress level are also possible. The non-real-time analysis and learning system 105 may furthermore, over the same period of time, record the occurrence of food intake events and certain characteristics of the food intake event such as the pace of eating, the quantity of food consumed, the time spacing between food intake events, etc. It may then be possible by analyzing the historical data of stress levels, the occurrence of food intake events and food intake event characteristics and by looking at correlations in the historical data of stress levels, the occurrence of food intake events and food intake event characteristics, to predict based on the current stress level the probability that a user will start a food intake event in a certain time window in the future, or predict what time window in the future, the user will be most likely to start a food intake event. It may also be possible to predict characteristics of said food intake event, such as for example pace of eating or quantity of consumption.

In specific embodiments, the non-real time analysis and learning subsystem 105 may use historical data from different users, or a combination of data from other users and from the wearer, and use similarities between one or more of the different users and the wearer, such as age, gender, medical conditions, etc. to predict the probable start of a food intake event by the wearer.

In yet other examples, the non-real-time analysis and learning subsystem 105 may use methods similar to the methods described herein to predict when a user is most likely to relapse in a binge eating episode or is most likely to start convenience snacking.

A variety of sensors may be used for such monitoring. The monitored signals may be generated by the dietary tracking and feedback system. Alternatively, they may be generated by a separate system but be accessible to the dietary tracking and feedback system for processing and/or use as trigger signals. Machine learning and other data analytics techniques may also be applied to predict some other characteristics of the probable intake event, such as the type and/or amount of food that will likely be consumed, the pace at which a person will likely be eating, the level of satisfaction a person will have from consuming the food, etc.

The machine learning process performed as part of gesture recognition might use external data to further refine its decisions. This might be done by non-real-time analysis and learning subsystem process. The data analytics process might, for example, consider the food intake events detected by the gesture-sensing based food intake detection system and the gesture-sensing based tracking and processing system, thus forming a second layer of machine learning. For example, over a period of time, food intake events and characteristics related to those food intake events are recorded, such as eating pace, quantity of food consumption, food content, etc., while also tracking other parameters that are not directly, or perhaps not obviously, linked to the food intake event. This could be, for example, location information, time of day a person wakes up, stress level, certain patterns in a person's sleeping behavior, calendar event details including time, event location and participant lists, phone call information including time, duration, phone number, etc., email meta-data such as time, duration, sender, etc. The data analytics process then identifies patterns and correlations. For example, it may determine a correlation between the number of calendar events during the day and the characteristics of the food intake event(s) in the evening. This might be due to the user being more likely to start snacking when arriving home, or that dinner is larger and/or more rushed when the number of calendar event(s) for that day exceeds a certain threshold. With subsystem 105, it becomes possible to predict food intake events and characteristics from other signals and events that are not obviously linked to food intake. Additional contextual metadata such as location, calendar information, day of week or time of day may be used by the processing and analysis subsystem to make such a determination or prediction.

Processing and analysis of one or more sensor inputs, and/or one or more images over longer periods of time, optionally using machine learning or other data analytics techniques may also be used to estimate the duration of a food intake event or may be used to predict that the end of a food intake event is probable or imminent.

In another embodiment, some user input 108 may be necessary or desirable to properly or more accurately detect the start and/or end of a food intake event. Such user input may be provided in addition to external inputs and inputs received from sensors 102. Alternatively, one or more user inputs may be used instead of any sensor inputs. User inputs may include, but are not limited to activating a device, pressing a button, touching or moving a device or a specific portion of a device, taking a picture, issuing a voice command, making a selection on a screen or entering information using hardware and/or software that may include but is not limited to a keyboard, a touchscreen or voice-recognition technology. If one or more user inputs are required, it is important that the user interaction is conceived and implemented in a way that minimizes the negative impact on a person's normal activities or social interactions.

A food intake event detection subsystem 101 may combine multiple methods to autonomously detect or predict the actual, probably or imminent start and/or end of a food intake event.

Another component of the system is the tracking and processing subsystem 103. In a preferred embodiment of the present disclosure, this subsystem interfaces 109 with the food intake event detection subsystem 101, and gets activated when it receives a signal from the food intake event detection subsystem 101 that the actual, probable or imminent start of an event has been detected, and gets disabled when or sometime after it receives a signal from the food intake event detection subsystem 101 that the actual, probable or imminent ending of an event has been detected. Upon detection of the start of a food intake event, the device might trigger activation of other sensors or components of the food intake tracking system, and might also trigger the deactivation of those upon detection of the end of the food intake event.

Application: Food Logging

In existing food journaling methods, if a user forgets to make an entry or does not make an entry for another reason (intentionally or unintentionally), there is no record or history of the eating event. This leads to food diaries being incomplete, inaccurate and considerably less useful for therapeutic purposes. Furthermore, content recorded in existing food logging methods is typically limited to selfreporting of content and amounts. There is no information about important characteristics of how the food was consumed (e.g., pace, duration of meal).

The monitoring system shown in FIG. 1 may be used to automate or reduce the friction of food logging. In one embodiment of the present disclosure, event detection subsystem 101 uses information deduced from motion sensors such as an accelerometer or gyroscope to detect and monitor eating or drinking events from a subject's hand gestures. In other embodiments, different sensor inputs may be used to deduce eating or drinking events. Other sensors may include, but are not limited to, heart rate sensors, pressure sensors, proximity sensors, glucose sensors, optical sensors, image sensors, cameras, light meters, thermometers, ECG sensors and microphones.

Outputs of event detection subsystem 101 that indicate the occurrence of a subject's eating or drinking events are recorded. Event detection subsystem 101 may do additional processing to obtain additional relevant information about the event such as start time, end time, metrics representative of the subject's pace of eating or drinking, metrics representative of quantities consumed. This additional information may also be recorded.

The detection of the occurrence of an eating or drinking event may be recorded as an entry in a food journal. Additional information associated with the eating or drinking event that can be obtained from the event detection subsystem may also be recorded as part of the consumption event entry in the food journal. This can take the place of manually entering each eating event.

Information about eating or drinking events being recorded may include time of event, duration of event, location of event, metrics related to pace of consumption, metrics related to quantities consumed, eating method(s), utensils used, etc.

Application: Medication Adherence

Since the event system is able to monitor events and gestures and determine consumption, this can be used to automatically monitor a medication administration protocol that defines when medication needs to be taken and with what foods or other actions. This may be with specific meal categories such breakfast, at certain times of day, etc. A medication administration protocol might specify if a patient should eat or drink with medication. Optionally, the medication administration protocol may also specify how much food or liquid a patient should consume.

For example, when medication needs to be taken at certain times of day, a medication adherence system can monitor the time and, when it is time to take medication, issue an alert. It may then also activate the event detection subsystem (if it is not yet already active) and start monitoring the outputs of the event detection subsystem. It waits for a notification confirmation from user that he/she has taken the medication.

If a confirmation is received and if the medication administration protocol prescribes that medication needs to be taken with food or liquid, the medication adherence system monitors the outputs from eating/drinking event detection subsystem and determines if rules specified by medication administration protocol are met. This could be as simple as confirming that an eating or drinking event has occurred with or shortly after the intake of the medication. In case the medication administration protocol specifies that a minimum amount of food or fluid needs to be consumed, the medication adherence system may monitor the additional outputs of the event detection subsystem (metrics related to quantities consumed) to confirm that this condition is met.

Different rules/logic to determine if the medication administration protocol has been met is also possible.

If no confirmation is received, the medication adherence subsystem may issue a second notification. Additional notifications are also possible. After a pre-configured number of notifications, the medication adherence subsystem may issue an alert. Alerts may be issued to user as a text message, or may be sent to a remote server over the internet or over a cellular connection (e.g., to hospital, caregiver).

If medication needs to be taken with specific meal categories, the medication adherence system may monitor the outputs of an eating detection subsystem. When an eating event is detected, it will use logic to determine the applicable meal category. If the meal category matches the category described by the medication administration protocol, it will issue a notification to remind the user to take his/her medication. If the medication administration protocol prescribes that food or liquid should be consumed with the medication, the monitoring logic outlined above may be implemented to determine that the medication administration protocol has been adhered to.

The medication adherence system may monitor the outputs of an eating event detection subsystem to determine if the start of an eating event has occurred and determine if the eating event is of the applicable meal category. When an eating event is detected and the meal category matches the category described by the medication administration protocol, certain actions might be taken, such as that it may activate an object information retrieval system (e.g., NFC tags, imaging) to collect more information about the objects the user is interacting with. In this way, it may obtain information about the medication from an NFC tag attached to the pill box or medication container. In another use, it may verify that the medication matches the medication prescribed by the medication administration protocol and/or issue a notification to remind the user to take his/her medication. If the medication administration protocol prescribes that food or liquid should be consumed with the medication, the monitoring logic outlined above may be implemented to determine that the medication administration protocol has been adhered to.

The system might also incorporate details about the medication obtained from the object information collection system or through a different method in the notification, record confirmations in response to the notification from user that he/she has taken the medication, ask the user for additional information about the medication, and/or send the user a follow-on question at a pre-configured time after the user has taken the medication to get additional inputs. (e.g., query about how the user is feeling, query about pain levels, prompt to measure blood sugar level).

Additional Embodiments

In another embodiment of the current disclosure, the tracking and processing subsystem may be activated and/or deactivated independent of any signals from the food intake detection subsystem. It is also possible that certain parameters be tracked and/or processed independently of any signals from the food intake detection subsystem, whereas the tracking and/or processing of other parameters may only be initiated upon receiving a signal from the food intake event detection subsystem.

The sensor inputs may be the same or similar to the inputs sent to the food intake event detection subsystem. Alternatively, different and/or additional sensor inputs may be collected. Sensors may include, but are not limited to, accelerometers, gyroscopes, magnetometers, image sensors, cameras, optical sensors, proximity sensors, pressure sensors, odor sensors, gas sensors, Global Positioning Systems (GPS) circuit, microphones, galvanic skin response sensors, thermometers, ambient light sensors, UV sensors, electrodes for electromyographic ("EMG") potential detection, bio-impedance sensors, spectrometers, glucose sensors, touchscreen or capacitive sensors. Examples of sensor data include motion data, temperature, heart rate, pulse, galvanic skin response, blood or body chemistry, audio or video recording and other sensor data depending on the sensor type. The sensor inputs might be communicated to a processor wirelessly or via wires, in analog or digital form, intermediated by gating and/or clocking circuits or directly provided.

Processing methods used by the tracking and processing subsystem may include, but are not limited to, data manipulation, algebraic computation, geo-tagging, statistical computing, machine learning, computer vision, speech recognition, pattern recognition, compression and filtering.

Collected data may optionally be temporarily or permanently stored in a data storage unit. A tracking and processing subsystem may use an interface to the data storage unit to place data or other information in the data storage unit and to retrieve data or other information from the data storage unit.

In a preferred embodiment of the present disclosure, the collection of data, processing and tracking happen autonomously and do not require any special user intervention. Tracked parameters may include, but are not limited to, the following: location, temperature of surroundings, ambient light, ambient sounds, biometric information, activity levels, image captures of food, food names and descriptions, portion sizes, fluid intake, caloric and nutrient information, counts of mouthfuls, bite counts, sip counts, time durations between consecutive bites or sips, and duration of food intake events. Tracked parameters may also include, for each bite or sip, the time duration that the user's hand, arm and/or utensil is near the user's mouth, the time duration that the content of the bite or sip resides in the user's mouth before swallowing. The methods may vary based on what sensor data is available.

In other embodiments of the present disclosure, some user intervention is required or may be desirable to achieve for example greater accuracy or input additional detail. User interventions may include, but are not limited to, activating a device or specific functionality of a device, holding a device in position, taking pictures, adding voice annotations, recording video, making corrections or adjustments, providing feedback, doing data entry, taking measurements on food or on food samples. Measurements may include, but are not limited to, non-destructive techniques such as for example obtaining one or more spectrographs of food items, or chemistry methods that may require a sample taken from the food.

The processing of sensor data and user inputs by the tracking and processing subsystem 103 usually occurs real-time or near real-time. There may be some delays, for example to conserve power or to work around certain hardware limitations, but in some embodiments, the processing occurs during the food intake event, or in case of tracking outside of a food intake event, around the time that the sensor or user inputs have been received.

In certain implementations or under certain circumstances, there may not be real-time or near real-time access to the processing unit required to perform some or all of the processing. This may, for example, be due to power consumption or connectivity constraints. Other motivations or reasons are also possible. In that case, the inputs and/or partially processed data may be stored locally until a later time when access to the processing unit becomes available.

In one specific embodiment of the present disclosure, sensor signals that track movement of a person's arm, hand or wrist may be sent to the tracking and processing subsystem 103. The tracking and processing subsystem 103 may process and analyze such signals to identify that a bite of food or sip of liquid has been consumed or has likely been consumed by said person. The tracking and processing subsystem 103 may furthermore process and analyze such signals to identify and/or quantify other aspects of eating behavior such as for example the time separation between bites or sips, the speed of hand-to-mouth movement etc. The tracking and processing subsystem 103 may furthermore process and analyze such signals to identify certain aspects of the eating method such as, for example, whether the person is eating with a fork or spoon, is drinking from a glass or can, or is consuming food without using any utensils.

In a specific example, it might be that the wearer rotates his or her wrist in one direction when bringing an eating utensil or hand to the mouth when taking a bite, but rotates in the other direction when sipping a liquid. The amount of rotation of a wearer's wrist as he or she moves his or her wrist to the mouth or away from the mouth and the duration that the wrist is held at a higher rotation angle may also be different for a drinking gesture versus an eating gesture. Other metrics may be used to distinguish eating gestures from drinking gestures or to distinguish differences in eating methods. A combination of multiple metrics may also be used. Other examples of metrics that may be used to distinguish eating gestures from drinking gestures or to distinguish differences in eating methods include but are not limited to the change in angle of the roll from the start or approximate start of the gesture until the time or approximate time that the hand reaches the mouth, the change in angle of the roll from the time or approximate time that the hand is near the mouth until the end or approximate end of the gesture, the variance of accelerometer or gyroscope readings across one or more of the axes for a duration of time when the hand is near the mouth, or for a duration of time that is centered around when the hand is near the mouth, or for a duration of time that may not be centered around when the hand is near the mouth but that includes the time when the hand is the nearest to the mouth, the variance of the magnitude of the accelerometer readings for a duration of time when the hand is near the mouth, or for a duration of time that is centered around when the hand is the nearest to the mouth, or for a duration of time that may not be centered around when the hand is the nearest to the mouth but that includes the time when the hand is the nearest to the mouth, the maximum value of the magnitude of the accelerometer readings for a duration of time when the hand is near the mouth, or for a duration of time that is centered around when the hand is the nearest to the mouth, or for a duration of time that may not be centered around when the hand is the nearest to the mouth but that includes the time when the hand is the nearest to the mouth. The magnitude of the accelerometer reading may be defined as square root of the acceleration in each orthogonal direction (e.g., sense acceleration in the x, y, and z directions and calculate $SQRT(ax^2+ay^2+az^2)$).

The position of the hand vis-à-vis the mouth can, for example, be determined by monitoring the pitch or the worn device and from there the pitch of the wearer's arm. The time corresponding to the peak of the pitch could be used as the moment in time when the hand is the nearest to the mouth. The time when the pitch starts rising could, for example, be used as the start time of the gesture. The time when the pitch stops falling could for example be used as the end time of the gesture.

Other definitions for nearest mouth position, start of movement and end of movement are also possible. For example, the time when the roll changes direction could be used instead to determine the time when the arm or hand is the nearest to the mouth. The time when the roll stops changing in a certain direction or at a certain speed could be used instead to determine the start time of the movement towards the mouth.

The tracking and processing subsystem may furthermore process and analyze such signals to determine appropriate or preferred times to activate other sensors. In one specific example, the tracking and processing subsystem may process and analyze such signals to determine an appropriate or preferred time to activate one or more cameras to take one or more still or moving images of the food. By leveraging sensors that track arm, hand, finger or wrist movement and/or the orientation and position of the camera to activate the camera and/or automate the image capture process, the complexity, capabilities and power consumption of the image-capture and image analysis system can be greatly reduced, and in certain cases better accuracy may be achieved. It also significantly reduces any privacy invasion concerns, as it now becomes possible to more precisely control the timing of image capturing and make it coincide with the cameras being focused on the food.

For example, the processor might analyze motion sensor inputs from an accelerometer, a gyroscope, a magnetometer, etc., to identify the optimal time to activate camera and capture picture and trigger the camera at that time, perhaps based on when the processor determines that the view region of the camera encompasses the food to be photographed. In one example, the processor determines the start of an eating event and signals the wearer to capture an image of the food being eaten and also determines the end of the eating event and again signals the wearer to capture an image of what remains of the food or the plate, etc. Such images can be processed to determine consumption amounts and/or to confirm consumption amounts already determined by the processor. In some embodiments, the image processing can be used as part of feedback to train machine learning that the processor uses.

In some embodiments, the system may use sensors that track the movement of the wearer's arm or hand and only activate the camera when the system determines from the movement sensing that the arm or hand are near the mouth. In another example, the system may activate the camera sometime between the start of the movement towards the mouth and the time when the arm or hand is the nearest to the mouth. In yet another example, the system may activate the camera sometime between the time when the arm or hand is the nearest to the mouth and the end of the movement away from the mouth.

As mentioned above, the position of the hand vis-à-vis the mouth can be determined by monitoring the pitch and a rising pitch indicating a start time of a movement towards the mouth and a falling pitch indicating an end time. Other definitions for nearest mouth position, start of movement and end of movement are also possible.

The position of the hand vis-à-vis the mouth can, for example, be determined by monitoring the pitch or the worn device and from there the pitch of the wearer's arm. The time corresponding to the peak of the pitch could be used as the moment in time when the hand is the nearest to the mouth. The time when the pitch starts rising could, for example, be used as the start time of the gesture. The time when the pitch stops falling could for example be used as the end time of the gesture.

The processing and analysis of sensor signals that track movement of a user's arm, hand or wrist may be combined with other methods such as the image capture of food as it enters the mouth as proposed to build in redundancy and improve the robustness of a dietary tracking and feedback system. For example, by processing and analysis of a user's arm, hand or wrist movement, information related to bite count and bite patterns would still be preserved, even if the camera were to be obscured or tampered with.

One or more of the sensor inputs may be still or streaming images obtained from one or more camera modules. Such images may require some level of processing and analysis. Processing and analysis methods may, among other methods, include one or more of the following methods: compression, deletion, resizing, filtering, image editing, and computer vision techniques to identify objects such as, for example, specific foods or dishes, or features such as, for example, portion sizes.

In addition to measuring bite counts and sip counts, the processor might analyze specifics, such as cadence and duration, to determine bite and sip sizes. Measuring the time that the wearer's hand, utensil or fluid container was near their mouth might be used to derive a "near-mouth" duration that is in turn used as an input to generate an estimate size of the bite or sip. The amount of rotation of the wrist when sipping might be useful for hydration tracking.

Measuring the amount of rotation of the wrist in one or more time segments that are within the start and the end of the gesture may also be used to estimate the size of the bite or sip. For example, a system may measure the amount of rotation of the wrist from a time sometime after the start of the gesture to the time when the arm or hand is the nearest to the mouth. The time corresponding to the peak of the pitch could be used as the moment in time when the hand is the nearest to the mouth. The time when the pitch starts rising could for example be used as the start time of the movement towards the mouth. The time when the pitch stops falling could for example be used as the end time of the movement away from the mouth. Other definitions for nearest mouth position, start of movement and end of movement are also possible. For example, the time when the roll changes direction could be used instead as the time when the arm or hand is the nearest to the mouth. The time when the roll stops changing in a certain direction or at a certain speed could be used as the start time of the movement towards the mouth. One or more still or streaming images may be analyzed and/or compared by the tracking and processing subsystem for one or multiple purposes including, but not limited to, the identification of food items, the identification of food content, the identification or derivation of nutritional information, the estimation of portion sizes and the inference of certain eating behaviors and eating patterns.

As one example, computer vision techniques, optionally combined with other image manipulation techniques may be used to identify food categories, specific food items and/or estimate portion sizes. Alternatively, images may be analyzed manually using a Mechanical Turk process or other crowdsourcing methods. Once the food categories and/or specific food items have been identified, this information can be used to retrieve nutritional information from one or more foods/nutrition databases.

As another example, information about a user's pace of eating or drinking may be inferred from analyzing and comparing multiple images captured at different times during the course of a food intake event. As yet another example, images, optionally combined with other sensor inputs, may be used to distinguish a sit-down meal from finger foods or snacks. As yet another example, the analysis of one image taken at the start of a food intake event and another image taken at the end of a food intake event may provide information on the amount of food that was actually consumed.

In a general case, sensor data is taken in by a processor that analyzes that sensor data, possibly along with prior recorded data and/or metadata about a person about whom the sensor data is sensing. The processor performs computations, such as those described herein, to derive a sequence of sensed gestures. A sensed gesture might be one of the gestures described elsewhere herein, along with pertinent data about the sensed gesture, such as the time of occurrence of the sensed gesture. The processor analyzes the sequence of sensed gestures to determine the start of a behavior event, such as the starting of an eating event.

The determination of the start of an eating event may be based on a sequence of sensed gestures, but it may also be based on the detection of a single event (possibly with non-gesture based context). For example, if the system detects a bite gesture with a reasonably high confidence level, the processor might consider that detection of that individual gesture to be the start of an eating event. The processor can also analyze the sequence of sensed gestures to determine the end of the behavior event. The determination of the end of an eating event may also be based on the absence of detected events. For example, if no bite gestures are detected in a given time period, the processor can assume that the eating event ended.

Knowing the start and end of a behavior event allows the processor to more accurately determine the gestures, since they are taken in context and/or the processor may enable additional sensors or place one or more sensors or other components in a higher performance state, such as in examples described elsewhere herein. Knowing the start and end of a behavior event also allows for power savings as, in some cases, it may be possible to place the worn device in a lower power mode outside certain behavior events. Also, aggregation of individual gestures into events, possibly combined with prior recorded data about similar behavior events from the same user or from other users in the past, allows the processor to derive meaningful characteristics about the behavior event. For example, an eating pace during breakfast, lunch, dinner can be determined in this manner. As another example, if the processor has a state for a current behavior and that current behavior is teeth brushing, gestures that might appear to be eating or drinking gestures would not be interpreted as eating or drinking gestures and thus not interpret sipping while teeth brushing as being consumption of liquids. Behavior events might be general events (eating, walking, brushing teeth, etc.) or more specific (eating with a spoon, eating with a fork, drinking from a glass, drinking from a can, etc.).

While it might be possible to decode an indirect gesture, such as detecting a pointing gesture and then determining the object that the sensed person is pointing at, of interest are gestures that themselves are directly part of the event being detected. Some gestures are incidental gestures, such as gestures associated with operating the device, in which case incidental gestures might be excluded from consideration.

In a specific example, the system uses some set of sensors to determine the start of an eating event with some confidence level and if the confidence level is higher than a threshold, the system activates additional sensors. Thus, the accelerometer sensor might be used to determine the start of an eating event with high confidence level, but a gyroscope is put in a low power mode to conserve battery life. The accelerometer alone can detect a gesture that is indicative of a probable bite or sip (e.g., an upward arm or hand movement or a hand or arm movement that is generally in the direction of the mouth), or a gesture that is generally indicative of the start of an eating event. Upon detection of a first gesture that is generally indicative of a possible start of an eating event, the additional sensors (e.g., gyroscope, etc.) may then be enabled. If a subsequent bite or sip gesture is detected, the processor determines that the start of an eating event had occurred and with a higher confidence level.

Event Detection

Knowing the start/end of a behavior event allows the processor to place one or more sensor or other components in a higher performance state for the duration of the behavior event. For example, when a start of a behavior event has been determined, the processor may increase the sampling rate of the accelerometer and/or gyroscope sensors used to detect gestures. As another example, when a start of a behavior event has been determined, the processor may increase the update rate at which sensor data are sent to electronic device 219 for further processing to reduce latency.

Referring again to FIG. 1, in addition to the tracking and processing subsystem, the system of FIG. 1 may also include a non-real-time analysis and learning subsystem 105. The non-real-time analysis and learning subsystem 105 can perform an analysis on larger datasets that take a longer time to collect, such as historical data across multiple food intake events and/or data from a larger population. Methods used by the non-real-time analysis and learning subsystem 105 may include, but are not limited to, data manipulation, algebraic computation, geo-tagging, statistical computing, machine learning and data analytics, computer vision, speech recognition, pattern recognition, compression and filtering.

Methods used by non-real-time analysis and learning subsystem 105 may, among other things, include data analytics on larger sets of data collected over longer periods of time. As an example, one or more data inputs may be captured over a longer period of time and across multiple food intake events to train a machine learning model. Such data inputs are hereafter referred to as training data sets. It is usually desirable that the period of time over which a training data set is collected, hereafter referred to as the training period, is sufficiently long such that the collected data is representative of a person's typical food intake.

A training data set may, among other things, include one or more of the following food intake related information: number of bites per food intake event, total bites count, duration of food intake event, pace of food intake or time between subsequent counts, categorization of food intake content such as for example distinguishing solid foods from liquids or sit-down meals from snacks or finger-foods. This information may be derived from one or more sensor inputs.

A training data set may furthermore include images of each or most items that were consumed during each of the food intake events within the training period. The images may be processed using computer vision and/or other methods to identify food categories, specific food items and estimate portion sizes. This information may then in turn be used to quantify the number of calories and/or the macronutrient content of the food items such as amounts of carbohydrates, fat, protein, etc.

In case the food was not consumed in its entirety, it may be desirable to take one picture of the food item at the start of the food intake event and one picture at the end of the food intake event to derive the portion of the food that was actually consumed. Other methods including, but not limited to, manual user input, may be used to add portion size information to the data in a training data set.

A training data set may furthermore include meta-data that do not directly quantify the food intake and/or eating behavior and patterns, but that may indirectly provide information, may correlate with food intake events and/or eating behavior and/or may be triggers for the occurrence of a food intake event or may influence eating habits, patterns and behavior. Such meta-data may, among other things, include one or more of the following: gender, age, weight, social-economic status, timing information about the food intake event such as date, time of day, day of week, information about location of food intake event, vital signs information, hydration level information, and other physical, mental or environmental conditions such as for example hunger, stress, sleep, fatigue level, addiction, illness, social pressure, and exercise.

One or more training data sets may be used to train one or more machine learning models which may then be used by one or more components of the dietary tracking and feedback systems to predict certain aspects of a food intake event and eating patterns and behaviors.

In one example, a model may be trained to predict the occurrence of a food intake event based on the tracking of one or more meta-data that may influence the occurrence of a food intake event. Other characteristics related to the probable food intake event, such as the type and/or amount of food that will likely be consumed, the pace at which a person will likely be eating, the duration of the food intake event, and/or the level of satisfaction a person will have from consuming the food may also be predicted. Meta-data may, among other things, include one or more of the following: gender, age, weight, social-economic status, timing information about the food intake event such as date, time of day, day of week, information about location of food intake event, vital signs information, hydration level information, and other physical, mental or environmental conditions such as for example hunger, stress, sleep, fatigue level, addiction, illness, social pressure, and exercise.

In another example, machine learning and data analytics may be applied to derive metrics that may be used outside the training period to estimate caloric or other macronutrient intake, even if only limited or no food intake sensor inputs or images are available. Meta-data may be used to further tailor the value of such metrics based on additional contextual information. Meta-data may, among other things, include one or more of the following: gender, age, weight, social-economic status, timing information about the food intake event such as date, time of day, day of week, information about location of food intake event, information about generic food category, vital signs information, hydration level information, calendar events information, phone call logs, email logs, and other physical, mental or environmental conditions such as for example hunger, stress, sleep, fatigue level, addiction, illness, social pressure, and exercise.

One example of such a metric would be "Calories per Bite". By combining the bites count with the caloric information obtained from image processing and analysis, a "Calories per bite" metric can be established from one or more training data sets. This metric can then be used outside the training period to estimate caloric intake based on bites count only, even if no images or only limited images are available.

Another metric could be "Typical Bite Size". By combining the bites count with the portion size information obtained from image processing and analysis, a "Typical Bite size" metric can be established from one or more training data sets. This metric can then be used outside the training period to estimate portion sizes based on bites count only, even if no images or only limited images are available. It may also be used to identify discrepancies between reported food intake and measured food intake based on bite count and typical bite size. A discrepancy may indicate that a user is not reporting all the food items that he or she is consuming. Or, alternatively, it may indicate that a user did not consume all the food that he or she reported.

Bite actions might be determined by a processor reading accelerometer and gyroscope sensors, or more generally by reading motion sensors that sense movement of body parts of the wearer. Then, by counting bites, a total number of bites can be inferred. Also, the time sequence of the bites can be used by the processor do deduce an eating pattern.

Non-real-time analysis and learning subsystem 105 may also be used track, analyze and help visualize larger sets of historical data, track progress against specific fixed or configured goals, and help establish such goals. It may furthermore be used to identify and track records, streaks and compare performance with that of friends or larger, optionally anonymous, populations.

Furthermore, in certain embodiments, non-real-time analysis and learning subsystem 105 may among other data manipulation and processing techniques, apply machine learning and data analytics techniques to predict the imminence of or the likelihood of developing certain health issues, diseases and other medical conditions. In this case, training typically requires historical food intake and/or eating behaviors data captured over longer periods of time and across a larger population. It is furthermore desirable that training data sets include additional meta-data such as age, weight, gender, geographical information, socio-economic status, vital signs, medical records information, calendar information, phone call logs, email logs and/or other information. Predictions may in turn be used to help steer health outcomes and/or prevent or delay the onset of certain diseases such as, for example, diabetes.

Non-real-time and learning subsystem 105 may also be used to learn and extract more information about other aspects including, but not limited to, one or more of the following: a user's dietary and food preferences, a user's dining preferences, a user's restaurant preferences, and a user's food consumption. Such information may be used by the food intake tracking and feedback system to make specific recommendations to user. The food intake tracking and feedback system described in herein may also interface to or be integrated with other systems such as restaurant reservation systems online food or meal ordering systems, and others to facilitate, streamline or automate the process of food or meal ordering or reservations.

Non-real-time and learning subsystem 105 may also be used to monitor food intake over longer periods of times and detect any unusually long episodes of no food intake activity. Such episodes may, among other things, indicate that the user stopped using the device, intentional or unintentional tampering with the device, a functional defect of the device or a medical situation such as for example a fall or death or loss of consciousness of the user. Detection of unusually long episodes of no food intake activity may be used to send a notification or alert to the user, one or more of his caregivers, a monitoring system, an emergency response system, or to a third party who may have a direct or indirect interest in being informed about the occurrence of such episodes.

Another component of the system shown in FIG. 1 is the feedback subsystem 106. The feedback subsystem 106 provides one or more feedback signals to the user or to any other person to which such feedback information may be relevant. The feedback subsystem 106 may provide real-time or near real-time feedback related to a specific food intake event. Real-time or near real-time feedback generally refers to feedback given around the time of a food intake event. This may include feedback given during the food intake event, feedback given ahead of the start of a food intake event and feedback given sometime after the end of a food intake event. Alternatively, or additionally, the feedback subsystem may provide feedback to the user that is not directly linked to a specific food intake event.

Feedback methods used by the feedback subsystem may include, but are not limited to, haptic feedback whereby a haptic interface is used that applies forces, vibrations and/or motion to the user, audio feedback where a speaker or any other audio interfaces may be used, or visual feedback whereby a display, one or more LEDs and/or projected light patterns may be used. The feedback subsystem may use only one or a combination of more than one feedback method.

The feedback subsystem may be implemented in hardware, in software or in a combination of hardware and software. The feedback subsystem may be implemented on the same device as the food intake event detection subsystem 101 and/or the tracking and processing subsystem 103. Alternatively, the feedback subsystem may be implemented in a device that is separate from the food intake event detection subsystem 101 and/or the tracking and processing subsystem 103. The feedback subsystem 106 may also be distributed across multiple devices, some of which may optionally house portions of some of the other subsystems illustrated in FIG. 1.

In one embodiment, the feedback subsystem 106 may provide feedback to the user to signal the actual, probable or imminent start of a food intake event. The feedback subsystem 106 may also provide feedback to the user during a food intake event to remind the user of the fact that a food intake event is taking place, to improve in-the-moment awareness and/or to encourage mindful eating. The feedback subsystem may also provide guidance on recommended portion sizes and/or food content, or provide alternative suggestions to eating. Alternative suggestions may be default suggestions or it may be custom suggestions that have been programmed or configured by the user at a different time.

Feedback signals may include, but are not limited to, periodic haptic feedback signals on a wearable device, sound alarms, display messages, or one or more notifications being pushed to his or her mobile phone display.

Upon receiving a signal that indicates the start of a food intake event, or sometime thereafter, the user may confirm that a food intake event is indeed taking place. Confirmation can be used to for example trigger logging of the event or may cause the system to prompt the user for additional information.

In another embodiment of the present disclosure, the feedback subsystem initiates feedback during a food intake event only if a certain threshold of one or more of the parameters being tracked is reached. As an example, if the time between subsequent bites or sips is being tracked, feedback to the user may be initiated if the time, possibly averaged over a multiple bites or sips, is shorter than a fixed or programmed value to encourage the user to slow down. Similarly, feedback may be initiated if a fixed or programmed bites or sips count is being exceeded.

In feedback subsystems where feedback is provided during a food intake event, the feedback provided by the feedback subsystem usually relates to specifics of that particular food intake event. However, other information including, but not limited to, information related to prior food intake events, biometric information, mental health information, activity or fitness level information, and environmental information may also be provided by the feedback subsystem.

In yet another embodiment of the present disclosure, the feedback subsystem 106 may be sending one or more feedback signals outside a specific food intake event. In one example of such an embodiment, ambient temperature and/or other parameters that may influence hydration requirements or otherwise directly or indirectly measure hydration levels may be tracked. Such tracking may happen continuously or periodically, or otherwise independent from a specific food intake event. If one or more such parameters exceed a fixed or programmed threshold, a feedback signal may be sent to, for example, encourage him/her to take measures to improve hydration. The feedback subsystem 106 might evaluate its inputs and determine that a preferred time for sending feedback is not during a food intake event, but after the food intake event has ended. Some of the inputs to the feedback subsystem 106 might be from a food intake event, but some might be from other monitoring not directly measured as a result of the food intake event.

The decision to send a feedback signal may be independent of any food intake tracking, such as in the embodiment described in the previous paragraph. Alternatively, such a decision may be linked to food intake tracking across one or multiple food intake events. For example, in one embodiment of the current disclosure, the system described above could be modified to also track, either directly or indirectly, a person's intake of fluids. For different ambient temperature ranges, said embodiment could have pre-programmed fluid intake requirement thresholds. If for a measured ambient temperature, a person's intake of fluids, possibly tracked and accumulated over a certain period of time, is not meeting the threshold for said ambient temperature, the system may issue a feedback signal to advise said person to increase his or her levels of fluid intake.

Similarly, feedback signals or recommendations related to food intake may among other parameters, be linked to tracking of activity levels, sleep levels, social context or circumstances, health or disease diagnostics, and health or disease monitoring.

In yet another embodiment of the current disclosure, the feedback subsystem 106 may initiate a feedback signal when it has detected that a food intake event has started or is imminent or likely. In such an embodiment, feedback could for example be used as a cue to remind the user log the food intake event or certain aspects of the food intake event that cannot be tracked automatically, or to influence or steer a person's food intake behavior and/or the amount or content of the food being consumed.

Information provided by the feedback subsystem 106 may include but is not limited to information related to eating patterns or habits, information related to specific edible substances, such as for example the name, the description, the nutrient content, reviews, ratings and/or images of food items or dishes, information related to triggers for food intake, information related to triggers for eating patterns or habits, biometric or environmental information, or other information that may be relevant either directly or indirectly to a person's general food intake behavior, health and/or wellness.

The feedback subsystem 106 may include the display of images of food items or dishes that have been consumed or may be consumed. Furthermore, the feedback subsystem 106 may include additional information on said food items or dishes, such as for example indication of how healthy they are, nutrient content, backstories or preparation details, ratings, personalized feedback or other personalized information.

In certain embodiments of the current disclosure, the information provided by the feedback subsystem 106 may include non-real-time information. The feedback subsystem 106 may for example include feedback that is based on processing and analysis of historical data and/or the processing and analysis of data that has been accumulated over a larger population of users. The feedback subsystem 106 may further provide feedback that is independent of the tracking of any specific parameters. As an example, the feedback subsystem 106 may provide generic food, nutrition or health information or guidance.

In certain embodiments of the current disclosure, the user may interact with the feedback subsystem 106 and provide inputs 116. For example, a user may suppress or customize certain or all feedback signals.

Non-real time feedback may, among other things, include historical data, overview of trends, personal records, streaks, performance against goals or performance compared to friends or other people or groups of people, notifications of alarming trends, feedback from friends, social networks and social media, caregivers, nutritionists, physicians etc., coaching advice and guidance.

Data or other information may be stored in data storage unit 104. It may be stored in raw format. Alternatively, it may be stored after it has been subject to some level of processing. Data may be stored temporarily or permanently. Data or other information may be stored for a wide variety of reasons including, but not limited to, temporary storage while waiting for a processor or other system resources to become available, temporary storage to be combined with other data that may not be available until a later time, storage to be fed back to the user in raw or processed format through the feedback subsystem 106, storage for later consultation or review, storage for analysis for dietary and/or wellness coaching purposes, storage for statistical analysis across a larger population or on larger datasets, storage to perform pattern recognition methods or machine learning techniques on larger datasets.

The stored data and information, or portions thereof, may be accessible to the user of the system. It is also possible that the stored data and information or portions thereof, may be shared with or can be accessed by a third party. Third parties may include, but are not limited to, friends, family members, caregivers, healthcare providers, nutritionists, wellness coaches, other users, companies that develop and/or sell systems for dietary tracking and coaching, companies that develop and/or sell components or subsystems for systems for dietary tracking and coaching, and insurance companies. In certain circumstances, it may be desirable that data is made anonymous before making it available to a third party.

Figure 2:
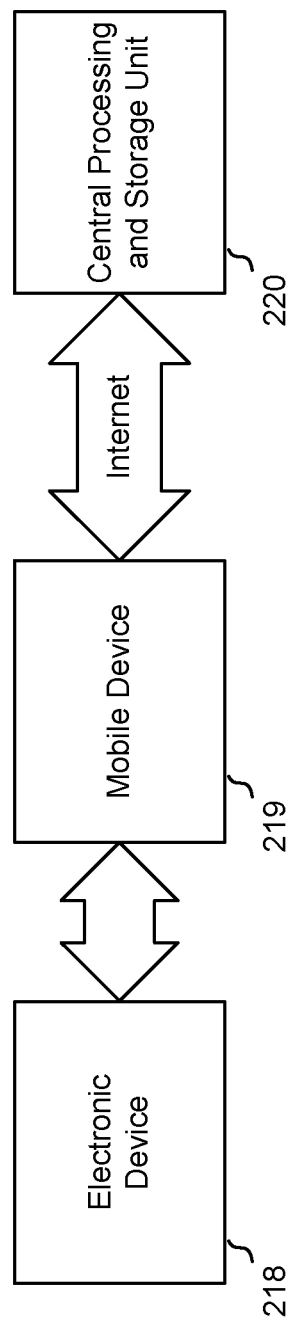
FIG. 2 illustrates a process to provide for user intervention.

FIG. 2 illustrates some of the components disposed in an electronic system used for dietary tracking and coaching, in accordance with one embodiment of the present disclosure. The electronic system includes a first electronic device 218, a second electronic device 219 (which may be a mobile device), and a central processing and storage unit 220. A typical system might have a calibration functionality, to allow for sensor and processor calibration.

Variations of the system shown in FIG. 2 are also possible and are included in the scope of the present disclosure. For example, in one variation, electronic device 218 and electronic device 219 may be combined into a single electronic device. In another variation, the functionality of electronic device 218 may be distributed across multiple devices. In some variations, a portion of the functionality shown in FIG. 2 as being part of electronic device 218 may instead be included in electronic device 219. In some other variations, a portion of the functionality shown in FIG. 2 as being part of electronic device 219 may instead be included in electronic device 218 and/or central processing and storage unit 220. In yet another variation, the central processing and storage unit 220 may not be present and all processing and storage may be done locally on electronic device 218 and/or electronic device 219. Other variations are also possible.

Figure 3:
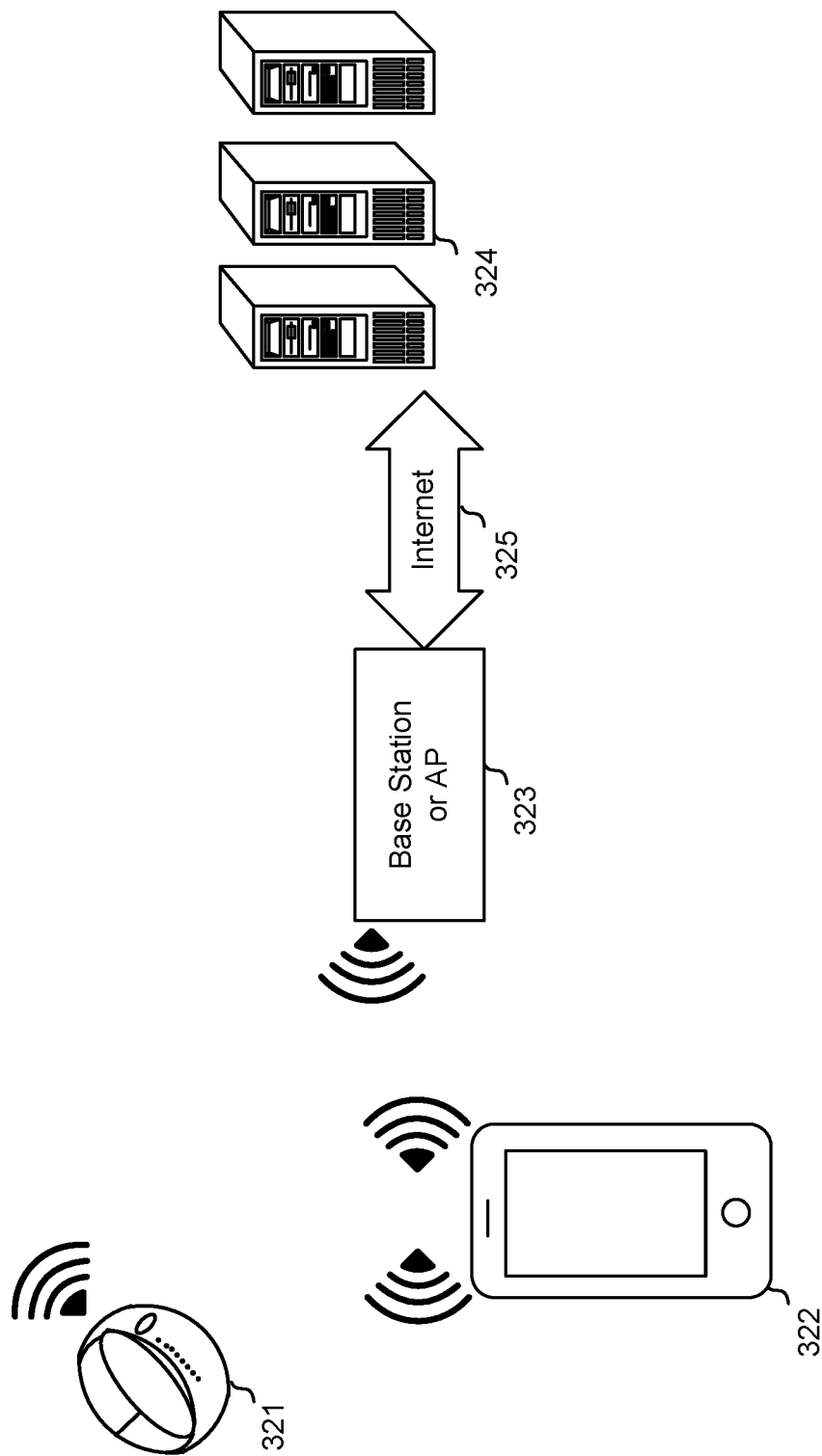
FIG. 3 is an illustrative example of an environment in accordance with at least one embodiment.

An example of the electronic system of FIG. 2 is shown in FIG. 3. Electronic device 218 may for example be a wearable device 321 that is worn around the wrist, arm or finger. Electronic device 218 may also be implemented as a wearable patch that may be attached to the body or may be embedded in clothing. Electronic device 218 may also be a module or add-on device that can for example be attached to another wearable device, to jewelry, or to clothing. Electronic device 219 may for example be a mobile device 322 such as a mobile phone, a tablet or a smart watch. Other embodiments of electronic device 219 and of electronic device 218 are also possible. The central processing and storage unit 220 usually comprises of one or more computer systems or servers and one or more storage systems. The central processing and storage unit 220 may for example be a remote datacenter 324 that is accessible via the Internet using an Internet connection 325. The central processing and storage unit 220 is often times shared among and/or accessed by multiple users.

The wearable device 321 may communicate with mobile device 322 over a wireless network. Wireless protocols used for communication over a wireless network between wearable device 321 and mobile device 322 may include, but is not limited to, Bluetooth, Bluetooth Smart (a.k.a. Bluetooth Low Energy), Bluetooth Mesh, ZigBee, Wi-Fi, Wi-Fi Direct, NFC, Cellular and Thread. A proprietary or wireless protocol, modifications of a standardized wireless protocol or other standardized wireless protocols may also be used. In another embodiment of the current disclosure, the wearable device 321 and the mobile device 322 may communicate over a wired network.

The mobile device 322 may communicate wirelessly with a base station or Access Point ("AP") 323 that is connected to the Internet via Internet connection 325. Via the Internet connection 325, mobile device 322 may transfer data and information from wearable device 321 to one or more central processing and storage unit 220 that reside at a remote location, such as for example a remote data center. Via Internet connection 325, mobile device 322 may also transfer data and information from one or more central processing and storage unit 220 that reside at a remote location to wearable device 321. Other examples are also possible. In some embodiments, the central processing and storage unit 220 may not be at a remote location, but may reside at the same location or close to the wearable device 321 and/or mobile device 322. Wireless protocols used for communication between the mobile device 322 and the base station or access point 323 may be the same as those between the mobile device and the wearable device. A proprietary or wireless protocol, modifications of a standardized wireless protocol or other standardized wireless protocols may also be used.

Figure 4:
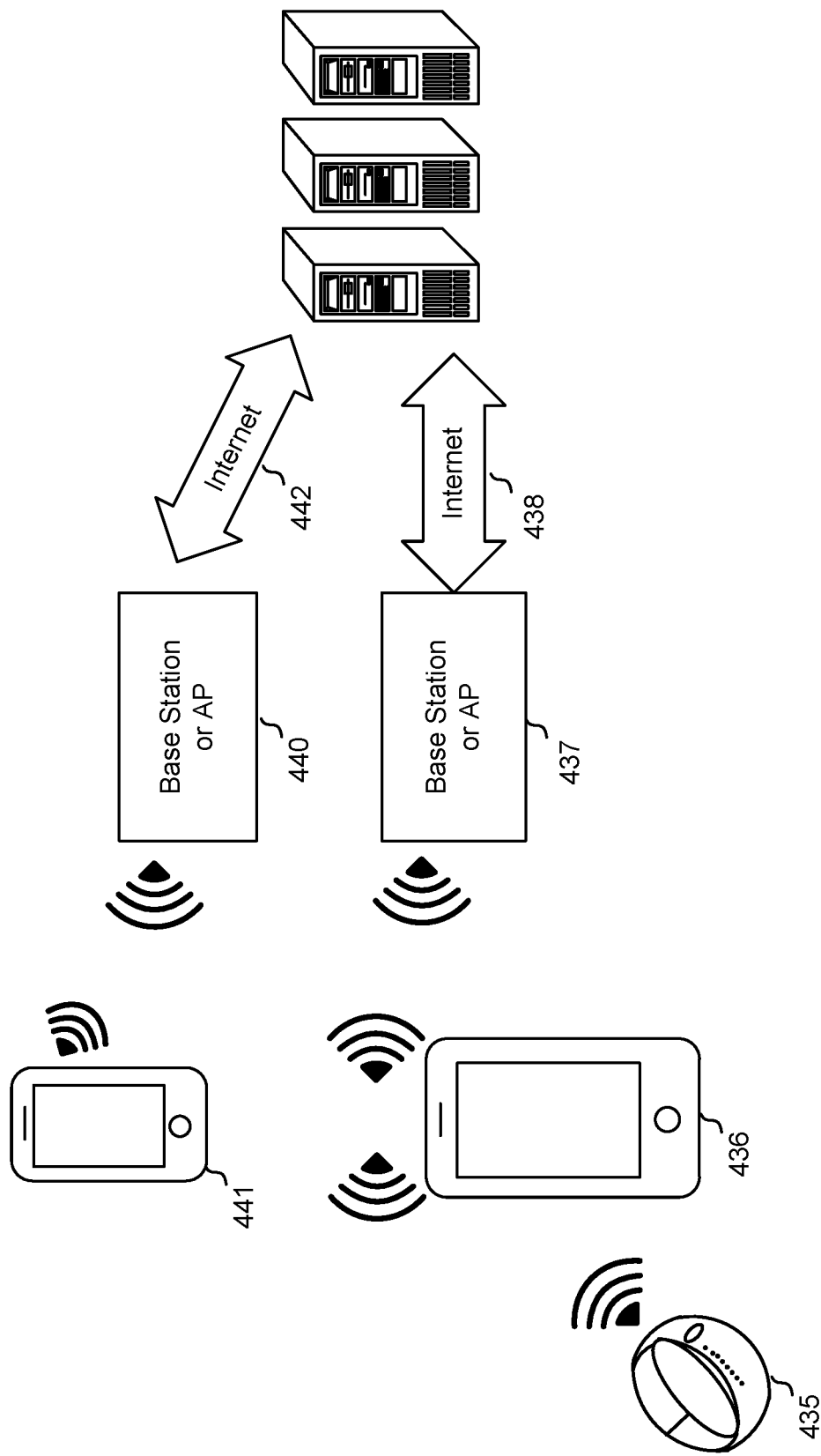
FIG. 4 is an illustrative example of an environment that includes communication with at least one additional device over the internet in accordance with at least one embodiment.

The electronic system of FIG. 2 may also send data, information, notifications and/or instructions to and/or receive data, information, notifications and/or instructions from additional devices that are connected to the Internet. Such devices could for example be a tablet, mobile phone, laptop or computer of one or more caregivers, members of the physician's office, coaches, family members, friends, people whom the user has connected with on social media, or other people to whom the user has given the authorization to share information. One example of such a system is shown in FIG. 4. In the example shown in FIG. 4, electronic device 441 is wirelessly connected to base station or Access Point 440 that is connected to the Internet via Internet connection 442. Examples of electronic device 441 may include, but are not limited to, a tablet, mobile phone, laptop, computer, or smart watch. Via Internet connection 442, electronic device 441 may receive data, instructions, notifications or other information from one or more central processing and storage units that may reside locally or at a remote location, such as for example a remote data center. The communication capability can include Internet connection 442 or other communication channels. Electronic device 441 may also send information, instructions or notifications to one or more computer servers or storage units 439. Central processing and storage unit 439 may forward this information, instructions or notifications to a mobile device 436 via the Internet 438 and the base station or Access Point ("AP") 437.

Other examples are also possible. In some embodiments, the central processing and storage unit 439 may not be at a remote location, but may reside at the same location or close to the wearable device 435 and/or mobile device 436. FIG. 4 shows electronic device 441 as being wirelessly connected to the base station or Access Point. A wired connection between electronic device 441 and a router that connects to the Internet via an Internet connection 442 is also possible.

Figure 5:
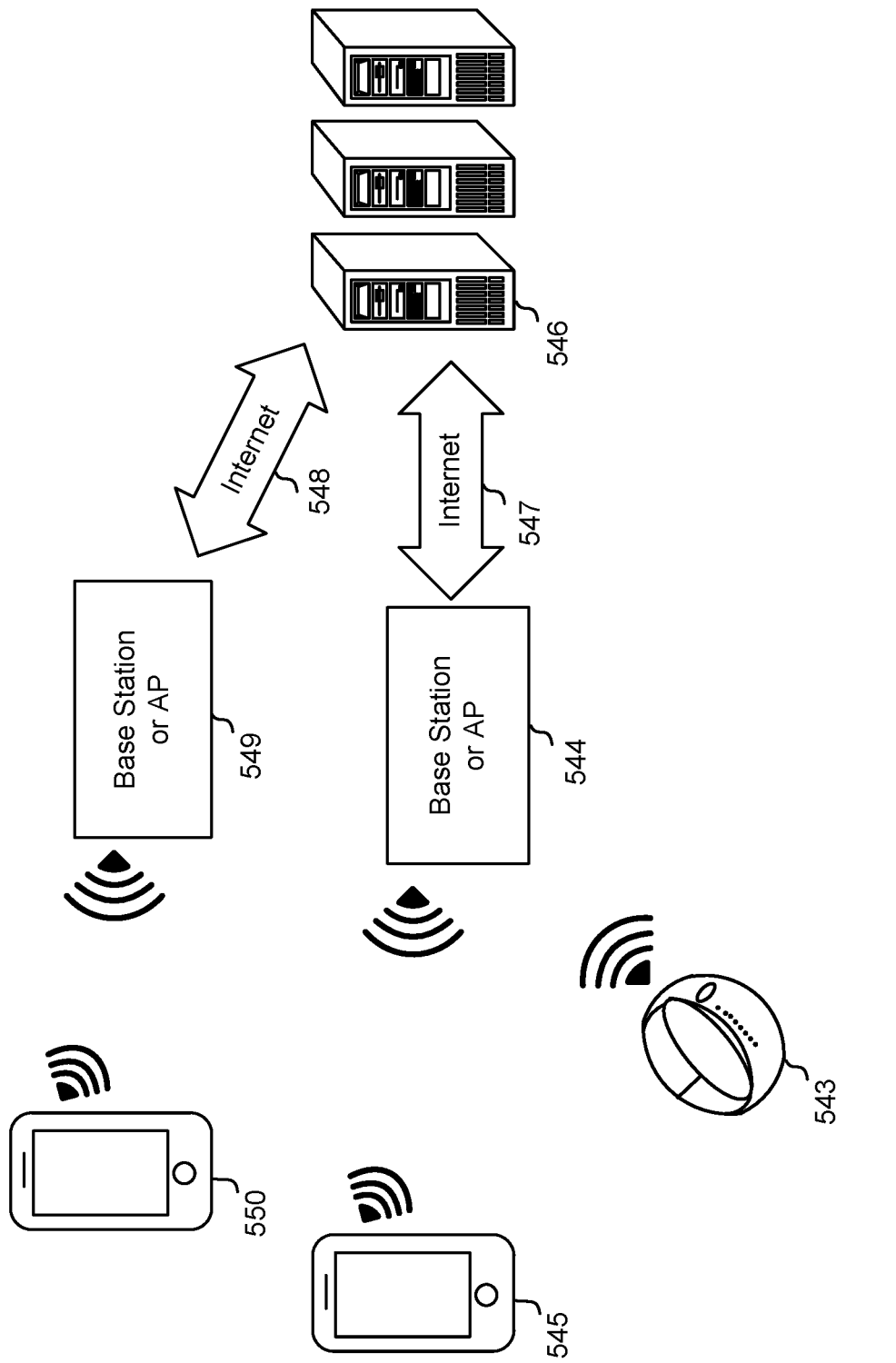
FIG. 5 is an illustrative example of an environment where a food intake monitoring and tracking device communicates directly with a base station or an access point in accordance with at least one embodiment.

FIG. 5 illustrates another embodiment of the present disclosure. In FIG. 5, a wearable device 543 can exchange data or other information directly with a central processing and storage system 546 via a base station or Access Point 544 and the Internet without having to go through a mobile device 545. Mobile device 545 may exchange data or other information with wearable device 543 either via central processing and storage system 546 or via a local wireless or wired network. The central processing and storage system 546 may exchange information with one or more additional electronic devices 550.

Figure 6:
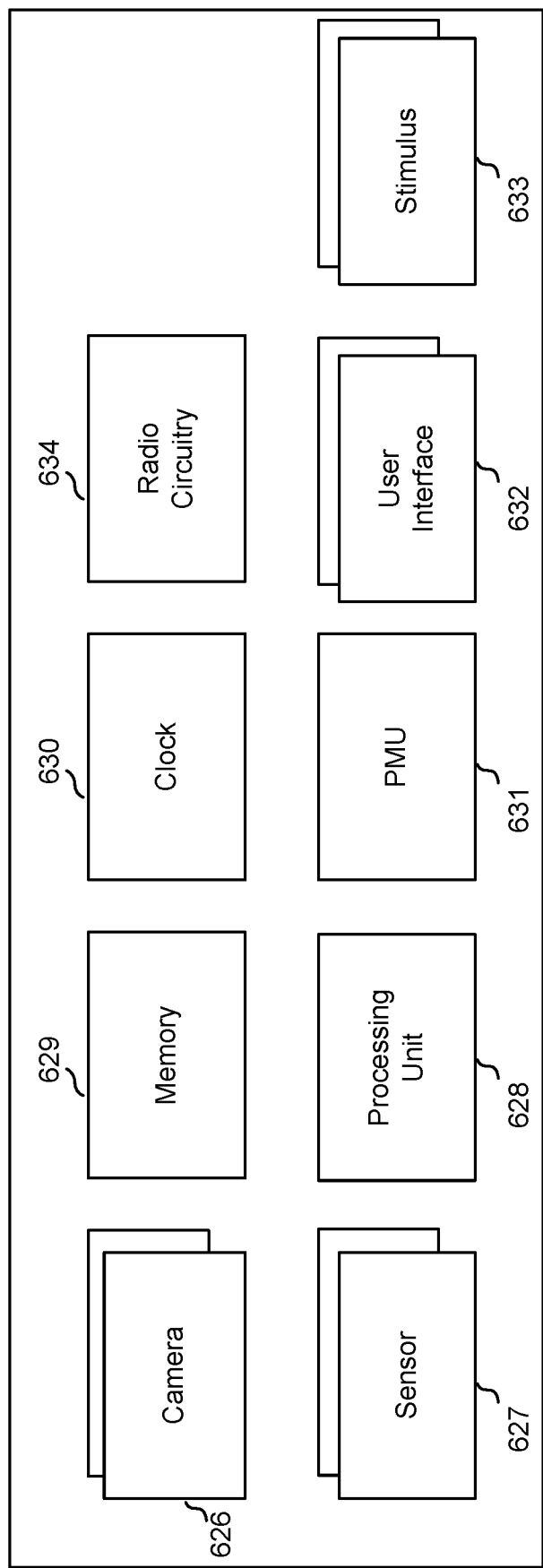
FIG. 6 is an illustrative example of a high-level block diagram of a monitoring and tracking device in accordance with at least one embodiment.

FIG. 6 illustrates some of the components disposed in electronic device 218, in accordance with one embodiment. Electronic device 218 typically includes, in part, one or more sensor units 627, a processing unit 628, memory 629 that can include or be realized as computer-readable storage media having program code instructions, a clock or crystal 630, radio circuitry 634, and a power management unit ("PMU") 631. Electronic device 218 may also include one or more camera modules 626, one or more stimulus units 633 and one or more user interfaces 632. Although not shown, other components like capacitors, resistors, inductors may also be included in said electronic device 218. Power Management unit 631 may, among other things, include one or more of the following: battery, charging circuitry, regulators, hardware to disable the power to one or more components, power plug.

In many embodiments, electronic device 218 is a size constrained, power-sensitive battery operated device with a simple and limited user interface. Where power is limited, electronic device 218 might be programmed to save power outside of behavior events. For example, a processor in electronic device 218 might be programmed to determine the start of a behavior event, such as an eating event, and then power up additional sensors, place certain sensors in a higher performance mode and/or perform additional computations until the processor determines an end of the behavior event, at which point the processor might turn off the additional sensors, place certain sensors back in a lower performance mode and omit the additional computations.

For example, the processor might be programmed to disable all motion-detection related circuitry, with exception of an accelerometer. The processor could then monitor accelerometer sensor data and if those data indicate an actual or prominent food intake activity such as a bite or sip gesture, then the processor could activate additional circuitry, such as a data recording mechanism. The processor might use the accelerometer sensor data to monitor a pitch of the wearer's arm.

For example, the processor might measure pitch of the wearer's arm until the pitch exceeds a certain threshold, perhaps one indicative of a hand or arm movement towards the wearers' mouth. Once that is detected, the processor can change the state (such as by changing a memory location set aside for this state from "inactive" or "out-of-event" to "in an action" or "in-event") and activate additional circuitry or activate a higher performance mode of specific circuitry or components. In another embodiment, other accelerometer sensor data characteristics such as first integral of acceleration (velocity) or the second integral of acceleration (distance traveled), or characteristics related to or derived from the first and/or second integral of acceleration might be used, as determined from one or more accelerometer axis. A machine learning process might be used to detect specific movements and translate those to gestures.

An end of a food intake event might be detected by the processor by considering whether a certain time has expired since a last bite or sip movement or when other data (metadata about the wearer, motion-detection sensor data, and/or historical data of the wearer, or a combination of those). Based on those, the processor makes a determination that a food intake event is not likely and then changes the state of the electronic device to an inactive monitoring state, possibly a lower power mode.

The lower power mode might be implemented by the processor reducing the sampling rate of the accelerometer and/or gyroscope, powering down the gyroscope, reducing the update rate at which sensor data is transferred from the electronic device (such as electronic device 218) to the support device (such as electronic device 219), compressing the data before transferring the data from the sensing electronic device to the support electronic device.

In some embodiments of the present disclosure, some of the components that are shown in FIG. 5 as separate components may be combined. As an example, the processing unit, memory, radio circuitry and PMU functionality may entirely or in part be combined in a single wireless microcontroller unit ("MCU"). Other combinations are also possible. Similarly, components that are shown as a single component in FIG. 5 may be implemented as multiple components. As an example, the processing functionality may be distributed across multiple processors. Likewise, data storage functionality may be distributed across multiple memory components. Other examples of distributed implementations are also possible.

In another embodiment of the present disclosure, the radio circuitry may not be present and instead a different interface (such as for example a USB interface and cable) may be used to transfer data or information to and/or from the electronic device 218.

Stimulus unit 633 may provide feedback to the user of the electronic device. A stimulus unit 633 may include but is not limited to a haptic interface that applies forces, vibrations or motions to the user, a speaker or headphones interface that provides sounds to the user, and a display that provides visual feedback to the user.

In certain embodiments, the processing and analysis of signals from sensors embedded in electronic device 218 can detect when electronic device has been disabled, tampered with, removed from the body or is not being used. This can be used to conserve power, or to send a notification to the user, a friend or another person who might directly or indirectly have an interest in being notified if electronic device 218 is not being used properly.

Description Detection/Prediction of Start/End of Food Intake Event

In a preferred embodiment, the electronic device 218 is worn around the wrist, arm or finger and has one or more sensors that generate data necessary to detect the start and/or end of a food intake event. The electronic device 218 may also be integrated in a patch that can be attached to a person's arm or wrist. The electronic device 218 may also be a module or add-on device that can be attached to another device that is worn around the wrist, arm or finger. Sensors used to detect the start and/or end of a food intake event may, among other sensors, include one or more of the sensors described herein.

The raw sensor outputs may be stored locally in memory 629 and processed locally on processing unit 628 to detect if the start or end of a food intake event has occurred. Alternatively, one or more sensor outputs may be sent to electronic device 219 and/or the central processing and storage unit 220, either in raw or processed format, for further processing and to detect if the start or end of a food intake event has occurred. Regardless of where the processing for food intake detection occurs, sensor outputs in raw or processed format may be stored inside electronic device 218, inside electronic device 219 and/or inside the central processing and storage unit 220.

The sensor or sensors that generate data necessary for the detection of the start and/or end of a food intake event may be internal to electronic device 218. Alternatively, one or more of the sensors responsible for the detection of the start of a food intake event may be external to electronic device 218, but are able to relay relevant information to the electronic device 218 either directly through direct wireless or wired, communication with electronic device 218 or indirectly, through another device. It is also possible that electronic device 218 and the external sensor or sensors are able to relay information to electronic device 219, but are not able to relay information to one another directly.

In case of indirect communication through another device such as a mobile phone or other portable or stationary device, such third device is able to receive data or information from one or more external sensor units, optionally processes such data or information, and forwards either the raw or processed data or information to electronic device 218. The communication to and from the electronic device 218 may be wired or wireless, or a combination of both.

Examples of sensors that may be external to electronic device 218 may be one or more sensors embedded in a necklace or pendant worn around the neck, one or more sensors embedded in patches that are attached to a different location on the body, one or more sensors embedded in a supplemental second wearable device that is worn around the other arm or wrist or on a finger of the other hand, or one or more sensors integrated in a tooth. In some embodiments, the electronic device is worn on one hand or arm but detects movement of the other hand or arm. In some embodiments, electronic devices are worn on each hand.

Information obtained from the non-real-time analysis and learning subsystem 105 may also be used, optionally in combination with information from one or more sensors 627, to predict or facilitate the detection of a probable, imminent or actual start/end of a food intake event.

It is often desirable that the detection and/or the prediction of the start and/or end of a food intake event happens autonomously without requiring user intervention. For example, if the actual, probable or imminent start of a food intake event is predicted or detected autonomously, this information can be used as a trigger to activate or power up specific components or circuits that are only needed during a food intake event. This can help conserve power and extend the battery life of electronic device 218. The prediction or detection of an actual, probable or imminent start of a food intake event can also be used to issue a cue or reminder to the user. A cue can for example be sent to the user to remind him/her to take further actions including, but not limited to, logging the food intake event or taking a picture of the food. Upon detection of the start of a food intake event, one or more cues, possibly spread out over the duration of the food intake event, to remind the user that a food intake event is taking place and improving in-the-moment awareness and/or encourage mindful eating. Cues or reminders may for example be sent through discrete haptic feedback using one or more stimulus units 633. Other methods using one or more user interfaces 632, such as for example one or more LEDs, a display message, or an audio signal, are also possible. Alternatively, a mobile device may be used to communicate cues, reminders or other information such as for example portion size recommendations or alternative suggestions to eating to the user.

If the actual, probable or imminent end of a food intake event is predicted or detected autonomously, this information can be used as a trigger to power down or at least put in a lower power mode one or more circuits or components of an electronic device that are only needed during a food intake event. This can help conserve power and extend the battery life of the electronic device. The detection of the actual, probable or imminent end of a food intake event may also be used to modify or suspend the feedback provided to the user by one or more stimulus units 633, by one or more of the user interfaces 632, and/or by the mobile device.

In some embodiments of the present disclosure, the detection or prediction of the actual, probable or imminent start and/or end of a food intake event may not be entirely autonomously. For example, the user may be required to make a specific arm, wrist, hand or finger gesture to signal to the electronic device the actual, probable or imminent start and/or end of a food intake event. The arm, wrist, hand or finger gesture is then detected by one or more sensors inside the electronic device. It is usually desirable that the arm, wrist, hand or finger gesture or gestures required to indicate the start and/or end of a food intake event can be performed in a subtle and discrete way. Other methods may also be used. For example, the user may be asked to push a button on the electronic device to indicate the start and/or end of a food intake event. Voice activation commands using a microphone that is built into the electronic device may also be used. Other methods are also possible.

Description of Tracking of Eating Behaviors and Patterns

In a particular embodiment, the electronic device is worn around the wrist, arm or finger and has one or more sensors that generate data that facilitate the measurement and analysis of eating behaviors, patterns and habits. Sensors used for measuring and analyzing certain eating behaviors and patterns may include one or more of the sensors described herein.

Relevant metrics that may be used to quantify and track eating behaviors and eating patterns may include, but are not limited to, the time between subsequent bites or sips, the distance between the plate and the user's mouth, the speed of arm movement towards and/or away from the user's mouth, and the number of bites or sips during a single food intake event, derived from the total count of arm movements corresponding to a bite or sip, specific chewing behavior and characteristics, the time between taking a bite and swallowing, amount of chewing prior to swallowing.

FIG. 6 illustrates examples of components of such an electronic device. As illustrated, the raw sensor outputs may be stored locally in a memory 629 and processed locally on a processing unit 628. Alternatively, one or more sensor outputs may be sent to the electronic device and/or a processing unit 628, either in raw or in processed format, for further processing and analysis. Regardless of where the processing and analysis of eating behaviors and patterns occurs, sensor outputs in raw or processed format may be stored inside the electronic device, inside an ancillary electronic device, such as a mobile phone, and/or inside the processing unit 628.

In some embodiments, the generation, collection and/or processing of data that facilitate the measurement and analysis of eating behaviors, patterns and habits may be continuously, periodically or otherwise independently of the start and/or end of a food intake event. Alternatively, the generation, collection and/or processing of data that facilitate the measurement and analysis of eating behavior and patterns may occur only during a food intake event or be otherwise linked to a specific food intake event. It is also possible that some sensor data are being generated, collected and/or processed continuously, periodically or otherwise independently of the start and/or end of a food intake event whereas other sensor data are taken during a food intake event or otherwise linked to a food intake event.

The sensor or sensors that generate data necessary for measuring and analyzing eating behaviors and eating patterns may be internal to the electronic device. Alternatively, one or more of the sensors that generate data necessary for measuring and analyzing eating behaviors and eating patterns may be external to the electronic device, but are able to relay relevant information to the electronic device either directly through direct wireless or wired, communication with the electronic device or indirectly, through another device.

In case of indirect communication through another device such as a mobile phone or other portable or stationary device, such third device is able to receive data or information from the external sensor unit, optionally processes such data or information, and forwards either the raw or processed data or information to the tracking device. The communication to and from the electronic device may be wired or wireless, or a combination of both.

Examples of sensors that may be external to the electronic device may be one or more sensors embedded in a necklace or pendant worn around the neck, one or more sensors embedded in patches that are attached to a different location on the body, one or more sensors embedded in a supplemental second wearable device that is worn around the other arm or wrist or on a finger of the other hand, or one or more sensors integrated in a tooth.

Description of Use of Camera Module and Image Capture

While use of a camera to capture images of food have been proposed in the prior art, they typically rely on the user taking pictures with his or her mobile phone or tablet. Unfortunately, image capture using a mobile phone or tablet imposes significant friction of use, may not be socially acceptable in certain dining situations or may interfere with the authenticity of the dining experience. It is often times not desirable or inappropriate that the user needs to pull out his or her mobile phone, unlock the screen, open a mobile app and take a picture using the camera that is built into the mobile phone.

If user intervention is required, it is generally desirable that the user intervention can be performed in a subtle and discrete manner and with as little friction as possible. In order to minimize the friction of use, it is often times desirable that the image capture can be initiated from the electronic device directly.

While the examples provided herein use image capture of food and meal scenarios as examples, upon reading this disclosure, it should be clear that the methods and apparatus described herein can be applied to image capture of objects and scenes other than foods and meal scenarios. For example, a viewfinder-less camera can have application outside of the food event capture domain.

In some embodiments, the electronic device is worn around the wrist, arm or finger and includes one or more camera modules 626. One or more camera modules 626 may be used for the capture of still images in accordance with one embodiment of the present disclosure, and for the capture of one or more video streams in accordance with another embodiment of the present disclosure. In yet another embodiment of the present disclosure, a combination of still and streaming images is also possible.

One or more camera modules may also be included in a device that is worn at a different location around the body, such as a necklace or pendant that is worn around the neck, or a device that is attached to or integrated with the user's clothing, with the camera or camera modules preferably aiming towards the front so that it can be in line of sight with the food being consumed.

In some embodiments, activation of a camera module and/or image capture by a camera module may require some level of user intervention. User intervention may, among other things, include pressing a button, issuing a voice command into a microphone that is built into the electronic device or the mobile device, making a selection using a display integrated in the electronic device or the mobile device, issuing a specific arm, wrist, hand or finger gesture, directing the camera so that the object of interest is within view of the camera, removing obstacles that may be in the line of sight between the camera and the object of interest, and/or adjusting the position of the object of interest so that it is within view of the camera. Other user intervention methods, or a combination of multiple user intervention methods are also possible.

In one embodiment of the present disclosure, a camera module is built into an electronic device, such as a wearable device, that may not have a viewfinder, or may not have a display that can give feedback to the user about the area that is within view of the camera. In this case, the electronic device may include a light source that projects a pattern of visible light onto a surface or onto an object to indicate to the user the area that is within the view of the camera. One or more Light Emitting Diodes (LEDs) may be used as the light source. Other light sources including, but not limited to, laser, halogen or incandescent light sources are also possible. The pattern of visible light may, among other things, be used by the user to adjust the position of the camera, adjust the position the object of interest and/or remove any objects that are obstructing the line of sight between the object of interest and the camera.

The light source may also be used to communicate other information to the user. As an example, the electronic device may use inputs from one or more proximity sensors, process those inputs to determine if the camera is within the proper distance range from the object of interest, and use one or more light sources to communicate to the user that the camera is within the proper distance range, that the user needs to increase the distance between camera and the object of interest, or that the user needs to reduce the distance between the camera and the object of interest.

The light source may also be used in combination with an ambient light sensor to communicate to the user if the ambient light is insufficient or too strong for an adequate quality image capture.

The light source may also be used to communicate information including, but not limited, to a low battery situation or a functional defect.

The light source may also be used to communicate dietary coaching information. As an example, the light source might, among other things, indicate if not enough or too much time has expired since the previous food intake event, or may communicate to the user how he/she is doing against specific dietary goals.

Signaling mechanisms to convey specific messages using one or more light sources may include, but are not limited to, one or more of the following: specific light intensities or light intensity patterns, specific light colors or light color patterns, specific spatial or temporal light patterns. Multiple mechanisms may also be combined to signal one specific message.

In another embodiment of the current disclosure, a camera module may be built into an electronic device, such as a wearable device, that does not have a viewfinder or does not have a display that can give feedback to the user about the area that is within view of the camera. Instead of or in addition to using a light source, one or more images captured by the camera module, possibly combined with inputs from other sensors that are embedded in the electronic device may be sent to the processing unit inside the electronic device, the processing unit inside the mobile device, and/or the processing unit 628 for analysis and to determine if the object of interest is within proper view and/or proper focal range of the camera. The results of the analysis may be communicated to the user using one of the feedback mechanisms available in the electronic device including, but not limited to, haptic feedback, visual feedback using one or more LEDs or a display, and/or audio feedback.

In some other embodiments of the present disclosure, the electronic device may capture one or more images without any user intervention. The electronic device may continuously, periodically or otherwise independently of any food intake event capture still or streaming images. Alternatively, the electronic device may only activate one or more of its camera modules around or during the time of a food intake event. As an example, an electronic device may only activate one or more of its camera modules and capture one or more images after the start of a food intake event has been detected and before the end of a food intake event has been detected. It may use one or more of its camera modules to capture one of more images of food items or dishes in their entirety, or of a portion of one or more food items or dishes.

In some embodiments, one camera may be used to capture one or more images of food items that are on a plate, table or other stationary surface, and a second camera may be used to capture one or more images of food items that are being held by the user, such as for example finger foods or drinks. The use of more than one camera may be desirable in situations where no user intervention is desirable and the position, area of view or focal range of a single camera is not suite to capture all possible meal scenarios.

In one example embodiment, the position, the orientation and the angle of view of the camera are such that an image or video capture is possible without any user intervention. In such an embodiment, the wearable device may use a variety of techniques to determine the proper timing of the image or video stream capture such that it can capture the food or a portion of the food being consumed. It may also choose to capture multiple images or video streams for this purpose. Techniques to determine the proper timing may include, but are not limited to, the following: sensing of proximity, sensing of acceleration or motion (or absence thereof), location information. Such sensor information may be used by itself or in combination with pattern recognition or data analytics techniques (or a combination of both) to predict the best timing for the image or video capture. Techniques may include, but are not limited to, training of a model based on machine learning.

The captured still and/or streaming images usually require some level of processing. Processing may include but is not limited to compression, deletion, resizing, filtering, image editing, and computer vision techniques to identify objects such as for example specific foods or dishes, or features such as for example portion sizes. Processing units that may be used to process still or streaming images from the camera module or modules, regardless of whether or not the camera module or modules are internal to the electronic device, include, but are not limited to, the processing unit inside the electronic device, the processing unit inside a mobile device and/or a processing unit 628 which may reside at the same location as where the electronic device is being used or alternatively, may reside at a remote location (e.g., in a cloud server) in which case it may be accessed via the internet. The image processing may also be distributed among a combination of the abovementioned processing units.

Examples of local processing may include but are not limited to: selection of one or more still images out of multiple images or one or more video streams, compression of images or video stream, application of computer vision algorithms on one or more images or video streams.

Local processing may include compression. In case of compression, a compressed image may be transmitted as part of a time critical transaction whereas its non-compressed version may be saved for transmission at a later time.

One or more still or streaming images may be analyzed and/or compared for one or multiple purposes including, but not limited to, the detection of the start and/or end of a food intake event, the identification of food items, the identification of food content, the identification or derivation of nutritional information, the estimation of portion sizes and the inference of certain eating behaviors and eating patterns.

As one example, computer vision techniques, optionally combined with other image manipulation techniques may be used to identify food categories, specific food items and/or estimate portion sizes. Alternatively, images may be analyzed manually using a Mechanical Turk process or other crowdsourcing methods. Once the food categories and/or specific food items have been identified, this information can be used to retrieve nutritional information from one or more foods/nutrition databases.

As another example, information about a user's pace of eating or drinking may be inferred from analyzing and comparing multiple images captured at different times during the course of a food intake event. As yet another example, images, optionally combined with other sensor information, may be used to distinguish a sit-down meal from finger foods or snacks. As yet another example, the analysis of one image taken at the start of a food intake event and another image taken at the end of a food intake event may provide information on the amount of food that was actually consumed.

Description of User Feedback

In a preferred embodiment of the present disclosure, the electronic device 218 is worn around the wrist, arm or finger and has one or more stimulus units and/or user interfaces that allow for feedback to the user or the wearer of the electronic device. In a different embodiment of the present disclosure, electronic device 218 may be implemented as a wearable patch that may be attached to the body or may be embedded in clothing.

Feedback usually includes feedback that is food or food intake related. Feedback methods may include, but are not limited to, haptic feedback, visual feedback using LEDs or a display or audio feedback. In one such embodiment, electronic device 218 may have a haptic interface that vibrates once or multiple times when the start and/or end of a food intake event have been detected. In another embodiment, electronic device 218 may have a haptic interface that vibrates once or multiple times when the tracking and processing subsystem identifies that the wearer of the device is consuming food and is showing eating behavior that is exceeding certain programmed thresholds, such as for example eating too fast, too slow or too much. Alternatively, the haptic interface may vibrate one or more times during a food intake event, independent of any specific eating behavior, for example to remind the wearer of the fact that a food intake event is taking place and/or to improve in-the-moment awareness and to encourage mindful eating. Other feedback methods are also possible, and different metrics or criteria may be used to trigger an activation of such feedback methods.

In a different embodiment of the present disclosure, feedback is provided to the user through a device that is separate from the electronic device 218. One or more stimulus units and/or user interfaces required to provide feedback to the user may be external to electronic device 218. As an example, one or more stimulus units and/or user interfaces may be inside electronic device 219, and one or more of said stimulus units and/or user interfaces inside electronic device 219 may be used to provide feedback instead of or in addition to feedback provided by electronic device 218. Examples may include, but are not limited to, messages being shown on the display of electronic device 219, or sound alarms being issued by the audio subsystem embedded inside electronic device 219.

Alternatively, feedback may be provided through a device that is separate from both electronic device 218 and electronic device 219, but that is able to at a minimum, either directly or indirectly, receive data from at least one of those devices.

In addition to or instead of feedback provided around or during the time of a food intake event, the system of FIG. 2 or FIG. 3 may also provide feedback that may span multiple food intake events or may not be linked to a specific food intake event or set of food intake events. Examples of such feedback may include, but are not limited to, food content and nutritional information, historical data summaries, overviews of one or more tracked parameters over an extended period of time, progress of one or more tracked parameters, personalized dietary coaching and advice, benchmarking of one or more tracked parameters against peers or other users with similar profile.

DETAILED DESCRIPTION OF SPECIFIC EMBODIMENTS

In one specific embodiment of the present disclosure, electronic device 218 is a wearable device in the form factor of a bracelet or wristband that is worn around the wrist or arm of a user's dominant hand. Electronic device 219 is a mobile phone and central processing and storage unit 220 is one or more computer servers and data storage that are located at a remote location.

Figure 7:
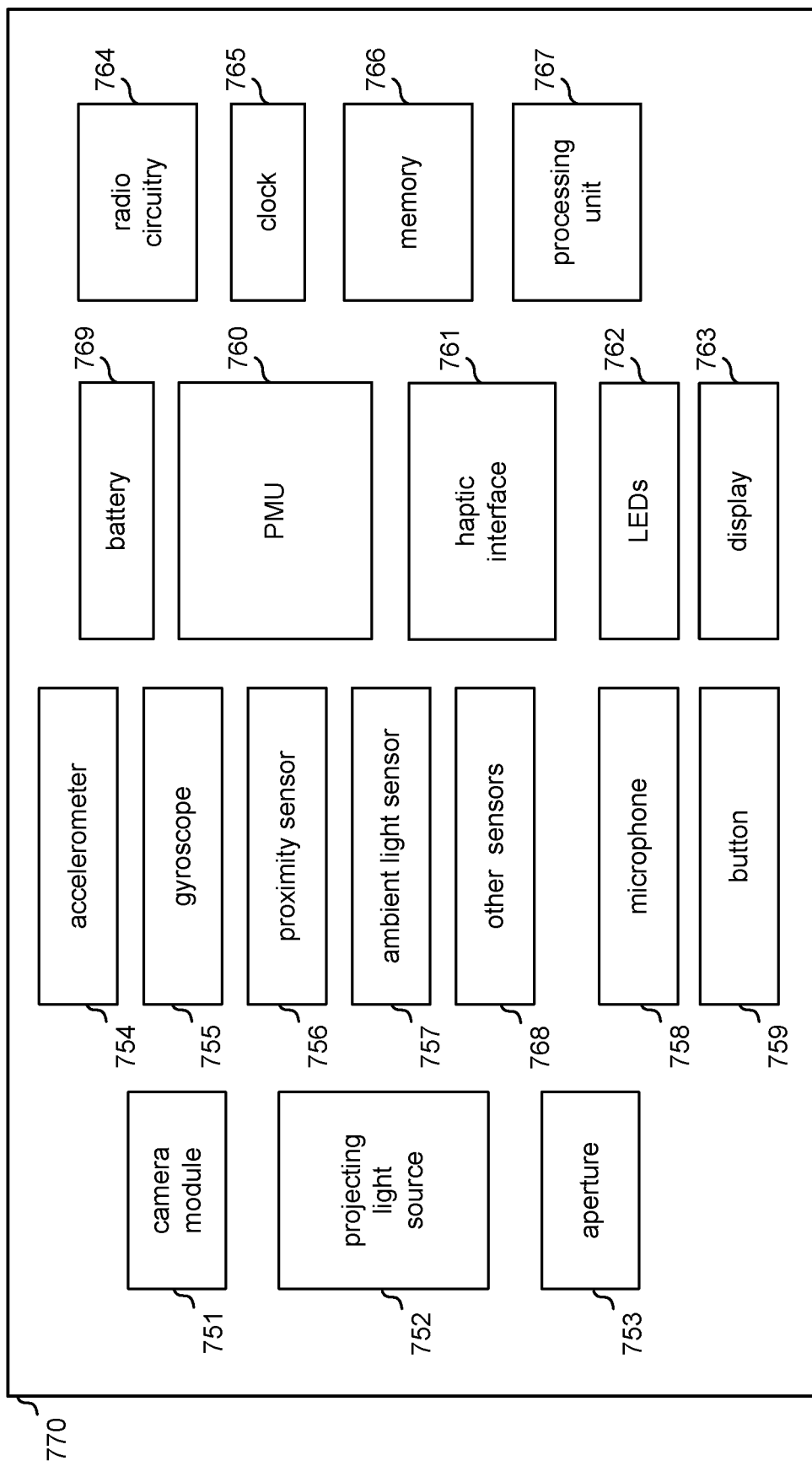
FIG. 7 is an illustrative example of a block diagram of a monitoring and tracking device in accordance with at least one embodiment.

One possible implementation of a wearable bracelet or wristband in accordance with aspects of the present invention is shown in FIG. 7. Wearable device 770 may optionally be implemented using a modular design, wherein individual modules include one or more subsets of the components and overall functionality. The user may choose to add specific modules based on his personal preferences and requirements.

The wearable device 770 may include a processor, a program code memory or storage medium, and program code (software) stored therein and/or inside electronic device 219 to optionally allow users to customize a subset of the functionality of wearable device 770.

Wearable device 770 relies on battery 769 and Power Management Unit ("PMU") 760 to deliver power at the proper supply voltage levels to all electronic circuits and components. Power Management Unit 760 may also include battery-recharging circuitry. Power Management Unit 760 may also include hardware such as switches that allows power to specific electronics circuits and components to be cut off when not in use.

When there is no behavior event in progress, most circuitry and components in wearable device 770 are switched off to conserve power. Only circuitry and components that are required to detect or help predict the start of a behavior event may remain enabled. For example, if no motion is being detected, all sensor circuits but the accelerometer may be switched off and the accelerometer may be put in a low-power wake-on-motion mode or in another lower power mode that consumes less power than its high performance active mode. The processing unit may also be placed into a low-power mode to conserve power. When motion or a certain motion pattern is detected, the accelerometer and/or processing unit may switch into a higher power mode and additional sensors such as for example the gyroscope and/or proximity sensor may also be enabled. When a potential start of an event is detected, memory variables for storing event-specific parameters, such as gesture types, gesture duration, etc. can be initialized.

In another example, upon detection of motion, the accelerometer switches into a higher power mode, but other sensors remain switched off until the data from the accelerometer indicates that the start of a behavior event has likely occurred. At that point in time, additional sensors such as the gyroscope and the proximity sensor may be enabled.

In another example, when there is no behavior event in progress, both the accelerometer and gyroscope are enabled but at least one of either the accelerometer or gyroscope is placed in a lower power mode compared to their regular power mode. For example, the sampling rate may be reduced to conserve power. Similarly, the circuitry required to transfer data from electronic device 218 to electronic device 219 may be placed in a lower power mode. For example, radio circuitry 764 could be disabled completely. Similarly, the circuitry required to transfer data from electronic device 218 to electronic device 219 may be placed in a lower power mode. For example, it could be disabled completely until a possible or likely start of a behavior event has been determined. Alternatively, it may remain enabled but in a low power state to maintain the connection between electronic device 218 and electronic device 219 but without transferring sensor data.

In yet another example, all motion-detection related circuitry, including the accelerometer may be switched off, if based on certain meta-data it is determined that the occurrence of a particular behavior event such as a food intake event is unlikely. This may for example be desirable to further conserve power. Meta-data used to make this determination may, among other things, include one or more of the following: time of the day, location, ambient light levels, proximity sensing, and detection that wearable device 770 has been removed from the wrist or hand, detection that wearable device 770 is being charged. Meta-data may be generated and collected inside wearable device 770. Alternatively, meta-data may be collected inside the mobile phone or inside another device that is external to wearable device 770 and to the mobile phone and that can either directly or indirectly exchange information with the mobile phone and/or wearable device 770. It is also possible that some of the meta-data are generated and collected inside wearable device 770 whereas other meta-data are generated and collected in a device that is external to wearable device 770. In case some or all of the meta-data are generated and collected external to wearable device 770, wearable device 770 may periodically or from time to time power up its radio circuitry 764 to retrieve meta-data related information from the mobile phone or other external device.

In yet another embodiment of the invention, some or all of the sensors may be turned on or placed in a higher power mode if certain meta-data indicates that the occurrence of a particular behavior event, like for example a food intake event is likely. Meta-data used to make this determination may, among other things, include one or more of the following: time of the day, location, ambient light levels and proximity sensing. Some or all of the meta-data may be collected inside the mobile phone or inside another device that is external to wearable device 770 and to the mobile phone and that can either directly or indirectly exchange information with the mobile phone and/or wearable device 770. In case some or all of the meta-data are generated and collected external to wearable device 770, wearable device 770 may periodically or from time to time power up its radio circuitry 764 to retrieve meta-data related information from the mobile phone or other external device.

The detection of the start of a behavior event, such as for example a food intake event may be signaled to the user via one of the available user interfaces on wearable device 770 or on the mobile phone to which wearable device 770 is connected. As one example, haptic interface 761 inside wearable device 770 may be used for this purpose. Other signaling methods are also possible.

The detection of the start of a behavior event such as for example a food intake event may trigger some or all of the sensors to be placed or remain in a high-power mode or active mode to track certain aspects of a user's eating behavior for a portion or for the entirety of the food intake event. One or more sensors may be powered down or placed in a lower power mode when or sometime after the actual or probable end of the behavior event (the deemed end of the behavior event) has been detected. Alternatively, it is also possible that one or more sensors are powered down or placed in a lower power mode after a fixed or programmable period of time.

Sensor data used to track certain aspects of a user's behavior, such as for example a user's eating behavior, may be stored locally inside memory 766 of wearable device 770 and processed locally using processing unit 767 inside wearable device 770. Sensor data may also be transferred to the mobile phone or remote compute server, using radio circuitry 764, for further processing and analysis. It is also possible that some of the processing and analysis is done locally inside wearable device 770 and other processing and analysis is done on the mobile phone or on a remote compute server.

The detection of the start of a behavior event, such as for example the start of a food intake event, may trigger the power up and/or activation of additional sensors and circuitry such as for example the camera module 751. Power up and/or activation of additional sensors and circuitry may happen at the same time as the detection of the start of a food intake event or sometime later. Specific sensors and circuitry may be turned on only at specific times during a food intake event when needed and may be switched off otherwise to conserve power.

It is also possible that the camera module 751 only gets powered up or activated upon explicit user intervention such as for example pushing and holding a button 759. Releasing the button 759 may turn off the camera module 751 again to conserve power.

When the camera module 751 is powered up, projecting light source 752 may also be enabled to provide visual feedback to the user about the area that is within view of the camera. Alternatively, projecting light source 752 may only be activated sometime after the camera module has been activated. In certain cases, additional conditions may need to be met before projecting light source 752 gets activated. Such conditions may, among other things, include the determination that projecting light source 752 is likely aiming in the direction of the object of interest, or the determination that the wearable device is not moving excessively.

In one specific implementation, partially depressing button 759 on wearable device 770 may power up the camera module 751 and projecting light source 752. Further depressing button 759 may trigger camera module 751 to take one or more still images or one or more streaming images. In certain cases, further depressing button 759 may trigger a de-activation, a modified brightness, a modified color, or a modified pattern of projected light source 752 either before or coinciding with the image capture. Release of button 759 may trigger a de-activation and/or power down of projected light source 752 and/or of camera module 751.

Images may be tagged with additional information or meta-data such as for example camera focal information, proximity information from proximity sensor 756, ambient light levels information from ambient light sensor 757, timing information etc. Such additional information or metadata may be used during the processing and analysis of food intake data.

Various light patterns are possible and may be formed in various ways. For example, it may include a mirror or mechanism to reflect projecting light source 752 such that projected light source 752 produces one or more lines of light, outlines the center or boundaries a specific area, such as a cross, L-shape, circle, rectangle, multiple dots or lines framing the field of view or otherwise giving to the user visual feedback about the field of view.

One or more Light Emitting Diodes (LEDs) may be used as projecting light source 752. The pattern of visible light may, among other things, be used by the user to adjust the position of the camera, adjust the position the object of interest and/or remove any objects that are obstructing the line of sight between the object of interest and the camera.

Projected light source 752 may also be used to communicate other information to the user. As an example, the electronic device may use inputs from one or more proximity sensors, process those inputs to determine if the camera is within the proper distance range from the object of interest, and use one or more light sources to communicate to the user that the camera is within the proper distance range, that the user needs to increase the distance between camera and the object of interest, or that the user needs to reduce the distance between the camera and the object of interest.

The light source may also be used in combination with an ambient light sensor to communicate to the user if the ambient light is insufficient or too strong for an adequate quality image capture.

The light source may also be used to communicate information including, but not limited to, a low battery situation or a functional defect.

The light source may also be used to communicate dietary coaching information. As an example, the light source might, among other things, indicate if not enough or too much time has expired since the previous food intake event, or may communicate to the user how he/she is doing against specific dietary goals.

Signaling mechanisms to convey specific messages using one or more projecting light sources may include, but are not limited to, one or more of the following: specific light intensities or light intensity patterns, specific light colors or light color patterns, specific spatial or temporal light patterns. Multiple mechanisms may also be combined to signal one specific message.

Microphone 758 may be used by the user to add specific or custom labels or messages to a food intake event and/or image. Audio snippets may be processed by a voice recognition engine.

In certain embodiments, the accelerometer possibly combined with other sensors may, in addition to tracking at least one parameter that is directly related to food intake and/or eating behavior, also be used to track one or more parameters that are not directly related to food intake. Such parameters may, among other things, include activity, sleep or stress.

Specific Embodiments without Built-in Camera

In a different embodiment, electronic device 218 need not have any built-in image capture capabilities. Electronic device 218 may be a wearable device such as a bracelet or wristband worn around the arm or wrist, or a ring worn around the finger. Electronic device 219 may be a mobile phone and central processing and storage unit 220 may be one or more compute servers and data storage that are located at a remote location.

In such embodiments, the food intake tracking and feedback system may not use images to extract information about food intake and/or eating behavior. Alternatively, the food intake tracking and feedback system may leverage image capture capabilities that are available inside other devices, such as for example electronic device 219 or otherwise an electronic device that is external to electronic device 218.

Upon detection or prediction of the start of a food intake event, electronic device 218 may send a signal to electronic device 219, or to the electronic device that is otherwise housing the image capture capabilities to indicate that the actual, probable or imminent start of a food intake event has occurred. This may trigger electronic device 219, or the electronic device that is otherwise housing the image capture capabilities to enter a mode that will allow the user to capture an image with at least one less user step compared to its default mode or standby mode.

As an example, if the image capture capabilities are housed within electronic device 219 and electronic device 219 is a mobile phone, a tablet or a similar mobile device, electronic device 218 may send one or more signals to software that has been installed on electronic device 219 to indicate the actual, probable or imminent start of a food intake event. Upon receiving such signal or signals, the software on electronic device 219 may, among other things, take one or more of the following actions: unlock the screen of electronic device 219, open the Mobile Application related to the food intake and feedback subsystem, activate electronic device's 219 camera mode, push a notification to electronic device's 219 display to help a user with image capture, send a message to electronic device 218 to alert, remind and/or help a user with image capture.

After image capture by electronic device 219, or the electronic device that is otherwise housing the image capture capabilities, electronic device 219, or the electronic device that is otherwise housing the image capture capabilities, may give visual feedback to the user. Examples of visual feedback may include a pattern, shape or overlay showing recommended portion sizes, or a pattern, shape or overlay shade in one or more colors and/or with one or more brightness levels to indicate how healthy the food is. Other examples are also possible.

Integration with Insulin Therapy System

One or more components of the food intake tracking and feedback system presented in this disclosure may interface to or be integrated with an insulin therapy system. In one specific example, upon detection of the start of a food intake event, feedback may be sent to the wearer to remind him or her to take a glucose level measurement and/or administer the proper dosage of insulin. One or more additional reminders may be sent over the course of the food intake event.

The food intake tracking and feedback system described in this disclosure, or components thereof may also be used by patients who have been diagnosed with Type I or Type II diabetes. For example, components described in the current disclosure may be used to detect automatically when a person starts, is about to start, or has started eating or drinking. The detection of the start of a food intake event may be used to send a message to the wearer at or near the start of a food intake event to remind him or her to take a glucose level measurement and/or administer the proper dosage of insulin. The messaging may be automatic and stand alone. Alternatively, the system may be integrated with a wellness system or a healthcare maintenance and reminder system. The wellness system or the healthcare maintenance and reminder system may upon getting notified that the start of a food intake event has been detected send a message to the wearer. The wellness system or the healthcare maintenance and reminder system may receive additional information about the food intake event, such as the number of bites or sips, the estimated amount of food consumed, the duration of the meal, the pace of eating etc. The wellness system or the healthcare maintenance and reminder system may send additional messages to the wearer during or after the food intake event based on the additional information.

In another example, specific information about the content of the food intake may be used as an input, possibly combined with one or more other inputs, to compute the proper dosage of insulin to be administered. Information about food intake content may, among other things, include one or more of the following: amount of carbohydrates, amounts of sugars, amounts of fat, portion size, and molecular food category such as solids or liquids. Real-time, near real-time as well as historical information related food intake and eating patterns and behaviors may be included as inputs or parameters for computation of insulin dosages.

Other inputs that may be used as inputs or parameters to the algorithms that are used to compute insulin dosages may include, among other things, one or more of the following: age, gender, weight, historical and real-time blood glucose levels, historical and real-time activity, sleep and stress levels, vital sign information or other information indicative of the physical or emotional health of an individual.

Computation of insulin dosages may be done fully manually by the user, fully autonomously by a closed loop insulin therapy system or semi-autonomously where some or all of the computation is done by an insulin therapy system but some user intervention is still required. User intervention may, among other things, include activation of the insulin therapy computation unit, confirmation of the dosage, intervene or suspend insulin delivery in case user detects or identifies an anomaly.

In one specific embodiment, the food intake tracking and feedback system described herein may upon detection of the actual, probable or imminent start of a food intake event send one or more notifications to one or more caregivers of the user, in addition or instead of sending a notification to the user.

The user may upon the start of a food intake event, optionally prompted by a notification or signal from the system or from a caregiver, take one or more images of the food or meal to one or more caregiver. The caregiver may analyze the images and send information about the content of the food back to the user. Information may, among other things, include estimation of certain macro-nutrient contents such as for example carbohydrates, sugars or fats, estimation of caloric value, advice on portion size.

In case the user is on an insulin therapy, additional information such as for example blood glucose level readings may also be sent to the caregiver, and information provided by a caregiver back to a user may also include advice on the insulin dosage to be administered and the timing when such insulin dosage or dosages should be administered. In certain implementations, the caregiver may not be a person but an artificial intelligence system.

Gesture Recognition

In the various systems described herein, accurate determination of gesture information can be important. For example, it would be useful to distinguish between a gesture connected with talking versus a gesture that signals the start of an eating event period. Some gestures might be easy to detect, such as the gesture of swinging an arm while walking, and thus measuring pace and number of steps, but other gestures might be more difficult, such as determining when a user is taking a bite of food, taking a drink, biting their nails, etc. The latter can be useful for assessing precursor behaviors. For example, suppose a health maintenance and reminder system detects a pattern of nail biting gestures followed five to ten minutes later with gestures associated with stress eating. The user might program their health maintenance and reminder system to signal them two minutes after nail biting so that the user becomes aware and more in tune with their behavior that would otherwise go unnoticed. For this to work, gesture detection should be accurate and reliable. This can be a problem where there is not a simple correlation between, say, movement of an accelerometer in a wearable bracelet and stress eating. Part of the reason for this is that the gestures that are of interest to the health maintenance and reminder system are not easily derived from a simple sensor reading.

Being able to determine whether a user is taking a bite of food or taking a sip of a drink, and being able to distinguish a bite from a sip, can be useful to provide proper weight management guidance. For example, a weight management monitoring and reminder system may monitor a user's food intake events from gestures. The weight management monitoring and reminder system may furthermore monitor a user's fluid intake events from gestures. Studies have shown that drinking sufficient water at the start or close to the start of a meal and further drinking sufficiently throughout the meal reduces food consumption and helps with weight loss. The user, the user's coach, the user's healthcare provider, or the provider of the weight management monitoring and reminder system may program the system such that it sends a reminder when a user starts eating without drinking or if it detects that the user is not drinking sufficiently throughout the meal. The system could also monitor the user's fluid intake throughout the day and be programmed to send reminders if the level of fluid intake does not meet the pre-configured level for a particular time of day. For this to work, the gesture detection should be reliable and accurate. This can be a problem where it is necessary to distinguish between gestures that have lots of similarities, such as for example distinguishing an eating gesture from a drinking gesture.

In various embodiments described herein, a processing system (comprising program code, logic, hardware, and/or software, etc.) takes in sensor data generated by electronic devices or other elements based on activities of a user. The sensor data might represent a snapshot of a reading at a specific time or might represent readings over a span of time. The sensors might be accelerometers, gyroscopes, magnetometers, thermometers, light meters and the like. From the sensor data, the processing system uses stored rules and internal data (such as information about what sensors are used and past history of use) to identify behavior events wherein a behavior event is a sequence of gestures and the gestures are determined from logical arrangement of sensor data having a start time, sensor readings, and an end time, as well as external data. The behavior event might be a high-level event, such as eating a meal, etc.

The determination of the boundaries of gestures, i.e., their start and end times, can be determined using methods described herein. Together, the data of a start time, sensor readings, and an end time is referred to herein as a gesture envelope. The gesture envelope might also include an anchor time, which is a data element defining a single time that is associated with that gesture envelope. The anchor time might be the midpoint between the start time and the end time, but might be based on some criteria based on the sensor data of the gesture envelope. An anchor time might be outside of the time span from the start time to the end time. Multiple anchor times per gesture are also possible.

A machine classifier, as part of the processing system (but can also be a separate computer system, and possibly separated by a network of some kind), determines from a gesture envelope what class of gesture might have resulted in that gesture envelope's sensor data and details of the gesture. For example, the machine classifier might output that the sensor data indicates or suggests that a person wearing a bracelet that includes sensors was taking a walk, talking a bite to eat, or pointing at something.

With such a system, if gestures can be accurately discerned, then a health maintenance and reminder system (or other system that uses gesture information) can accurately respond to gestures made. In an example described below, there is a set of sensors, or at least inputs from a set of sensors, coupled to a machine classification system that outputs gesture data from sensor readings, taking into account rules and stored data derived from training the machine classification system. A training subsystem might be used to train the machine classification system and thereby forming the stored data derived from training. Each of these components might use distinct hardware, or shared hardware, and can be localized and/or remote. In general, when a gesture is detected, a system can analyze that gesture, determine likely actual, probable or imminent activities and provide the user feedback with respect to those activities. For example, a vibration as a feedback signal to indicate that the user has previously set up the system to alert the user when the user has been drinking for a semi-continuous period of more than 45 minutes or that the user has reached their target for the amount of walking to be done in one session.

Figure 8:
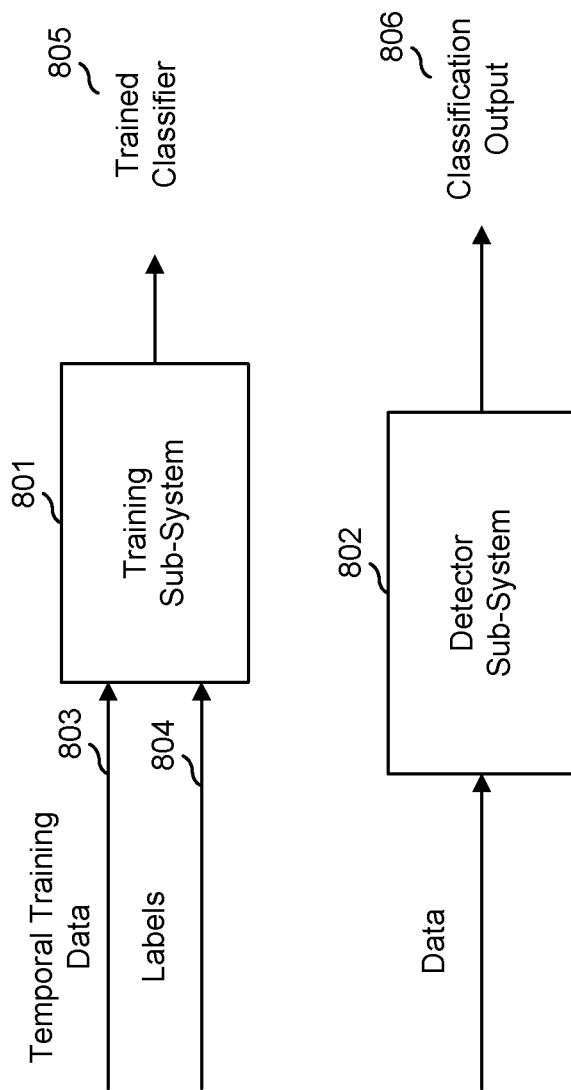
FIG. 8 shows an example of a machine classification system in accordance with at least one embodiment of the present disclosure.

FIG. 8 is an illustrative example of a typical machine classification system. The machine classification system of FIG. 8 includes a training subsystem 801 and a detector subsystem 802. In some embodiments of the present disclosure, the machine classification system may include additional subsystems or modified versions of the subsystems shown in FIG. 8. Training subsystem 801 uses training data inputs 803 and labels 804 to train trained classifier model 805. Labels 804 may have been assigned manually by a human or may have been generated automatically or semi-automatically. Trained classifier model 805 is then used in detector subsystem 802 to generate classification output 806 corresponding to a new unlabeled data input.

The stored sensor data includes temporal components. Raw sensor readings are tagged with their time of reading. The raw sensor data can be drawn from accelerometers, gyroscopes, magnetometers, thermometers, barometers, humidity sensors, ECG sensors and the like, and temporal data can come from other sources. Other examples of temporal sources might be audio, voice or video recordings.

Figure 9:
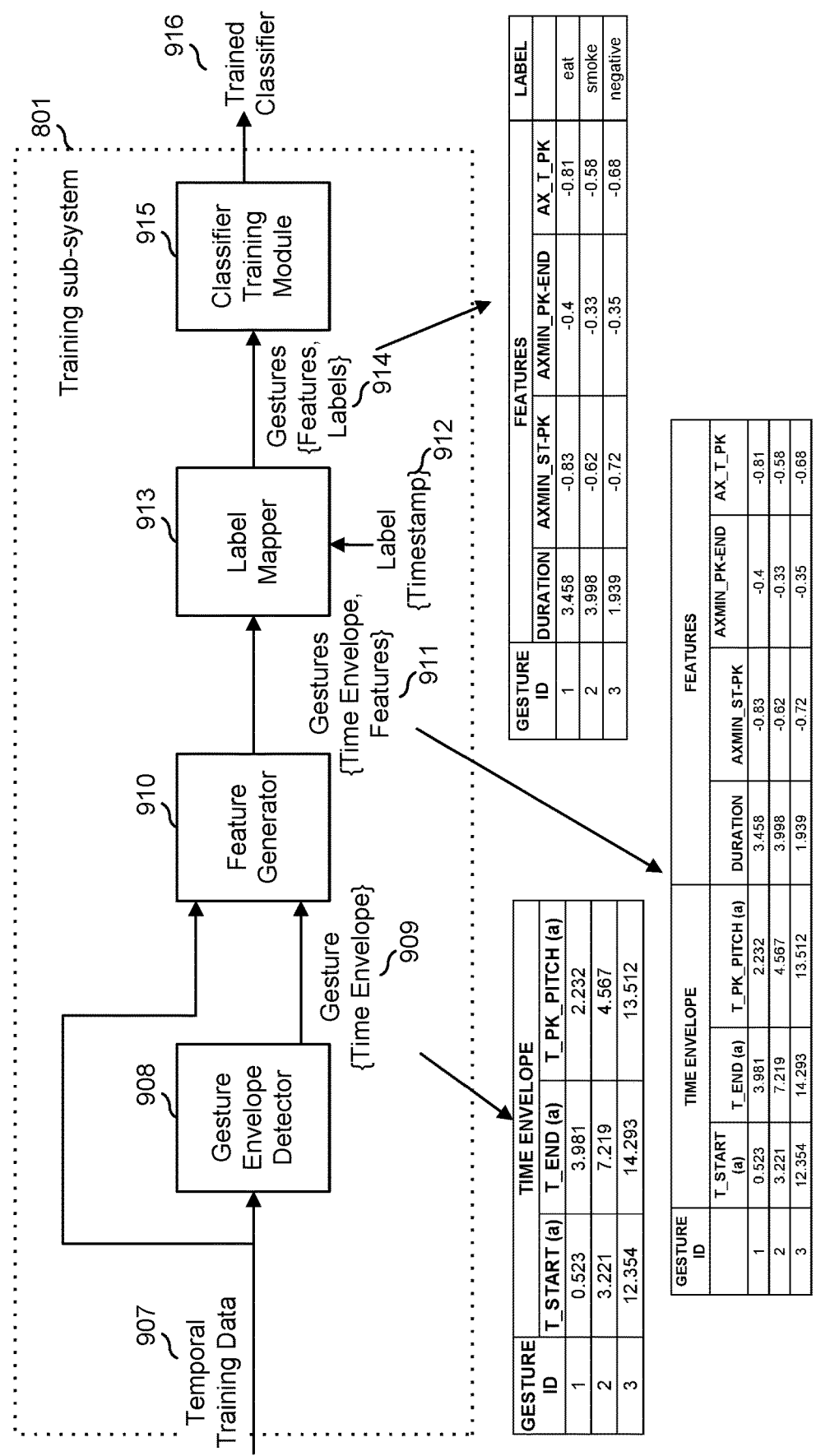
FIG. 9 shows an example of a machine classification training subsystem in accordance with at least one embodiment of the present disclosure.
Figure 10:
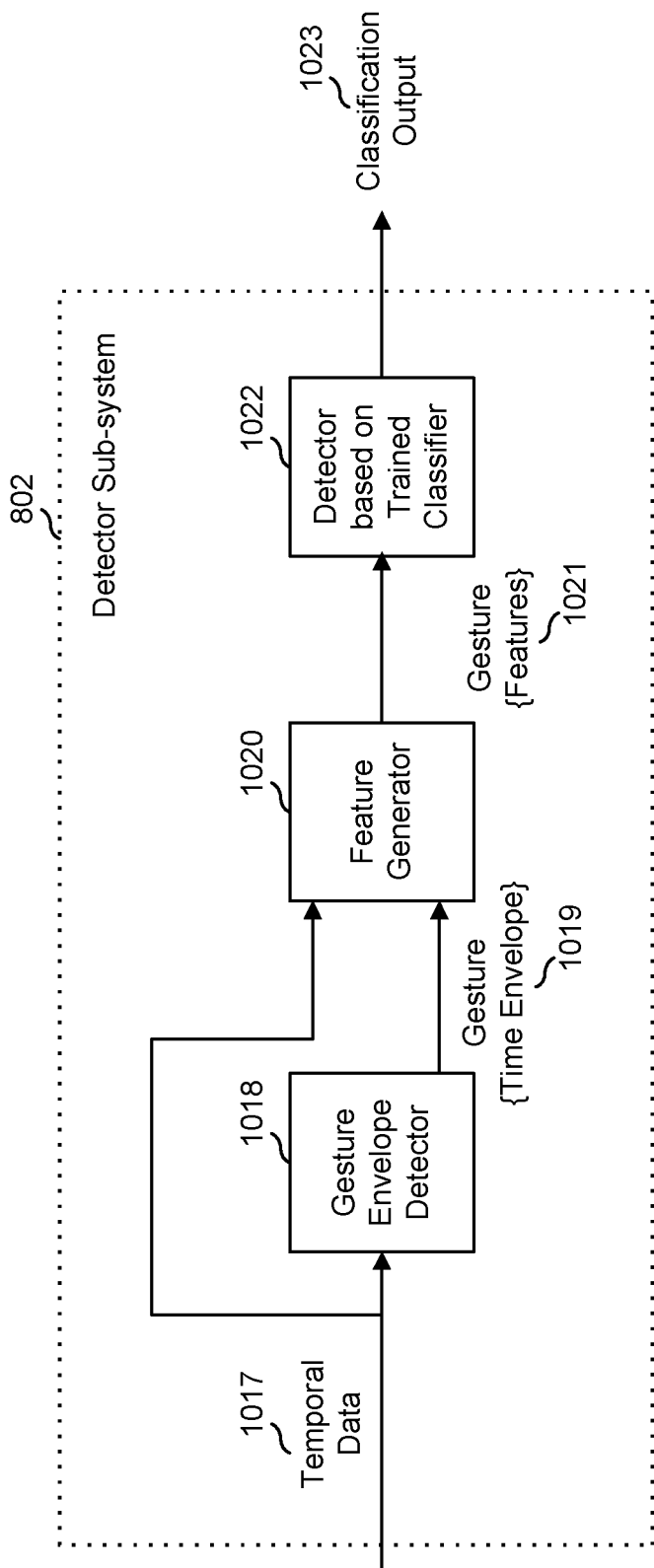
FIG. 10 shows an example of a machine classification detector subsystem in accordance with at least one embodiment of the present disclosure.

Illustrative examples of training subsystem 801 and detector subsystem 802 in accordance with at least one embodiment of the present disclosure are shown in FIG. 9 and FIG. 10 respectively. Temporal training data 907 and labels 912 are fed into classifier training subsystem of FIG. 8.

As explained in the examples herein, raw sensor data is processed to identify macro signature events. The macro signature events can delimit gestures that comprise sensor data over a period of time. The detector subsystem, or other system, can create a gesture envelope dataset comprising a start time, an end time, one or more anchor times, metadata and sensor data that occurred within that gesture's time envelope from the start time to the end time.

For example, in the case of a gesture recognition problem, the gesture envelope detector may identify specific time segments in the raw temporal data that are indicative of a possible gesture. The gesture envelope detector also generates a time envelope that specifies relevant times or segments of time within the gesture. Information included in the time envelope may among other things include start time of the gesture, end time of the gesture, time or times within the gesture that specify relevant gesture sub-segments, time or times within the gesture that specify relevant gesture anchor times (points) and possibly other metadata, and raw sensor data from within the gesture's time envelope.

As an example of other metadata, suppose historical patterns suggest that a wearer would have an eating session following a telephone call from a particular phone number. The electronic device can signal to the wearer about this condition, to provide conscious awareness of the pattern, which can help alter behavior if the wearer so decides.

Temporal training data 907 are fed into a gesture envelope detector 908. Gesture envelope detector 908 processes temporal training data 907 and identifies possible instances of gestures 909 and a corresponding gesture time envelope from temporal training data 907. Temporal training data 907 may comprise motion sensor data and gesture envelope detector 908 may be processing the motion sensor data and identify gestures 909 based on changes in pitch angle. In one embodiment, gesture envelope detector 908 may detect the start of a gesture based on the detection of a rise in pitch angle above a specified value and the end of an event based on the pitch angle dropping below a specified value. Other start and end criteria are also possible. An example of anchor points that may be detected by gesture envelope detector 908 and specified by the gesture time envelope would be the time within the gesture segment when the pitch angle reaches a maximum. Other examples of anchor points are also possible.

Gesture envelope detector 908 may add additional criteria to further qualify the segment as a valid gesture. For example, a threshold could be specified for the peak pitch angle or the average pitch angle within the segment. In another example, minimum and/or maximum limits may be specified for the overall segment duration or for the duration of sub-segments within the overall segment. Other criteria are also possible. Hysteresis may be employed to reduce the sensitivity to noise jitters.

In other embodiments of the present disclosure, gesture envelope detector 908 may monitor other metrics derived from the input providing temporal training data 907 and use those metrics to detect gestures. Examples of other metrics include but are not limited to roll angle, yaw, first or higher order derivative, or first or higher order integration of motion sensor data. Temporal data may be, or may include, data other than motion sensor data. In some embodiments of the present disclosure, a gesture envelope detector 908 may monitor and use multiple metrics to detect gestures or to specify the gesture time envelope.

Gestures 909 along with gesture time envelope information, combined with temporal training data 907 are fed into a feature generator module 910. Feature generator module 910 computes one or more gesture features using information from temporal training data 907, the gesture time envelope, or a combination of information from temporal training data 907 and the gesture time envelope. In some embodiments of the present disclosure, feature generator module 910 computes one or more gesture features from temporal training data 907 within or over a time segment that falls within the gesture time envelope. It is also possible that feature generator module 910 computes one or more gesture features from temporal training data 907 within or over a time segment that does not fall within or that only partially falls within the gesture time envelope, but that is still related to the gesture time envelope. An example would be a gesture feature that is computed from temporal training data 907 over a time period immediately preceding the start of the gesture time envelope or over a time period immediately following the end of the gesture time envelope.

In some embodiments, feature generator module 910 may create one or more features based on gesture time envelope information directly without using temporal training data 907. Examples of such features may include, but are not limited to, total duration of the gesture time envelope, elapsed time since a last prior gesture, a time until next gesture, or durations of specific sub-segments within the overall gesture time envelope or event time envelope.

In one embodiment, temporal training data 907 may be motion sensor data and features may include read of pitch, roll and/or yaw angles computed within, or over, one or more sub-segments that are inside or around the gesture time envelope. Features may also include minimum, maximum, mean, variance, first or higher order derivative, first or higher order integrals of various motion sensor data inputs computed within or over one or more sub-segments that are inside or around the gesture time envelope. Features may also include distance traveled along a specific sensor axis or in a specific direction computed within or over one or more sub-segments that are inside or around the gesture time envelope Temporal training data 907 may be, or may include, data other than motion sensor data, such as sensor signals from one or more of the sensors described herein. Sub-segments within or over which feature generator module 910 computes features may be chosen based on time points or time segments specified by the gesture time envelope. Sub-segments may also be chosen based on time points or time segments from multiple gesture envelopes, such as for example adjacent gestures or gestures that may not be adjacent but are otherwise in close proximity.

Some embodiments may use a plurality of gesture envelope detectors, in parallel or otherwise. Parallel gesture envelope detectors may operate on a different subset of the sensor data, may use different thresholds or criteria to qualify gestures, etc. For example, in case of gesture recognition based on motion sensor data inputs, one gesture envelope detector may use the pitch angle, whereas a second, parallel gesture envelope detector may use roll angle. One of the gesture envelope detectors may be the primary gesture envelope detector, whereas one or more additional gesture envelope detectors may serve as secondary gesture envelope detectors. The Feature Generation logic may process gestures generated by the primary gesture envelope detector, but may gleam features derived using information from gesture time envelopes of nearby gestures (in time) obtained from one or more secondary, parallel envelope detectors.

Training data might comprise a plurality of gesture envelope datasets, each having an associated label representing a gesture (such as a selection from a list of gesture labels), provided manually, in a test environment, or in some other manner. This training data, with the associated labels, can be used to train the machine classifier, so that it can later process a gesture envelope of an unknown gesture and determine the gesture label most appropriately matching that gesture envelope. Depending on the classification method used, the training set may either be cleaned, but otherwise raw data (unsupervised classification) or a set of features derived from cleaned, but otherwise raw data (supervised classification).

Regardless of the classification method, defining the proper data boundaries for each label is important to the performance of the classifier. Defining the proper data boundaries can be a challenge in case of temporal problems, i.e., problems whereby at least one of the data inputs has a time dimension associated with it. This is particularly true if the time dimension is variable or dynamic and if features that are linked to specific segments of the variable time envelope or to the overall variable time envelope contribute materially to the performance of the classifier.

One example of such a temporal problem is gesture recognition, such as for example the detection of an eating or drinking gesture from raw motion sensor data. The duration of a bite or sip may vary person-to-person and may depend on the meal scenario or specifics of the foods being consumed.

The output of the feature generator module 910 is a set of gestures 911 with corresponding time envelope and features. Before gestures 911 can be fed into Classifier Training module 915, labels 912 from the training dataset need to be mapped to their corresponding gesture. This mapping operation is performed by the Label Mapper module 913.

In some embodiments, the timestamps associated with labels 912 always fall within the time envelope of their corresponding gesture. In that case, the logic of Label Mapper module 913 can be a look up where the timestamp of each label is compared to the start and end time of each gesture time envelope and each label is mapped to the gesture for which the timestamp of the label is larger than the start time of the respective gesture time envelope and smaller than the end time of the respective gesture time envelope. Gestures for which there is no corresponding label may be labeled as "NEGATIVE", indicating it does not correspond to any labels of interest.

However, in other embodiments of the present disclosure, the timestamp of labels 912 may not always fall within a gesture time envelope. This may be due to the specifics of the procedures that were followed during the labeling process, timing uncertainty associated with the labeling process, unpredictability or variability in the actual raw data input, or an artifact of the gesture envelope detector logic. In such cases, the label mapper might be modified to adjust the boundaries of the gesture envelopes.

Gestures 914, characterized by features and a label, may then be fed into Classifier Training module 915 to produce a trained statistical model that can be used by the Detector subsystem. Classifier Training module 915 may use a statistical model such as a decision tree model, a K-nearest neighbors model, a Support Vector Machine model, a neural networks model, a logistic regression model or other model appropriate for a machine classification. In other variations, the structures of the tables and the data formats of the data used, as in FIG. 9, may vary and be different from that shown in FIG. 9.

FIG. 10 shows an illustrative example of a detector subsystem 802. As shown there, unlabeled temporal data 1017 is fed into the detector subsystem of FIG. 10. The detector subsystem includes gesture envelope detector logic 1018 and feature generator logic 1020. Functionally, gesture envelope detector logic 1018 used by the detector subsystem is similar to gesture envelope detector logic used by its corresponding training subsystem. Likewise, feature generator logic 1020 of the detector subsystem is functionally similar to feature generator module 910 of its corresponding training subsystem. In some embodiments, gesture envelope detector logic 1018 may monitor and use multiple metrics to detect gestures or to specify the gesture time envelope.

However, the implementation of gesture envelope detector logic 1018 and feature generator logic 1020 may be different in the training subsystem and its corresponding detector subsystem. For example, the detector subsystem may be implemented on hardware that is more power-constrained, in which case gesture envelope detector logic 1018 may need to be optimized for lower power operation compared to its counterpart used in the corresponding training subsystem. The detector subsystem may also have more stringent latency requirements compared to the training system. If this is the case, gesture envelope detector logic 1018 used in the detector subsystem may need to be designed and implemented for lower latency compared to its counterpart used in the corresponding training subsystem.

An output of feature generator logic 1020 is fed into detector logic 1022, which classifies the gesture based on the trained classifier module from its corresponding training subsystem. The Classification Output may include one or more labels. Optionally, detector 1022 may also assign a confidence level to each label.

Classification on Combination of Temporal and Non-Temporal Data Inputs

Figure 11:
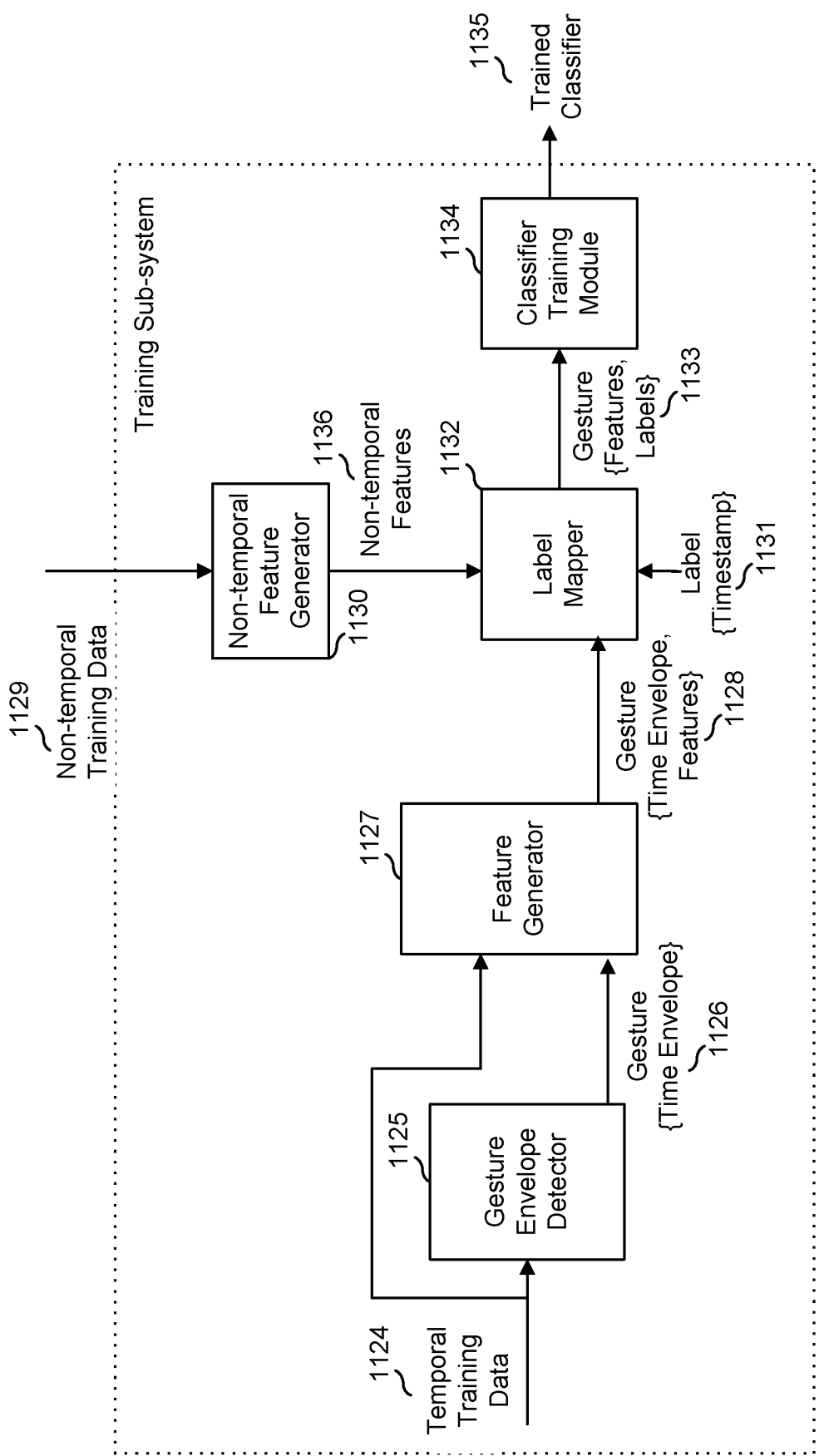
FIG. 11 shows an example of a machine classification training subsystem that uses, among other data, non-temporal data.

In another embodiment, inputs into the classification system may include a combination of temporal and non-temporal data. FIG. 11 is an illustrative example of a training subsystem in accordance with at least one embodiment of the present disclosure where at least some of the data inputs are temporal and at least some of the data inputs are non-temporal. Other implementations are also possible.

Non-temporal training data 1129 do not need to be processed by gesture envelope detector 1125 and feature generator Logic 1127. Non-temporal training data 1129 may be fed directly into the label mapper logic 1132 along with labels 1131. In some embodiments, non-temporal training data may be processed by a separate feature generator module, non-temporal feature generator module 1130, to extract specific non-temporal features of interest, which are then fed into Label mapper logic 1132. Label mapper logic 1132 may assign the labels 1131, along with non-temporal features 1136 that are attached to the label to gestures using methods similar to the methods for mapping labels to gestures that have been described herein.

Figure 12:
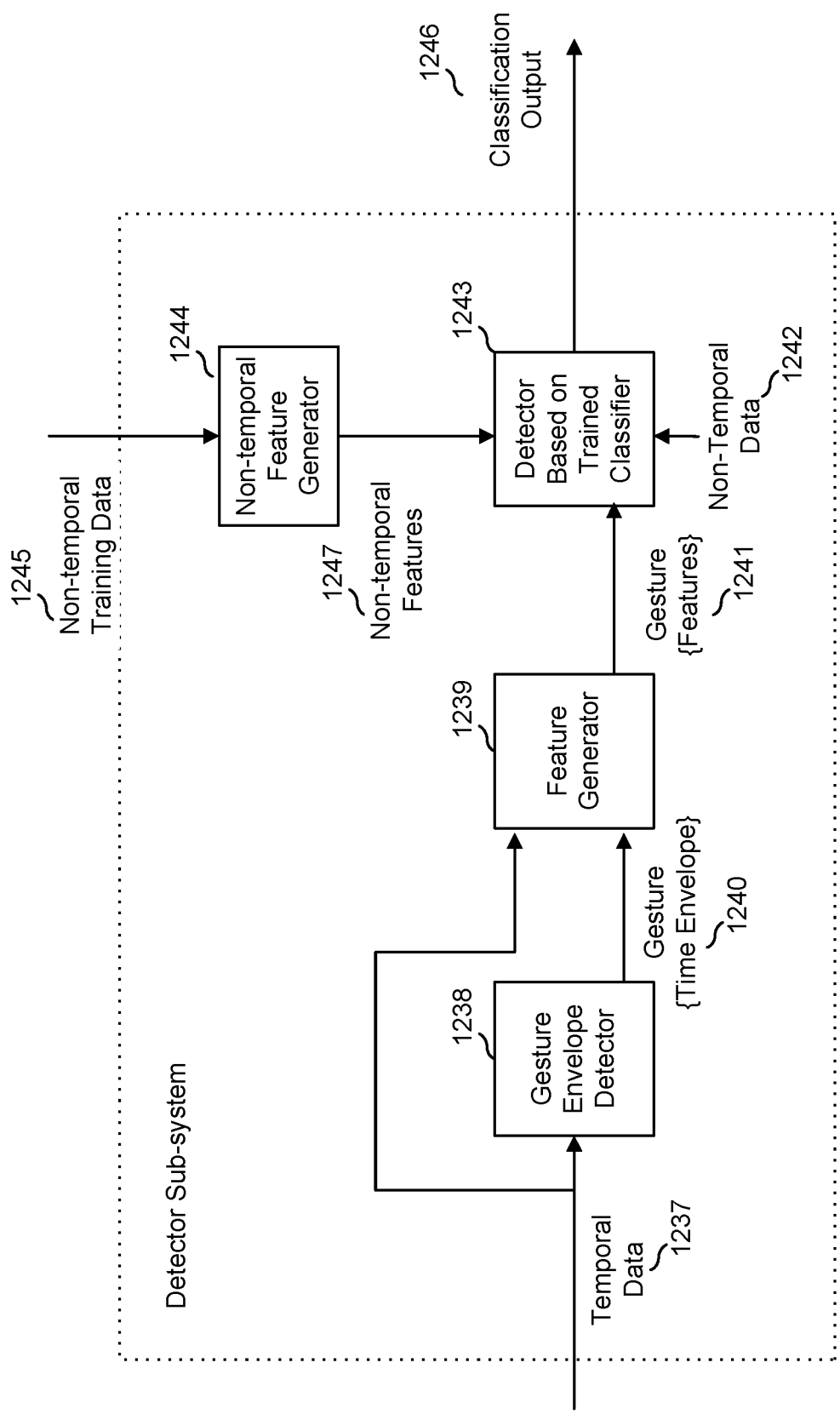
FIG. 12 shows an example of a machine classification detector subsystem that uses, among other data, non-temporal data.

FIG. 12 is an illustrative example of a classification detector subsystem in accordance with at least one embodiment of the present disclosure where at least some of the data inputs are temporal and at least some of the data inputs are non-temporal.

Unsupervised Classification of Temporal Data Inputs

In yet another embodiment of the present disclosure, deep learning algorithms may be used for machine classification. Classification using deep learning algorithms is sometimes referred to as unsupervised classification. With unsupervised classification, the statistical deep learning algorithms perform the classification task based on processing of the data directly, thereby eliminating the need for a feature generation step.

Figure 13:
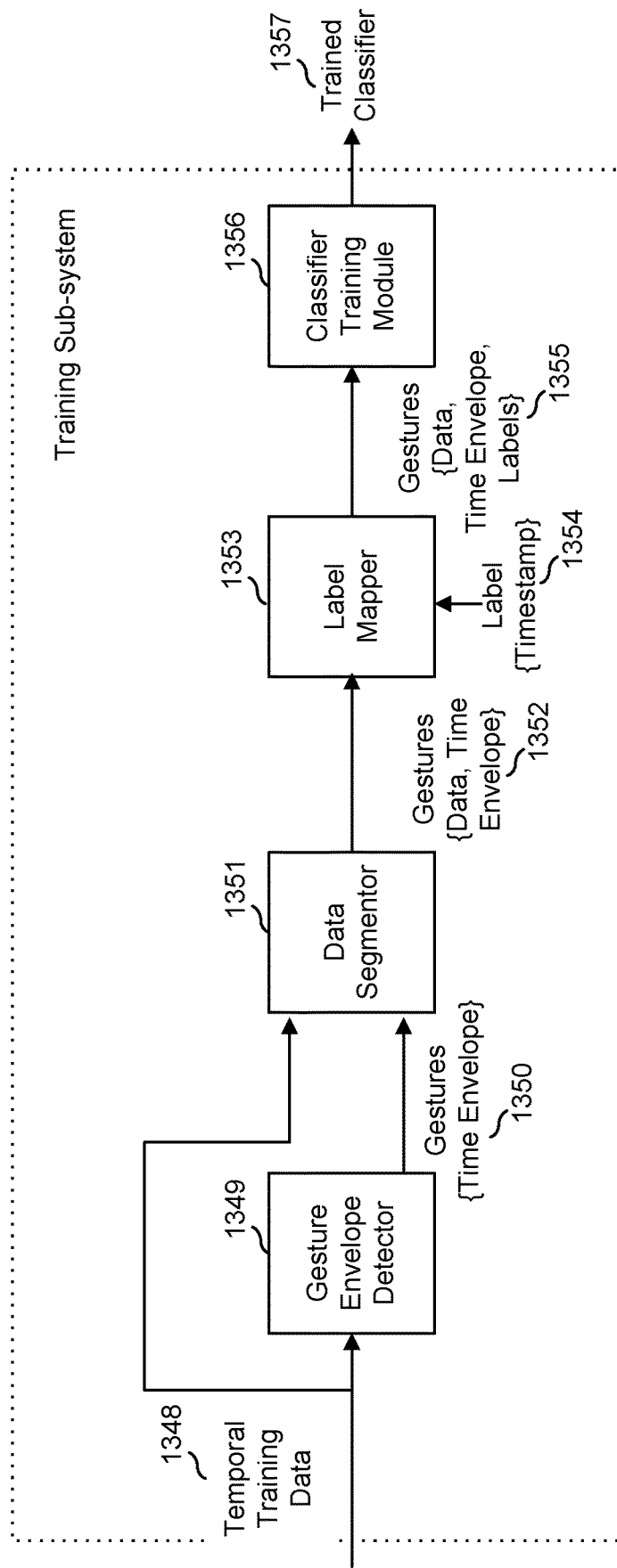
FIG. 13 shows an example of a training subsystem for an unsupervised classification system in accordance with at least one embodiment of the present disclosure.

FIG. 13 shows an illustrative example of a classifier training subsystem in accordance with at least one embodiment of the present disclosure where the classifier training module is based on statistical deep learning algorithms for unsupervised classification.

Gesture envelope detector 1349 computes gestures 1350 with corresponding gesture time envelopes from temporal training data 1348. Data segmenter 1351 assigns the proper data segment or data segments to each gesture based on information in the gesture time envelope. As an example, data segmenter 1351 may look at the start and end time information in the gesture time envelope and assign one or more data segments that correspond to the overall gesture duration. This is just one example. Data segments may be selected based on different segments or sub-segments defined by the gesture time envelope. Data segments could also be selected based on time segments that are outside of the gesture time envelope but directly or indirectly related to the gesture time envelope. An example could be selection of data segments corresponding to a period of time immediately preceding the start of the gesture time envelope or selection of data segments corresponding to a period of time immediately following the end of the gesture time envelope. Other examples of time segments that are outside the gesture time envelope but directly or indirectly related to the gesture time envelope are also possible.

Gestures including data segments, gesture time envelope information and labels are fed into classifier training module 1356. In some embodiments of the present disclosure, only a subset of the gesture time envelope information may be fed into classifier training module 1356. In some embodiments of the present disclosure, gesture time envelope information may be processed before it is being applied to classifier training module 1356. One example could be to make the time reference of the gesture time envelope align with the start of the data segment, rather than with the time base of the original temporal training data stream. Other examples are also possible. By adding time envelope information that further characterizes the data segments, the performance of the classifier training module may be improved.

For example, in case of gesture recognition of eating gestures based on motion sensor data inputs, feeding additional anchor time information such as the time when the pitch angle, roll or yaw reaches a maximum or minimum into the classifier training module can improve the performance of a trained classifier 1357 as trained classifier 1357 can analyze the training data and look for features and correlations specifically around said anchor times. Other examples of time envelope information that can be fed into the classifier training module are also possible.

Figure 14:
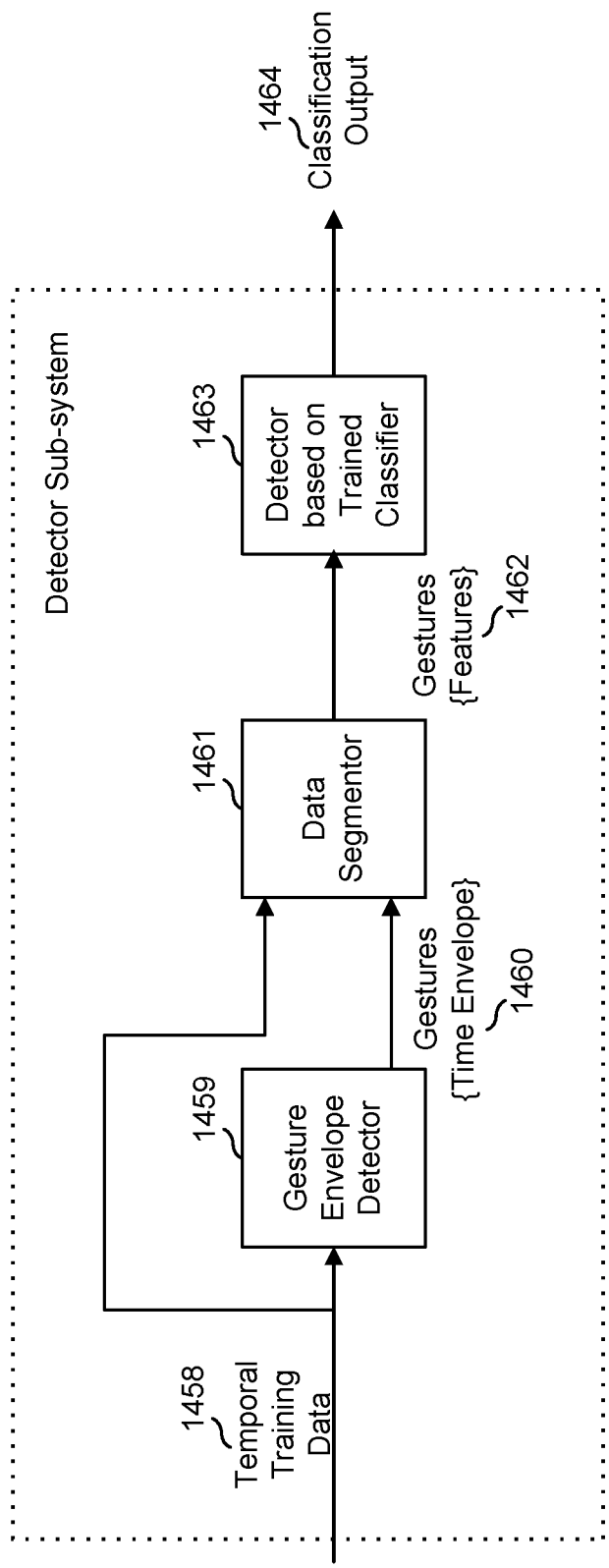
FIG. 14 shows an example of a detector subsystem for an unsupervised classification system in accordance with at least one embodiment of the present disclosure.

FIG. 14 shows an illustrative example of a classification detector subsystem in accordance with at least one embodiment of the present disclosure that could be used in combination with classification training subsystem of FIG. 13.

Classifier Ensemble

Figure 15:
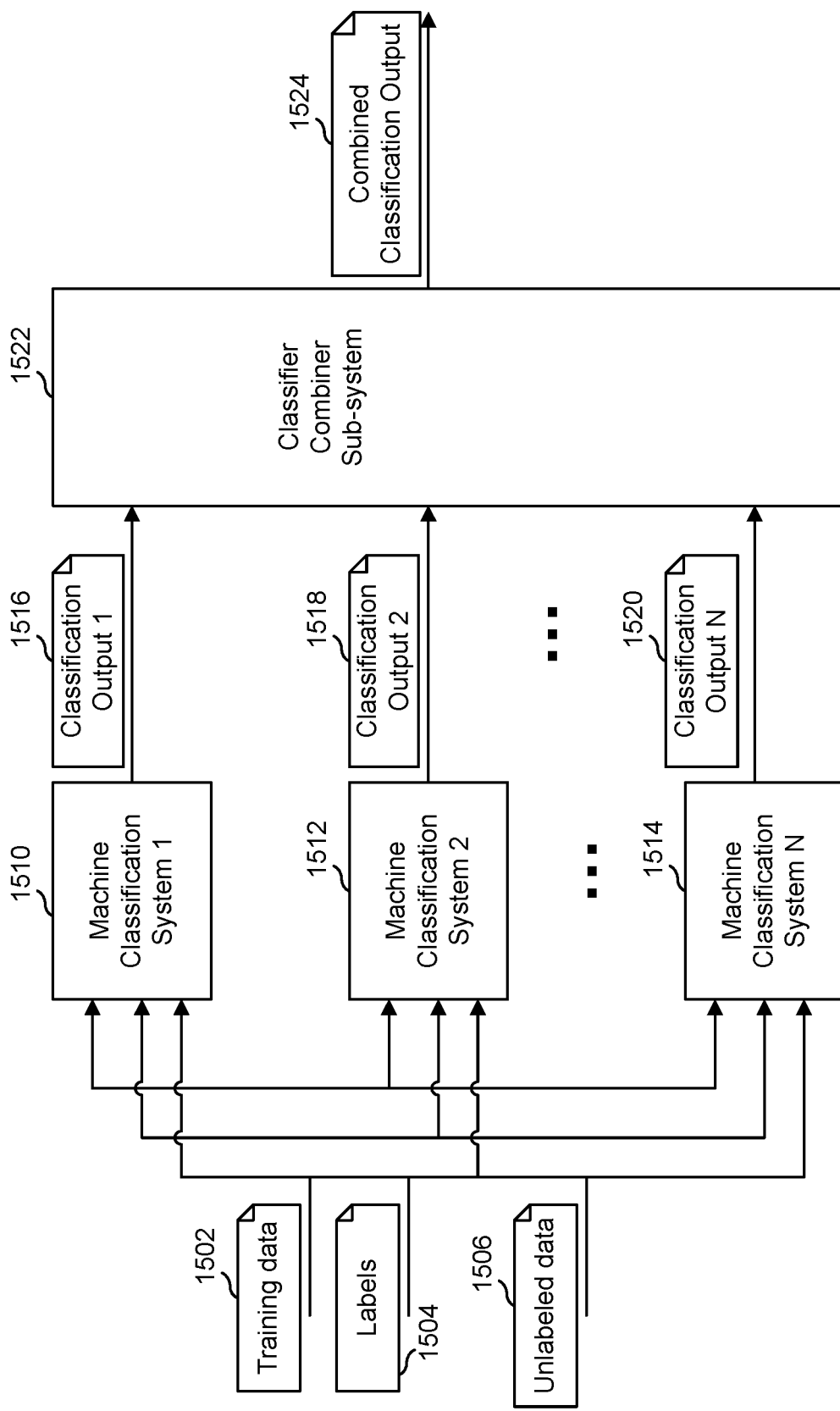
FIG. 15 shows an example of a classifier ensemble system.

In some embodiments, multiple parallel classification systems based on gesture envelope detection may be used. An example of a system with multiple parallel classifiers is shown in FIG. 15. The number of parallel classification systems may vary. Each classification system 1510, 1512, 1514 has its own training and detector sub-system and performs gesture envelope detection on a different subset of the training data 1502 and labels 1504 inputs to detect gestures, or may use different thresholds or criteria to qualify gestures. Consequently, each individual gesture envelope detector will generate an independent set of gestures each with different gesture time envelopes. The feature generator logic of each classification system creates features for the gestures created by its corresponding gesture envelope detector logic. The features may be different for each classification system. The classifier model used by each of the parallel classifiers may be the same or different, or some may be the same and others may be different. Since the gesture time envelopes and features used for training of each classifier model are different, the parallel classification systems will produce different Classification Outputs 1516, 1518, 1520.

The Classification Outputs 1516, 1518, 1520 of each classification system may be fed into Classifier Combiner sub-system 1522. Classifier Combiner sub-system 1522 may combine and weigh the Classification Outputs 1516, 1518, 1520 of the individual classification systems 1510, 1512, 1514 to produce a single, overall Classification result, Combined Classification Output 1524. The weighing may be static or dynamic. For example, in case of gesture recognition, certain classifiers may perform better at correctly predicting the gestures of one group of people, whereas other classifiers may perform better at correctly predicting the gestures of another group of people. Classifier Combiner sub-system 1522 may use different weights for different users or for different contextual conditions to improve the performance of the overall classifier ensemble. The trained system can then be used to process unlabeled data 1506.

Other examples of temporal problems include but are not limited to autonomous driving, driver warning systems (that alert the driver when dangerous traffic conditions are detected), driver alertness detection, speech recognition, video classification (security camera monitoring, etc.) and weather pattern identification.

Ignoring the temporal nature of the data inputs as well as any features that are linked to the temporal envelope of the data inputs can limit performance of the classifier and make the classifier non-suitable for classification tasks where a reliable detection depends on features that are inherently linked to segments of the variable time envelope or to the overall variable time envelope. Performance and usability can break down if a proper time period cannot be determined reliably, or where the time period varies from gesture-to-gesture, from person-to-person etc.

As described herein, improved methods frame temporal problems with a variable time envelope, so that information tied to the overall variable time envelope or to segments thereof can be extracted and included in the feature set used to train the classifier. The proposed improved methods improve performance and reduce the amount of training data needed since features can be defined relative to the time bounds of the variable time envelope, thereby reducing sensitivities to time and user variances.

In addition to finding time envelopes for gestures, the system can also find event time envelopes. In such an approach, the system might determine a gesture and a gesture envelope, but then do so for additional gestures and then define an event envelope, such as the start and end of an eating event.

Context to Improve Overall Accuracy

Figure 16:
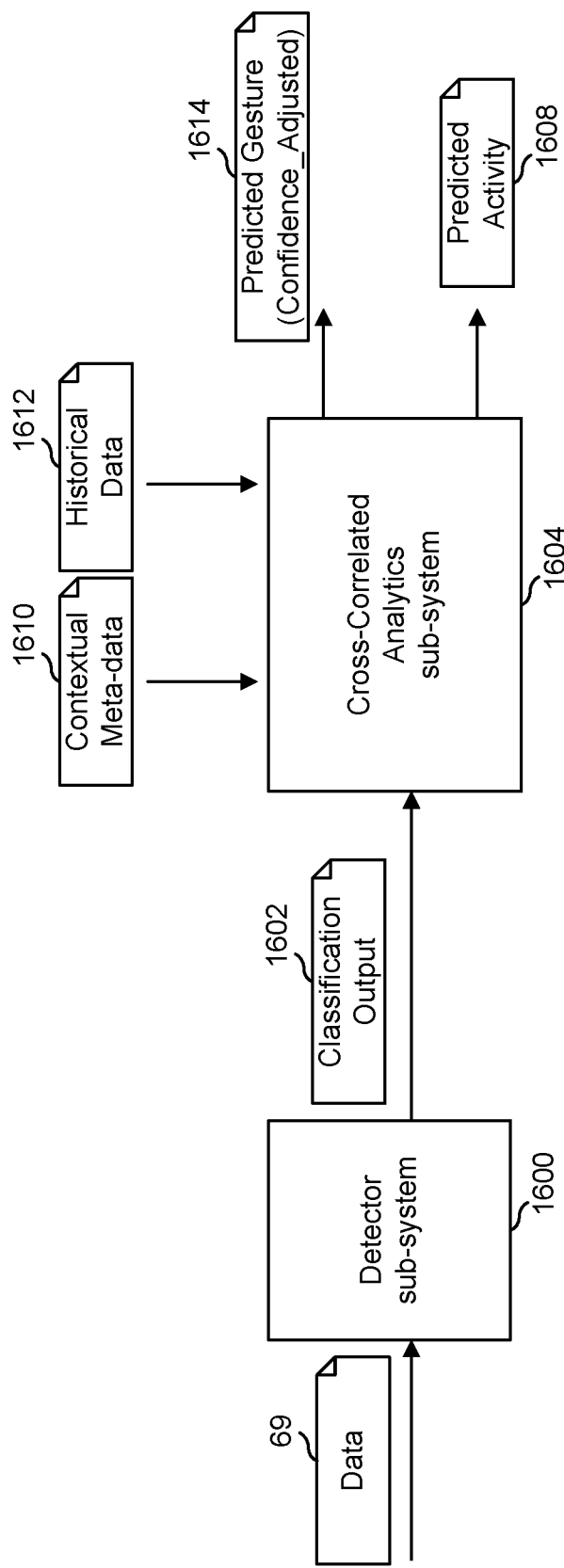
FIG. 16 shows an example of a machine classification system that includes a cross-correlated analytics sub-system.

FIG. 16 shows an example of a machine classification system that includes a cross-correlated analytics sub-system. Classification output 1602 may be fed into cross-correlated analytics sub-system 1604. Cross-correlated analytics sub-system 1604 can make adjustments based one or more contextual clues to improve the accuracy. In the example of gesture recognition, an example of a contextual clue could be the proximity in time to other predicted gestures. For example, eating gestures tend to be grouped together in time as part of an eating activity such as a meal or a snack. As one example, Cross-correlated analytics sub-system 1604 could increase the confidence level that a predicted gesture is an eating gesture based on the confidence level and degree of proximity of nearby predictions.

In another embodiment, cross-correlated analytics sub-system 1604 may take individual predicted gestures 1614 from classification output 1602 as inputs and may cluster individual predicted gestures into predicted activities 1608. For example, cross-correlated analytics sub-system 1604 may map multiple bite gestures to an eating activity such as a snack or a meal. Likewise, cross-correlated analytics sub-system 1604 could map multiple sip gestures to a drinking activity. Other examples of activity prediction based on gesture clustering are also possible. Cross-correlated analytics sub-system 1604 may modify the confidence level of a predicted gesture based on the temporal spacing and sequence of predicted activities. As an example, Cross-correlated analytics sub-system 1604 could decrease the confidence level that a predicted gesture is an eating gesture if it is detected shortly following or amid a "brushing teeth" activity. In another example, Cross-correlated analytics sub-system 1604 could decrease the confidence level that a predicted gesture is a drinking gesture if it is detected during or shortly after a brushing teeth activity. In this case, Cross-correlated analytics sub-system 1604 could decide to increase the confidence level that the gesture is a rinsing gesture.

Cross-correlated analytics sub-system 1604 can adjust a classification output of a predicted gesture based on historical information 1612 or other non-gesture meta-data 1610 information such as location, date and time, other biometric inputs, calendar or phone call activity information. For example, Cross-correlated analytics sub-system 1604 may increase the confidence level that a predicted gesture is an eating gesture or a predicted activity is an eating activity if GPS coordinates indicate that the person is at a restaurant. In another example, Cross-correlated analytics sub-system 1604 may increase the confidence level that a predicted gesture is an eating gesture or a predicted activity is an eating activity if it occurs at a time of day for which past behavior indicates that the user typically engages in eating at this time of the day. In yet another example of the present disclosure, cross-correlated analytics sub-system 1604 may increase the confidence level that a predicted gesture is an eating gesture or that a predicted activity is an eating activity if the predicted gesture or predicted activity is preceding or following a calendar event or phone call conversation if past behavior indicates that the user typically eats preceding or following similar calendar events (e.g., with same attendee(s), at certain location, with certain meeting agenda, etc.) or phone call conversation (e.g., from specific phone number). While the above examples reference eating, it will be apparent to one skilled in the art that this could also be applied to gestures other than eating. In the general case, the machine classifier with cross-correlated analytics sub-system uses contextual clues, historical information and insights from proximity sensing in time to improve accuracy, where the specific contextual clues, historical information and insights from proximity sensing in time and how they are applied is determined by methods disclosed or suggested herein.

In some embodiments of the present disclosure, Classification Output 1602 may include additional features or gesture time envelope information. Cross-correlated analytics sub-system 1604 may process such additional features or gesture time envelope information to determine or extract additional characteristics of the gesture or activity. As an example, in one embodiment of the present disclosure, Cross-correlated analytics sub-system 1604 derives the estimated duration of the drinking gesture from the gesture time envelope and this information can be used by cross-correlated analytics sub-system 1604 or by one or more systems that are external to the machine classifier system to estimate the fluid intake associated with the drinking gesture.

In another embodiment, Cross-correlated analytics sub-system 1604 may derive the estimated duration of an eating gesture from the gesture time envelope and this information may be used by the cross-correlated analytics sub-system 1604 or by one or more systems that are external to the machine classifier system to estimate the size of the bite associated with the eating gesture. Cross-correlated analytics sub-system 1604 may combine the predicted drinking gestures with other sensor data to predict more accurately if someone is consuming a drink that contains alcohol and estimate the amount of alcohol consumed. Examples of other sensor data may include but are not limited to measuring hand vibration, heart rate, voice analysis, skin temperature, measuring blood, breath chemistry or body chemistry.

Detector sub-system 1600 may predict a specific eating or drinking method and cross-correlated analytics sub-system 1604 may combine the information obtained from detector sub-system 1600 about specifics of the eating or drinking method with additional meta-data to estimate the content, the healthiness or the caloric intake of the food. Examples of eating/drinking methods may include but are not limited to eating with fork, eating with knife, eating with spoon, eating with fingers, drinking from glass, drinking from cup, drinking from straw, etc.). Examples of meta-data may include but are not limited to time of day, location, environmental or social factors.

Another Example Embodiment

Figure 17:
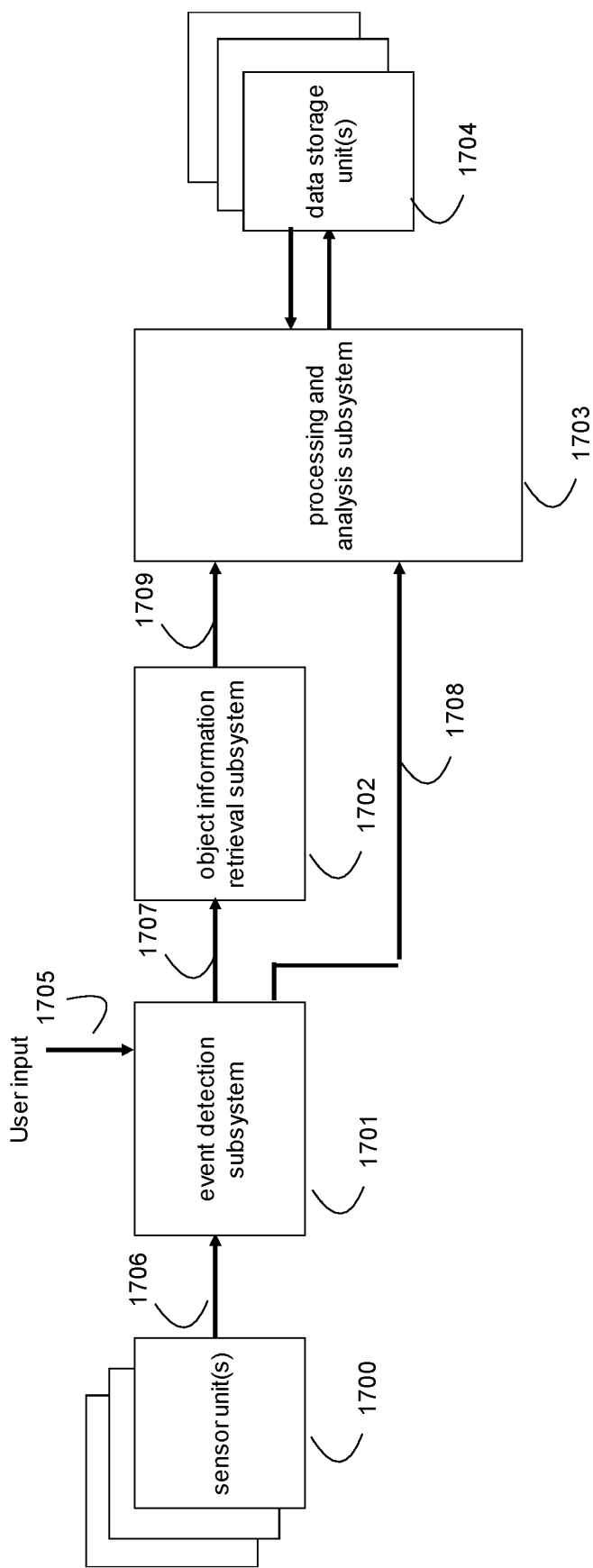
FIG. 17 shows a high level functional diagram of a monitoring system of a variation similar to that of FIG. 1, in accordance with an embodiment.

FIG. 17 shows a high level functional diagram of a monitoring system of a variation similar to that of FIG. 1, in accordance with an embodiment. As shown in FIG. 17, sensor units 1700 interact with an event detection subsystem 1701 that in turn interacts with an object information retrieval subsystem 1702, and that provide inputs to a processing and analysis system, the results of which can be stored in data storage units 1704.

In some embodiments, elements shown in FIG. 17 are implemented in electronic hardware, while in others some elements are implemented in software and executed by a processor. Some functions might share hardware and processor/memory resources and some functions might be distributed. Functionality might be fully implemented in a sensor device such as wrist worn wearable device, or functionality might be implemented across the sensor device, a processing system that the sensor device communicates with, such as a smartphone, and/or a server system that handles some functionality remote from the sensor device. For example, a wearable sensor device might make measurements and communicate them to a mobile device, which may process the data received from the wearable sensor device and use that information possibly combined with other data inputs, to activate object information retrieval subsystem 1702. Object information retrieval subsystem 1702 may be implemented on the mobile device, on the wearable sensor device, or on another electronic device. The object information retrieval subsystem 1702 may also be distributed across multiple devices such as for example across the mobile device and the wearable sensor device. Data or other information may be stored in a suitable format, distributed over multiple locations or centrally stored, in the form recorded, or after some level of processing. Data may be stored temporarily or permanently. Data may be stored locally on the wearable sensor device, on the mobile device or may be uploaded over the Internet to a server.

A first component of the system illustrated in FIG. 17 is the event detection subsystem 1701. One role of event detection subsystem 1701 is to identify the actual, probable or imminent occurrence of an event. An event could, for example, be an event related to a specific activity or behavior. Specific activities or behaviors may include, but are not limited to, eating, drinking, smoking, taking medication, brushing teeth, flossing, hand washing, putting on lipstick or mascara, shaving, making coffee, cooking, urinating, using the bathroom, driving, exercising or engaging in a specific sports activity. Other examples of an event that may be detected by event detection subsystem 1701 could be an operator on a production line or elsewhere performing a specific task or executing a specific procedure. Yet another example could be a robot or robotic arm performing a specific task or executing a specific procedure on a production arm or elsewhere.

The event detection subsystem may use inputs from one or more sensor units 1700, other user inputs 1705, or a combination of one or more sensor inputs from sensor unit 1700 and one or more other user inputs 1705 to determine or infer the actual, probable or imminent occurrence of an event. The event detection subsystem 1701 may do additional processing on the sensor and/or user inputs to determine the actual, probable or imminent occurrence of an event. In general, the event detection system records and/or reacts to an inferred event, which occurs when the event detection system has inputs and/or data from which it determines that an event might actually be starting, might likely start, or is imminent. In some cases, the event detection system might infer an event where an event did not actually occur and process it as an event, but this might be an infrequent occurrence.

The event detection subsystem 1701 may also do additional processing on the sensor and/or user inputs to determine additional information about the event. Such information may include, but is not limited to, the duration of the event, the event start time, the event end time, metrics associated with the speed or pace at which subject is engaging in the event. Other event data elements are also possible. For example, if the event is an eating event, an event data element could be the number of bites or the amount of food consumed. Similarly, if the event is a drinking event, an event data element could be the number of sips or the amount of fluid intake. These event data elements might be stored in a database that maintains data elements about inferred events.

Using the gesture sensing technology, an event detection system can trigger and external device to gather further information.

In a specific embodiment, the electronic device that houses object information retrieval subsystem 1702 or a portion of object information retrieval subsystem 1702 includes Near-Field-Communication (NFC) technology and the object information retrieval subsystem 1702 obtains information about the object(s) or subject(s) with which the subject may be interacting at least in part via transmission over a wireless NFC link.

In a specific embodiment, the external device is a NFC reader and various objects having NFC tags thereon are detected. The NFC reader might be integrated with the gesture sensing technology or with some components of the gesture sensing technology.

Where those objects are food/beverage related, the event detection system can determine what the gestures are related to. For example, food/beverage containers might have NFC tags embedded in the product packaging and a food intake monitoring system might automatically determine that gestures are related to an eating event, then signal to an NFC reader to turn on and read nearby NFC tags, thereby reading the NFC tags on the products being consumed so that the gestures and the event are associated with a specific product.

In an example, a monitoring system might have a wearable device that determines gestures and based on those gestures, identifies an eating event or a drinking event. Suppose a drinking event is detected and based on the sensor inputs and gestures detected, the monitoring system determined that the user drank three quarters of a can of soda, such as be counting sips and estimating or computing the size of each sip. As the gestures are likely identical regardless of whether it is a diet soda or a regular soda. Using the NFC reader, the specific brand and type of soda can be detected as well.

The sensors may be in the wearable device, with gesture determination logic or processing occurring in an external device that is communicatively coupled to the wearable device, such as a mobile phone, or the gesture determination may partially happen on the wearable device and partially on the external device that is communicatively coupled to the wearable device.

The NFC reader may be in the wearable device that houses the sensors, in an external device that is communicatively coupled to the wearable device and that performs at least some of the gesture determination or in another external device that is communicatively coupled to the wearable device, to an external device that performs at least some of the gesture determination or to both.

In the general case, the detection of the occurrence of an event may be used to initiate a process/system/circuitry/device to collect information about objects/items or other subjects that are being interacted with by the person performing the activity or behavior represented by the event. This information may be recorded in the form of data elements. Object data elements may be stored in a database. One or more object data elements and one or more event data elements of the same event may be recorded as a single entry in a database. Object data elements and event data elements may also be recorded as separate entries in a database. Other data structures consistent with the teachings herein might also be used, or used instead.

When the NFC reader system gets activated, it initiates one or more NFC read commands, and additional information from relevant objects is obtained wirelessly over NFC link. Additional processing may be applied, such as filtering out the NFC data to simplify processing downstream.

In other variations, other wireless links are used instead of NFC or with NFC. Examples of other wireless technologies include but are not limited to Bluetooth, Bluetooth Low Energy, Wi-Fi, Wi-Fi derivatives, and proprietary wireless technologies.

The detection of occurrence of an event signal may be used to filter out information about specific, relevant objects that are related to the activity/behavior of interest that are part of the event.

While the object detection process might be automatic, it can also have user intervention required to activate the object information retrieval system. For example, it could be as simple as asking the user to turn on a camera, or make a decision whether to continue the detection process and get the user's input on the decision. As another example, the user may be prompted to move the NFC reader closer to the NFC tag of interest. In another example, the user may be prompted to activate the NFC reader circuitry, or portions of the NFC reader circuitry or take one or more actions that allow the NFC reader circuitry to issue read command.

In addition to an NFC reader, a camera might be activated and additional information from relevant objects is obtainable by analyzing images or video recording of relevant objects. The camera might be combined in a unit with the NFC reader. In some embodiments, only a camera is used, or other ancillary sensors are used to obtain additional information about the event.

Information about the activity or behavior that are part of the event, obtained from the event detection subsystem can be combined with information about the object(s) or subject(s) the user is interacting with, and additional processing/analysis may be performed on the combined dataset to obtain additional information or insights about the activity/behavior that cannot be obtained from looking at only one of the data sources alone.

While many examples in this disclosure refer to the event detection system analyzing gestures to detect the actual, likely or imminent occurrence of an event, other sensor inputs are also possible. For example, audio signals in or near the mouth, throat or chest may be used to detect and obtain information about a user's consumption. To accomplish this, the event detection subsystem 1701 may use inputs 1706 from one or more sensor units 1700. Sensors may include, but are not limited to, accelerometers, gyroscopes, magnetometers, magnetic angular rate and gravity (MARG) sensors, image sensors, cameras, optical sensors, proximity sensors, pressure sensors, odor sensors, gas sensors, glucose sensors, heart rate sensors, ECG sensors, thermometers, light meters, Global Positioning Systems (GPS), and microphones.

Upon the detection of an actual, probable or imminent occurrence of an event, the event detection subsystem may activate the object information retrieval subsystem 1702. Alternatively, the event detection subsystem 1701 may do additional processing to decide whether or not to activate the object information retrieval subsystem 1702. The event detection subsystem 1701 may activate the object information retrieval subsystem 1702 immediately or wait for a certain time before activating the object information retrieval subsystem 1702.

The role of object information retrieval subsystem 1702 is to collect information about objects or other subjects a subject is interacting with when or some time after the event detection subsystem 1701 has detected the occurrence of an actual, probable or imminent event.

In one such embodiment, upon receiving an activation input signal 1707 from event detection subsystem 1701, or some time after receiving an activation input signal 1707, object information retrieval subsystem 1702 initiates an NFC read action to read the NFC tag attached to, housed within or otherwise associated with one or more objects that are within NFC range of the device that houses object information retrieval subsystem 1702. Object information retrieval subsystem 1702 sends the data received from one or more objects to processing and analysis subsystem 1703. Object information retrieval subsystem 1702 may do additional processing on the data before sending it to processing and analysis subsystem 1703. In other embodiments, additional ancillary sensors or sensor systems might be used, such as a camera or other electronic device.

Processing may include but is not limited to filtering, extracting specific data elements, modifying data or data elements, combining data or data elements obtained from multiple objects, combing data or data elements with data obtained from other sources not collected via NFC. Examples of filtering may include but are not limited to filtering based on distance or estimated distance between the object or objects and object information retrieval subsystem, based on signal strength of received NFC signals, based on order in which data is received from objects, based on information in the data or in specific data elements. Other filtering mechanisms or criteria used for filtering are also possible. Object information retrieval subsystem 1702 may stop reading NFC tags after a fixed time, after a configurable time, after reading a fixed or configurable number of tags. Other criteria may also be used.

It is also possible, that the object information retrieval subsystem collects information about objects or other subjects a subject is interacting with independent of the event detection subsystem. In such an embodiment, the processing and analysis subsystem 1703 may use signals 1708 received from event detection subsystem 1701 with data signals 1709 received from object information retrieval subsystem 1702 to deduce relevant information about objects or other subjects a subject may be interacting during an activity or when exhibiting a certain behavior.

In a specific embodiment of this disclosure, object information retrieval subsystem 1702 continuously, periodically or otherwise independently from inputs from event detection subsystem 1701 reads NFC tags from object that are within range of the electronic device that houses object information retrieval subsystem 1702 in its entirety or in part. The detection of occurrence of an activity/behavior signal may be used to filter out information about specific, relevant objects that are related to the activity/behavior of interest. Where the objects are associated with an event, indications of, or references to, the specific objects might be recorded as part of a record of the event, so that the information can be later used for filtering or other processing.

In a specific embodiment, object information retrieval subsystem 1702 collects data independent from inputs it receives from the event detection subsystem but only sends data to processing and analysis subsystem 1703 when or some time after, it receives an activation input signal 1707 from event detection subsystem 1701. Object information retrieval subsystem 1702 may send only a subset of the data it has received from objects over an NFC link. For example, it may only send data that it receives in a fixed or configurable time window related to the time it receives the activation input signal 1707. For example, it may only send data immediately preceding and/or immediately following the activation input signal 1707. Other time windows are also possible. Object information retrieval subsystem 1702 may do additional processing on the data before sending it to processing and analysis subsystem 1703.

In one embodiment of this disclosure, the object information retrieval subsystem 1702 includes a camera and the information about the object or objects may be derived from the analysis of an image or video recording.

In a preferred embodiment of this disclosure, object information retrieval subsystem 1702 collects data from objects without any intervention or input from the subject. In another embodiment of this disclosure, some user input or intervention is required. For example, the user may be prompted to move the NFC reader closer to the NFC tag of interest. In another example, the user may be prompted to activate the NFC reader circuitry, or portions of the NFC reader circuitry or take one or more actions that allow the NFC reader circuitry to issue read command.

Figure 18:
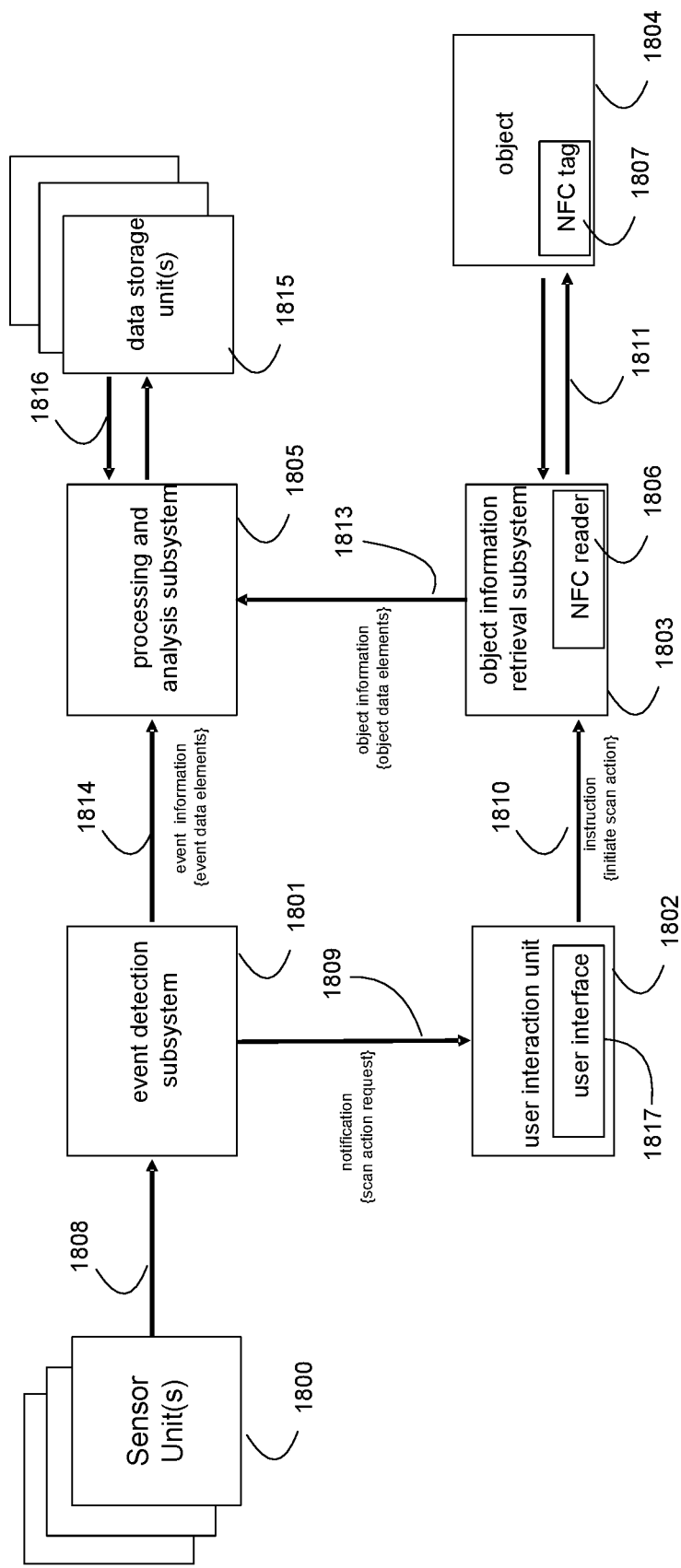
FIG. 18 shows a high level functional diagram of a monitoring system in accordance with an embodiment that requires user intervention.

FIG. 18 shows a high level functional diagram of a monitoring system in accordance with an embodiment that requires user intervention. As shown in FIG. 18, one or more sensor units 1800 interact with event detection subsystem 1801 and send sensor data to event detection subsystem 1801. Upon detection or inference of an actual, probable or imminent event, event detection subsystem sends one or more notifications to user interaction unit 1802 to request activation of NFC scan action. Notifications may be rendered to the user as a displayed text message, as a displayed image, as an audio message, as a LED signal, as a vibration, etc. A combination of user interfaces may also be used. Other user interface may also be used. The user may respond to the notification(s) using one or more user interfaces of the user interaction unit 1802. A user response may trigger user interaction unit 1802 to send a scan command 1810 to object information retrieval subsystem 1803. Upon receiving scan command 1810 or some time after receiving scan command 1810, object information retrieval subsystem 1803 may activate NFC reader 1806 and obtain information about object 1804 over a wireless communication link 1811 between NFC reader 1806 and NFC tag 1807. Information obtained over wireless link 1811 may contain information about brand, type, content, expiration date, lot number, etc. of object 1804. Other information about the object may also be retrieved. Event data elements 1814 from event detection subsystem 1801 and object data elements 1813 retrieved by object information retrieval subsystem 1803 from one or more objects over a wireless link 1811 may be sent to processing and analysis subsystem 1805. Additional processing may be performed and the event and object data elements may be stored in a database on one or more data storage units 1815.

In another example, the event detection system automatically scans for NFC tags, but upon receiving data from an object, the object information retrieval subsystem sends a message to the subject and the subject authorizes, or not, transmission to a processor or analysis subsystem or the subject confirms the information directly. This message may also be sent by processing and analysis subsystem.

Processing by processing and analysis subsystem 1805 may include but is not limited to filtering, extracting specific data elements, modifying data or data elements, combining data or data elements obtained from multiple objects, combing data or data elements with data obtained from other sources not collected via NFC. Examples of filtering may include but are not limited to filtering based on distance or estimated distance between object or objects and object information retrieval subsystem, based on signal strength of received NFC signals, based on order in which data is received from objects, based on information in the data or in specific data elements. Other filtering mechanisms or criteria used for filtering are also possible. Object information retrieval subsystem 1803 may stop sending data after a fixed time, after a configurable time, after reading a fixed or configurable number of tags. Other criteria may also be used. Object information retrieval subsystem 1803 may send data only from a single object, from a subset of objects or from all objects for which it receives data within the specified time window.

In a different embodiment of this disclosure, object information retrieval subsystem 1803 continuously, periodically or otherwise independently from inputs from event detection subsystem 1801 reads NFC tags from object that are within range of the electronic device that houses object information retrieval subsystem 1803 in its entirety or in part and sends such data to processing and analysis subsystem 1805 independent of any signals from event detection subsystem.

Processing and analysis subsystem 1805 receives data inputs from event detection subsystem 1801 and object information retrieval subsystem 1803. It is also possible that processing and analysis subsystem 1805 receives inputs only from object information retrieval subsystem 1803. Processing and analysis subsystem 1805 may do additional processing on the data and analyze the data to extract information about the object(s) or subject(s) from the data it receives. Processing may include but is not limited to filtering, extracting specific data elements, modifying data or data elements, combining data or data elements obtained from multiple objects. Analysis may also include comparing specific data elements to data that is stored in a look up table or database, correlating data elements to data elements that were obtained at an earlier time and/or from different subjects. Other processing and analysis steps are also possible. Processing and analysis subsystem 1805 may store raw or processed data in data storage unit(s) 1804. Storage may be temporary or permanent.

In some embodiments, the outputs from processing and analysis subsystem 1805 may be available in real-time, either during or shortly after the event. In other embodiments, the outputs may not be available until a later time.

Processing and analysis subsystem 1805 may be implemented on the mobile device, on the wearable sensor device, or on another electronic device. Processing and analysis subsystem 1805 may also be distributed across multiple devices such as for example across the mobile device and the wearable sensor device. In another example, processing and analysis subsystem 1805 may be distributed across the mobile device and a local or remote server. Processing and analysis subsystem 1805 may also all be implemented on a local or remote server. Information may be stored in a suitable format, distributed over multiple locations or centrally stored, in the form recorded, or after some level of processing. Data may be stored temporarily or permanently. Data may be stored locally on the wearable sensor device, on the mobile device or may be uploaded over the Internet to a server.

The object information retrieval subsystem may be housed in its entirety or in part inside a battery operated electronic device and it may desirable to minimize the power consumption of the object information retrieval subsystem. When no event is detected, the radio circuitry (e.g., the NFC reader circuitry) may be placed in a low power state. Upon detection or inference of an actual, probable or imminent occurrence of an event, the object information retrieval subsystem may be placed in a higher power state. One or more additional circuitry inside the object information retrieval subsystem may be powered up to activate the object information retrieval subsystem, to improve the range or performance of object information retrieval subsystem, etc. In one specific example, the NFC reader is disabled or placed in a low power standby or sleep mode when no event is detected. Upon detection or inference of an event, the NFC reader is placed in a higher power state in which it can communicate with NFC tags of neighboring objects. After reading a pre-configured number of NFC tags, after a pre-configured time or upon detection of the end or completion of the event, the NFC reader may be disabled again or may be placed back into a low power standby or sleep mode.

Medication Dispensing System Examples

A system according to the principles and details described herein might be used to detect onset of eating/drinking to start administering doses of insulin as a form of insulin therapy and/or a meal-aware artificial pancreas. An insulin dosage calculator can take into account glucose level at start of eating, a first or higher order derivative of the glucose level at start of eating to determine dosage and timing of insulin delivery. Insulin may be delivered at once, in multiple doses or in micro-doses. If additional information about food is obtained from object information retrieval subsystem (e.g., drinking a can of regular soda versus diet soda), this information may be taken into account by the insulin dosage calculator. For example, if a food item with high sugar content is being consumed, the insulin dosage calculator may increase the dosage administered per micro-dosing event or may increase the number of micro-doses being delivered in a given period of time.

Figure 19:
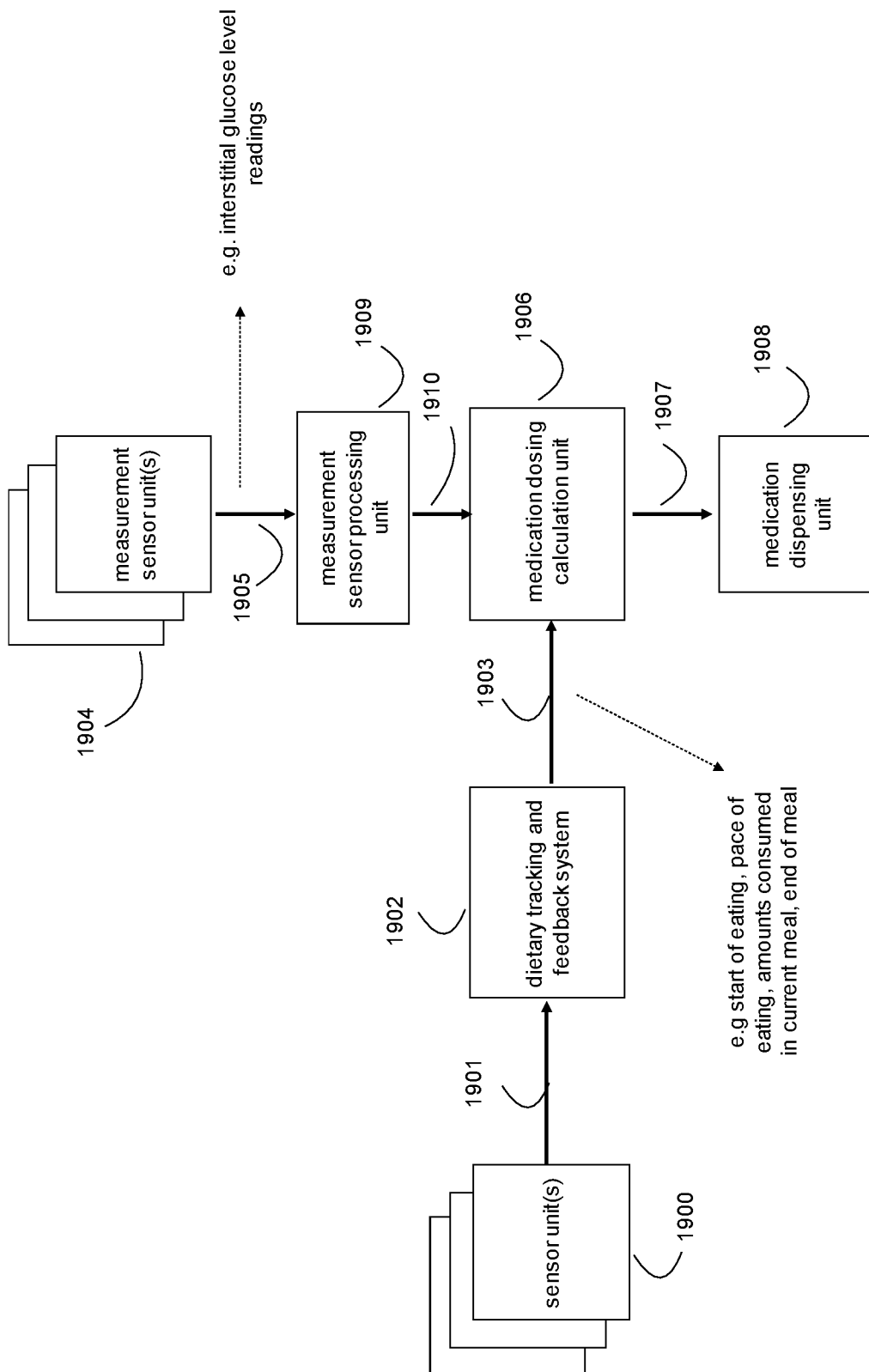
FIG. 19 shows a high level functional diagram of a medication dispensing system.

FIG. 19 shows a high level functional diagram of a medication dispensing system covered by the current disclosure. A medication dispensing system may in part include one or more of the following: a dietary tracking and feedback system 1902, one or more sensors or sensor units 1900, a measurement sensor processing unit 1909, a medication dosing calculation unit 1906, one or more measurement sensor units 1904 and a medication dispensing unit 1908.

In one embodiment of the current disclosure, the medication to be administered is insulin, the measurement sensor unit 1904 is a continuous glucose monitor sensor that measures interstitial glucose levels, medication dispensing unit 1908 is an insulin pump and medication dosing calculation unit 1906 is the insulin dosage computation unit of an automated insulin delivery system (a.k.a., artificial pancreas).

Each of the elements shown in FIG. 19 might be implemented by suitable structure. For example, these could be individual hardware elements or implemented as software structures in a wearable device, an ancillary device that communicates with a wearable device, or a server coupled over a network to the ancillary device and/or a wearable device. Some elements might be entirely software and coupled to other elements that are able to send and/or receive messages to or from the processor executing the software. For example, medication dispensing unit 1908 might be an embedded hardware system that injects doses or micro-doses of medication in response to instructions given by a software system and thus would only require minimal processing on-board. It is also possible that medication dosing calculation unit 1906 and medication dispensing unit 1908 are housed in the same hardware. Certain elements of FIG. 19 may be distributed across multiple software and or hardware elements. As an example, a portion of medication dosing calculation unit 1906 may be implemented on one electronic device that is separate from the electronic device that houses medication dispensing unit 1908, whereas another portion of medication dosing calculation unit 1906 may be embedded within the same housing as medication dispensing unit 1908.

Dietary tracking and feedback system 1902 may be implemented as described elsewhere herein and may monitor the outputs of one or more sensor unit(s) to determine the actual, probable or imminent start of a food intake event. Upon detection of an actual, probably or imminent start of a food intake event, or some time thereafter, it may send a signal 1903 to medication dosing calculation unit 1906 to inform medication dosing calculation unit 1906 that an actual, probable or imminent start of a food intake event has been detected. Medication dosing calculation unit 1906 may use this information to change its state to an "imminent meal", "probable meal" or "meal-in-progress" state.

Upon entering the imminent meal, probable meal or meal-in-progress state or some time thereafter, medication dosing calculation unit 1906 may calculate an initial meal medication dosage to be administered and send one or more messages to medication dispensing unit 1908. Alternatively or additionally, it may also alter one or more other parameters such as the target glucose level in response to the detection and signaling of an imminent, probable or actual start and/or progress of a food intake event. Alternatively, the medication dosage to be administered in connection with the start and/or progress of a food intake event may have been pre-configured or calculated ahead of the occurrence of the food intake event. Upon receiving those messages 1907, medication dispensing unit 1908 may initiate delivery of the medication.

The medication dispensing unit may deliver the medication all at ones or according to a delivery schedule. The delivery schedule may be determined and communicated to the insulin delivery system by the medication dosing calculation unit. The delivery schedule may be determined upon entering the meal-in-progress state or some time thereafter. The delivery schedule may also be pre-configured ahead of the occurrence of the food intake event.

The initial meal medication dosage and/or delivery schedule may cover the entire anticipated medication dosage for the food intake event. Alternatively, the initial meal medication dosage and/or delivery schedule may only cover a portion of the entire anticipated medication dosage for the food intake event, and additional medication dosages are expected at a later time during or after the food intake event.

Medication dosing calculation unit 1906 may take into account additional inputs when calculating an initial medication dosage and or initial delivery schedule. Some inputs may be related to current or recent measurements, current or recent user activities and behaviors or other information corresponding to a current or recent state or condition of a user. Other inputs may be related to historical measurements, historical user activities and behaviors or other information corresponding to a past state or condition of a user.

Examples of Additional Inputs

Medication dosing calculation unit 1906 may take into account one or more outputs 1910 from measurement sensor processing unit 1909. Medication dosing calculation unit 1906 may perform additional processing steps on outputs 1910. For example, measurement sensor unit 1904 may be a continuous glucose monitor ("CGM"), and outputs 1910 of measurement sensor processing unit 1909 may be interstitial glucose level readings. Outputs 1910 may for example be updated every couple of minutes. Other update frequencies are also possible. Outputs 1910 may also be updated continuously. Medication dosing calculation unit 1906 may take into account one or more interstitial glucose level readings. For example, medication dosing calculation unit 1906 may take into account the most recent reading. Medication dosing calculation unit 1906 may calculate certain parameters that are indicative of changes in interstitial glucose level readings. For example, medication dosing calculation unit 1906 may calculate the minimum, mean, maximum, standard deviation, slope or higher order derivative of interstitial glucose level readings over one or more time windows. A time window may span a period of time preceding the transition to the meal-in-progress state, span a period of time that includes the transition to the meal-in-progress state, or span a period of time some time after the transition to the meal-in-progress state. Other or additional measurement sensor units such as heart rate, blood pressure, body temperature, hydration level, fatigue level are also possible. An insulin delivery system may also take into account a user's current location.

Medication dosing calculation unit 1906 may also take into account other inputs such as information related to a user's current or recent physical activity, sleep, stress etc. Medication dosing calculation unit 1906 may also take into account personal information such as gender, age, height, weight, etc.

Medication dosing calculation unit 1906 may also take into account information related to a user's medication dosing needs, such as for example a user's insulin basal rates, a user's insulin-to-carb ratios, and a user's insulin correction factor. This information may be entered or configured by the user, by a caregiver or by a health record or healthcare maintenance system. It is also possible that this information is computed automatically based on historical insulin, carbohydrates intake, blood glucose levels, etc., collected from the patient or from devices worn by the patient. Information related to a user's medication dosing needs may also be derived from historical data collected and stored by the medication dispensing system. For example, the dosage of medication (e.g. insulin) delivered by the medication dispensing unit in a period of time preceding the current food intake event. Medication dosing calculation unit 1906 may take into account medication dosages delivered in connection with one or more prior food intake events that occurred in the past at or around (e.g., within a specified time window) the same time of day, and/or the same day of the week.

Medication dosing calculation unit 1906 may also take into account the medication still active from previous medication dispensing events, such as for example the insulin-on-board.

Medication dosing calculation unit 1906 may also include parameters related to food intake events that occurred in the past at or around (e.g. within a specified time window) the same time of day, and/or the same day of the week, and/or at the same location. Medication dosing calculation unit 1906 may for example look at the duration of past food intake events, the estimated amounts consumed during past food intake events, the average pace of eating during past food intake events, the eating methods of past food intake events, the type of utensils or containers used during past food intake events, or the amounts of carbohydrates consumed during past food intake events. Other parameters are also possible. Some of these additional parameters (e.g., duration or pace) may be computed by the food intake tracking and feedback system without requiring any user intervention. In other cases, a user intervention, input or confirmation by the user may be necessary.

Medication Dispensing Schedule

Medication dosing calculation unit 1906 may instruct medication dispensing unit to administer the initial medication dosage all at once, or may specify a delivery schedule for administering the medication. In one embodiment of the current disclosure, medication dosing calculation unit 1906 computes the medication dosage as well as a schedule for the delivery of the medication. As an example, medication dosing calculation unit 1906 may determine that 5 units of insulin need to be delivered and may specify a delivery schedule as follows: 2 units to be administered immediately, 1 unit after 2 minutes, 1 unit after 5 minutes and 1 unit after 7 minutes. This is just one example and other time profile structures are of course possible.

Medication dosing calculation unit 1906 may communicate both the medication dosage and schedule to medication dispensing unit 1908. Alternatively, medication dosing calculation unit 1906 may manage the schedule and send one or more messages to medication dispensing unit 1908 every time medication needs to be administered along with the dosage of medication to be administered.

In a preferred embodiment of the current disclosure, medication dosing calculation unit 1906 may upon entering the meal-in-progress state or some time thereafter instruct medication dispensing unit 1908 to initiate delivery of medication, via the messages 1907. It may for example instruct medication dispensing unit 1908 to deliver one or more small micro-doses of medication.

Additional Dosages and Dosage Adjustments

During the food intake event and/or some time after the food intake event, medication dosing calculation unit 1906 may periodically (e.g., every couple of minutes) or continuously monitor in part one or more inputs 1905 from measurement sensor processing unit(s) 1909, and/or one or more inputs 1903 from dietary tracking and feedback system 1902 to determine if and how much additional medication should be administered or whether a scheduled medication dispensing should be adjusted. Other inputs such as inputs described in earlier sections of this disclosure may also be taken into account.

When computing a medication dosage or medication dosage adjustment, medication dosing calculation unit 1906 may take into account whether or not a food intake event is in progress. If a food intake event is not or no longer in progress, medication dosing calculation unit 1906 may for example take into account the time since the end of the last food intake event. If a food intake event is in progress, medication dosing calculation unit 1906 may for example take into account the time elapsed since the start of the current food intake event, the average or median pace of eating since the start of the current food intake event, the estimated total amounts consumed since the start of the current food intake event. Other examples are also possible.

In a specific embodiment of the current invention, medication dosing calculation unit 1906 may compute and/or adjust, in real time or near real time the dosage to be delivered by medication dispensing unit 1908 at a specific time based on at least one or more of the following: the actual or probable occurrence of a bite gesture, the actual or probable occurrence of a minimum number of bites, sips or mouthfuls within a specified window relative to the specific time of medication dosing, the pace of food intake within a time window relative to the specific time of medication dosing and/or relative to the start of the food intake event exceeding a pre-configured threshold, the amounts consumed since the start of the food intake event or in a specified window relative to the specific time of medication dosing exceeding a pre-configured threshold, the duration of the food intake event exceeding a pre-configured threshold.

As an example, the medication dosing calculation unit 1906 may compute an initial medication dosage to be administered by medication dispensing unit 1908 when the start of food intake is detected. It may alternatively or additionally determine a dose or micro-dose of medication to be delivered each time a bite gesture is detected. Medication dosing calculation unit 1906 may communicate such dosing information to medication dispensing unit 1908. The dose or micro-dose to be delivered per bite gesture (e.g. the "insulin-to-bites" ratio) may vary by user and may further vary based on meal type, time of day, day of week, location, other detected lifestyle events etc. Medication dosing calculation unit 1906 may take into account a patient's historical food intake data, historical insulin needs and historical glucose levels when determining the micro-dose to be delivered per bite gesture. Other examples are also possible.

Medication dosing calculation unit 1906 may adjust a dosing and communicate such adjustment to medication dispensing unit 1908 based on the observed absence of one or more characteristics or actions in the current behavior event. For example, medication dosing calculation unit 1906 may adjust a dose downwards if a food intake event ends prior to the assumed, anticipated or predicted end time, if the number of bites and/or amounts consumed are less than the assumed, anticipated or predicted amounts consumed, if the pace of eating is slower than the assumed, anticipated or predicted pace of eating. Other examples are also possible.

Medication dosing calculation unit 1906 may also take into account one or more recent inputs from measurement sensor processing unit 1909. For example, in case medication dosing calculation unit 1906 is an insulin dosing unit in an automated insulin delivery system (aka artificial pancreas) and measurement sensor unit 1904 is a CGM, medication dosing calculation unit 1906 may take into account the value of the most recent interstitial glucose level reading and/or the change in interstitial glucose level readings over a time window immediately or closely preceding the current time. If the most recent interstitial glucose level reading is below a specified threshold and/or a change in interstitial glucose level readings is exceeding a specified negative threshold, medication dosing calculation unit 1906 may determine to adjust the insulin dosage down, or suspend insulin delivery until the interstitial glucose level readings reaches a second specified threshold and/or the change in interstitial glucose level readings is no longer exceeding a second specified negative threshold, has turned positive or is exceeding a specified positive threshold.

In some embodiments of the current disclosure, upon detecting of a concerning measurement sensor processing unit output, medication dosing calculation unit 1906 may send an alert to the user, one or more of his caregivers, a healthcare provider, a monitoring system or to an emergency response system, or to a third party who may have a direct or indirect interest in being informed about the occurrence of such episodes.

Likewise, if the most recent interstitial glucose level reading exceeds a specific threshold and/or a change in interstitial glucose level readings is exceeding a specified positive threshold, medication dosing calculation unit 1906 may determine that an additional medication dosage should be administered, that an already scheduled medication dosage needs to be adjusted to a larger dosage or delivered at a time earlier than the currently scheduled time. Medication dosing calculation unit 1906 may optionally take into account additional inputs from dietary tracking and feedback system 1902 to compute the additional medication dosage or medication dosage adjustment. Medication dosing calculation unit 1906 may send one or more messages 1907 to medication dispensing unit 1908 to inform medication dispensing unit 1908 of the additional or adjusted medication dispensing requirements.

Upon detection of an actual or imminent end of a food intake event, or some time thereafter, dietary tracking and feedback system 1902 may send a signal 1903 to medication dosing calculation unit 1906 to inform medication dosing calculation unit 1906 that an actual or imminent end of a food intake event has been detected. Medication dosing calculation unit 1906 may use this information to change its state to a "no-meal-in-progress" state. In specific embodiments, the medication dosing calculation unit, when in a no-meal-in-progress state may periodically or continuously monitor in part one or more inputs 1905 from measurement sensor processing unit(s) 1909, and/or one or more inputs 1903 from dietary tracking and feedback system 1902 to determine if and how much additional medication should be administered or whether a scheduled medication dispensing should be adjusted. Other inputs such as inputs described in earlier sections of this disclosure may also be taken into account. When in the no-meal-in-progress state, the frequency of monitoring and/or updating/adjusting medication dosing may be different from the frequency of monitoring and/or updating/adjusting medication dosing when in the "meal-in-progress" state. The algorithms used to determine a medication dosage or medication dosage adjustment may also be different between the "meal-in-progress" state and the "no-meal-in-progress" state.

Description of Medication Dosing Learning System

In some embodiments of the current disclosure, medication dosing calculation unit 1906 may collect, and store data and information about food intake events. In some embodiments, medication dosing calculation unit 1906 may perform additional processing steps on collected data and information before storing. Processing steps may be filtering, averaging, applying arithmetical operations, and applying statistical operations. Other processing steps are also possible.

Data and information about food intake events might be stored as data elements in a database that maintains data records about food intake events.

Data elements may be event data elements and contain information or parameters that characterize the food intake event. Such information may include, but is not limited to, the event start time, the day of week the event occurred, the date of the event, the duration of the event, the event end time, metrics associated with the speed or pace at which subject is eating or drinking, metrics associated with the amounts of food or liquid consumed during the event.

Data elements may also be measurement data elements and contain information or parameters that characterize one or more signals measured by one or more measurement sensor units 1904 and processed by one or more measurement sensor processing units 1909. Such information may include, but is not limited to, sensor reading levels corresponding to specific times in connection with the food intake event, or the average, minimum, or maximum sensor reading levels corresponding to specific time windows in connection with the food intake event. Specific times might for example be the start of the food intake event, periodic or pre-defined points in time during the food intake event, the end of the food intake event, or periodic or pre-defined times after the food intake event. Other times are also possible. Specific time windows might for example be a duration of time immediately preceding the start of the food intake event, a duration of time prior to the start of the food intake event, the duration of the food intake event, a specific duration of time within the food intake event, a duration of time immediately following the end of a food intake event or a duration of time some time after the end of a food intake event.

In one specific embodiment the medication dosing calculation unit is an automated insulin delivery system, and the sensor reading levels are interstitial glucose reading levels obtained from a continuous glucose monitoring sensor.

Data elements may also be dosage data elements and contain information or parameters that characterize the medication dosage and delivery schedule in connection with the food intake event.

Other data elements are also possible. One or more event data elements, one or more measurement data elements and/or one or more dosage data elements of the same food intake event may be recorded as a single record entry in a database. Event data elements, measurement data elements and/or dosage data elements may also be recorded as separate records in a database. Other data structures consistent with the teachings herein might also be used, or used instead.

Medication dosing calculation unit 1906 may include a processing and analysis subsystem.

The processing and analysis subsystem may use statistics, machine learning or artificial intelligence techniques on entries in the database to build a model that recommends an adequate medication dosage and/or delivery schedule. The processing and analysis subsystem may be used to recommend an initial medication dosage, and/or to recommend additional medication dosage(s) or dosage adjustment(s).

Figure 20:
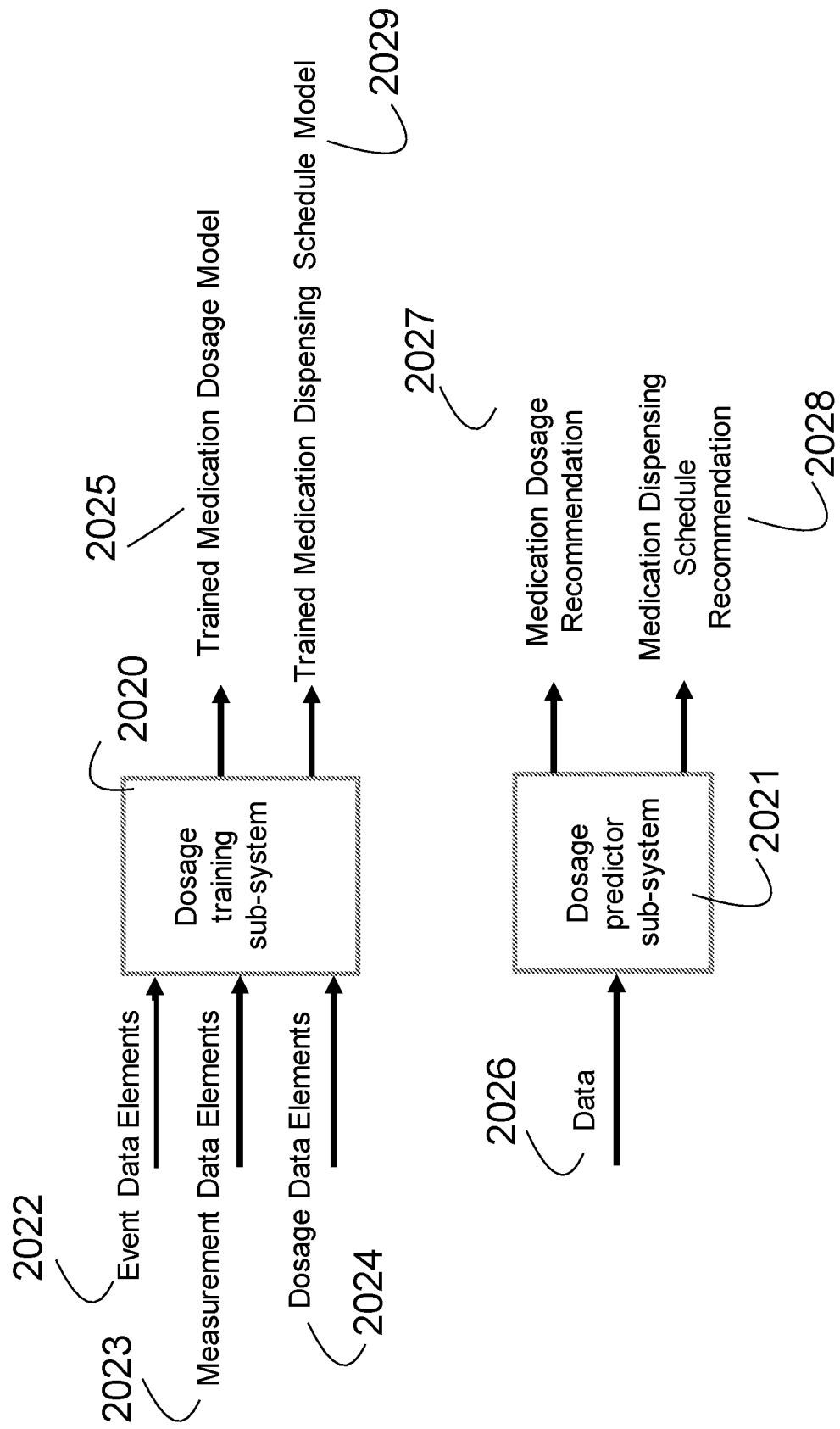
FIG. 20 is an illustrative example of a machine learning system that might be used with other elements described in this disclosure.

FIG. 20 is an illustrative example of a machine learning system that might be used with other elements described in this disclosure. The machine learning system of FIG. 20 includes a dosage training subsystem 2020 and a dosage predictor subsystem 2021. In some embodiments of the present disclosure, the machine learning system may include additional subsystems or modified versions of the subsystems shown in FIG. 2. Dosage training subsystem 2020 might use event data elements 2022, measurement data elements 2023 and dosage data elements 2024 as inputs. The dosage training sub-system applies machine learning techniques to build a model that recommends an adequate medication dosage and/or a medication dispensing schedule. It might use supervised learning techniques on one or more entries from the database to train the model. Event data element(s) 2022 and/or measurement data element(s) 2023 might be used as features for the model. One or more dosage data elements 2024 might be used as labels. Trained model(s) 2025 and/or 2029 is then used in dosage predictor subsystem 2021 to generate a medication dosage recommendation and/or medication dispensing recommendation corresponding to a new unlabeled data input 2026.

Medication dosing calculation unit 1906 may include a processing unit and perform additional processing on the data elements and analyze the data to extract information about the user's eating and drinking activities and behaviors, sensor measurements (e.g., glycemic control) and/or medication regimen. Processing may include but is not limited to filtering, extracting specific data elements, modifying data or data elements, combining data or data elements. Analysis may also include comparing specific data elements to data that is stored in a look up table or database, correlating data elements to data elements that were obtained at an earlier time and/or from different subjects. Medication dosing calculation unit 1906 may store raw or processed data in one or more data storage unit(s). Storage may be temporary or permanent.

In some variations, records in the database may be subdivided into groups (e.g., based on meal type—breakfast, lunch, dinner, snack) and a different model may be used for each subgroup. Alternatively, the same model may be used but it may be trained using data from only one or a selective set of subgroups. In other variations, instead of a supervised machine learning approach (i.e., where features are specified manually), unsupervised learning may be used instead. With unsupervised learning, the classifier will autonomously generate features from the raw dataset provided.

Medication dosing calculation unit 1906 may collect, and store data and information about other user activities. For example, medication dosing calculation unit 1906 may collect information or data about a user's physical activity, sleep activity, sexual activity. Medication dosing calculation unit 1906 may also collect and store information about a user's stress, heart rate, blood pressure etc. In some embodiments, medication dosing calculation unit 1906 may perform additional processing steps on collected data and information before storing. Processing steps may be filtering, averaging, applying arithmetical operations, and applying statistical operations. Other processing steps are also possible. Medication dosing calculation unit 1906 may link this data and information to one or more food intake events. Data and information about food intake events might be stored as data elements in a database that maintains data records about food intake events. These data elements may also be used as inputs to processing and analysis subsystem of medication dosing calculation unit 1906. For example, these data elements may be used as additional or alternative event data inputs to a dosage training subsystem. These data elements may for example be features for the model.

Medication dosing calculation unit 1906 may also collect inputs such as information related to a user's physical activity, sleep, stress etc. Medication dosing calculation unit 1906 may for example compare a user's current or recent physical activity to past physical activity and use the output of that comparison into the calculation of a medication dosage.

While not illustrated in detail in FIG. 20, the machine learning system, dosage training subsystem 2020, and dosage predictor subsystem 2021 can be implemented using various structural elements. For example, dosage prediction might be implemented using computer hardware, such as a processor, program code memory and program code stored in the program code memory. This might be a separate embedded unit, or might be implemented on a processor with memory that is used for other functions and tasks as well as dosage prediction. This processor and memory might be built into a wearable device, a mobile device that communicates with a wearable device, a server that is in communication, directly or indirectly, with a wearable device or sensors, or some combination of the above. Other elements might similarly be implemented, such as storage for event data elements 2022, storage for measurement data elements 2023 and storage for dosage data elements 2024, program code that implements the machine learning techniques to build a model that recommends an adequate medication dosage and/or a medication dispensing schedule, storage for the model, storage for a database to train the model, and hardware circuitry needed to communicate messages, such as sending a medication dosage recommendation message, a medication dispensing recommendation message, or a signal to a hardware device that dispenses medication.

In certain embodiments, the medication dispensing system of FIG. 19 may operate without any manual intervention or at least not requiring any manual intervention. In other embodiments, the medication dispensing system of FIG. 19 may require some manual intervention. In one example, medication dosing calculation unit 1906 may calculate a medication dosage and/or medication delivery schedule but, instead of instructing the medication dispensing unit 1908 to initiate or schedule delivery of medication, it may send a message to the patient, one or more caregivers of the patient, a healthcare professional, a monitoring system, etc. to confirm the proposed medication dosage and/or medication delivery schedule. The message can be a text message, a push notification, a voice message, etc., but other message formats are also possible.

In some embodiments, the patient, caregiver, etc. may have an option to alter the proposed medication dosage and/or medication delivery schedule. Upon receiving a confirmation from the patient, caregiver, etc., medication dosing calculation unit 1906 may send one or more instructions to the medication dispensing unit 1908 to initiate or schedule delivery of medication. The instruction(s) may also be sent by a device or unit other than the medication dosing calculation unit 1906. As an example, the instruction(s) may be sent to the medication dispensing unit 1908 directly from the device on which the patient, caregiver etc. received the message to confirm the medication dosage and/or medication delivery schedule. Other user interventions are also possible, such as allowing for a "snooze" function to move a message to a predetermined time in the future.

Figure 21:
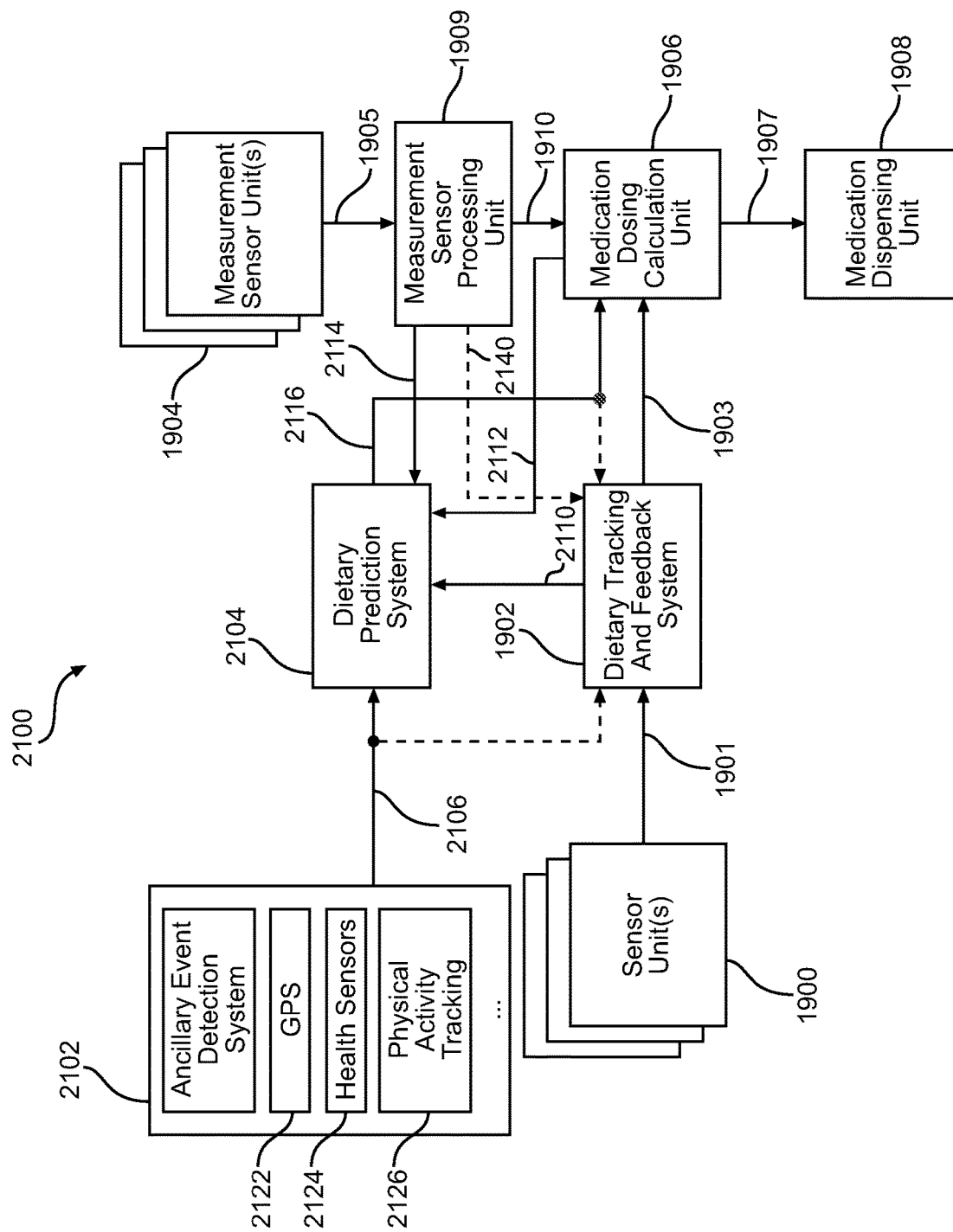
FIG. 21 is a schematic functional diagram of an exemplary embodiment of a medication dispensing system.

FIG. 21 is a schematic functional diagram of an exemplary embodiment of an automated medication dosing and dispensing system 2100 that employs behavior prediction. The illustrated system 2100 includes various blocks that represent functional modules, devices or hardware elements, and/or processing logic. Moreover, the depicted embodiment of the system 2100 includes functional modules and related processing logic that are similar to those described above with reference to the exemplary system shown in FIG. 19. Accordingly, common reference numbers are used in FIG. 19 and FIG. 21 to indicate similar, identical, or equivalent blocks or signals. In this regard, the system 2100 includes or cooperates with sensors or sensor units 1900 that are designed, configured, and operated to detect physical movement of the user (more particularly, to detect movements of specific body parts of the user, such as a wrist, a forearm, a hand). The system 2100 also includes a physical behavior detection system (implemented as a dietary tracking and feedback system 1902), measurement sensor units 1904, a medication dosing calculation unit 1906, a medication dispensing unit 1908, and a measurement sensor processing unit 1909 as described above with reference to FIG. 19. Sensor data 1901 from the sensor units 1900 is processed by the dietary tracking and feedback system, which generates output (represented by the signal 1903) that serves as an input to the medication dosing calculation unit 1906. The medication dosing calculation unit 1906 generates output (e.g., messages 1907) that is provided to control certain functions of the medication dispensing unit 1908. The measurement sensor units 1904 generate sensor output (reference number 1905) that is provided to the measurement sensor processing unit 1909. Output 1910 from the measurement sensor processing unit 1909 is provided to the medication dosing calculation unit 1906, which calculates dosages based on that output 1910 and other factors. In this regard, the measurement sensor unit(s) 1904 or the measurement sensor processing unit 1909 may serve as a source of data that can be used to support various features, operations, and functions of the system 2100.

The illustrated embodiment of the system 2100 also includes or cooperates with the following components, without limitation: an ancillary event detection system 2102; and a dietary prediction system 2104. The ancillary event detection system 2102 serves as a source of data that generates output used as ancillary inputs 2106 to the dietary prediction system 2104. In certain embodiments, at least some of the information generated by the ancillary event detection system 2102 is used to support additional functions, features, or operations of the system, as described in further detail below. For this particular implementation, the dietary prediction system 2104 also cooperates with the dietary tracking and feedback system 1902, the medication dosing calculation unit 1906, and the measurement sensor processing unit 1909. More specifically, the dietary prediction system 2104 may obtain: food intake event information 2110 from the dietary tracking and feedback system 1902;

dosing information 2112 from the medication dosing calculation unit 1906; and/or sensor measurement information 2114 from the measurement sensor processing unit 1909, as depicted in FIG. 21. Although not represented by a distinct arrow in FIG. 21, output from the sensor units 1900 may also be provided to the dietary prediction system 2104. The dietary prediction system 2104 generates predictive information 2116 as an output, which is provided to at least the medication dosing calculation unit 1906. In this regard, the dietary prediction system 2104 may serve as a source of data that can be used to support various features, operations, and functions of the system 2100. Thus, the ancillary event detection system 2102 and the dietary prediction system 2104 enhance the operation of the "baseline" medication dispensing system described above and shown in FIG. 19.

The ancillary event detection system 2102 is configured to detect occurrences of events that can be used to predict whether or not the user will consume something in the future. Alternatively or additionally, the ancillary event detection system 2102 is configured to generate information or data that can be processed (e.g., by the dietary prediction system) to predict whether or not the user will consume something in the future. In contrast, the dietary tracking and feedback system 1902 is designed to detect physical behavior events that "directly" correspond to an eating or drinking event, such as chewing, sipping, biting, movement corresponding to eating with a spoon, fork, or knife, etc. This description uses "ancillary" as a label for detectable physical behavior events that are not explicitly and directly associated with eating or drinking per se (e.g., location data, orientation data, data related to physical and other activities, heart rate data, blood glucose levels and other biometric data, data related to stress levels, and speech input).

The ancillary event detection system 2102 may include any number of devices, sensors, processing logic, functional modules, subsystems, detectors, and/or hardware components as appropriate for the particular embodiment. Although depicted separately in FIG. 21, the ancillary event detection system 2102 may include or leverage one or more of the sensor units 1900 that support the dietary tracking and feedback system 1902. The illustrated embodiment of the ancillary event detection system 2102 includes or cooperates with at least the following components, without limitation: a GPS system and/or GPS sensors 2122; a health monitor with associated sensors 2124, e.g., a device that measures blood oxygen, blood pressure, body temperature, heart rate, and/or other characteristics; and a physical activity tracking device 2126, e.g., a wearable or carried device that generates data related to user fitness (number of steps taken, amount and quality of sleep time, distance travelled during walking, running, or cycling, etc.). An embodiment of the ancillary event detection system 2102 may include or cooperate with additional or alternative devices and components, as appropriate for the particular implementation of the system 2100.

Gesture recognition methods, physical behavior event detection methods, medication dispensing systems, and other methods and apparatus described elsewhere herein can be applied to various components of the system 2100 depicted in FIG. 21. The following description focuses on the dietary prediction system 2104, the dietary tracking and feedback system 1902, and the medication dosing calculation unit 1906, along with various interactions between those components.

The dietary tracking and feedback system 1902 detects the actual start or probable start of a food intake event, and provides associated output 1903 to the medication dosing calculation unit 1906. The output 1903 may include an indication of the detected food intake event, optionally with additional characteristics of the food intake event. The dietary tracking and feedback system 1902 may send this information to the medication dosing calculation unit 1906 when it occurs, becomes available, or at some time after it occurs or becomes available. Alternatively, the medication dosing calculation unit 1906 may periodically query the dietary tracking and feedback system 1902 for such information. In some embodiments, the dietary tracking and feedback system 1902 may determine a probability (e.g., a score, a grade, or any measured value) that a food intake event is occurring and signal the determined probability to the medication dosing calculation unit 1906.

The dietary tracking and feedback system 1902 may also send food intake event information 2110 about current or past food intake events to the dietary prediction system 2104. Alternatively, or additionally, the dietary prediction system 2104 may periodically query the dietary tracking and feedback system 1902 for current or past food intake events detected by the dietary tracking and feedback system 1902. The food intake event information 2110 may include, for example, the date, start time, end time, duration, and/or the average or median pace of a food intake event. The food intake event information 2110 may include parameters such as the detected eating or drinking method, the detected utensils or container used, the meal type, or parameters that are indicative of amounts or content of foods/liquids consumed. Other characteristics or parameters of a detected food intake event may also be sent to the dietary prediction system 2104.

The dietary prediction system 2104 may store and process the food intake event information 2110 received from the dietary tracking and feedback system 1902, optionally in combination with the ancillary inputs 2106 obtained from the ancillary event detection system 2102, to determine a likelihood of the occurrence of a food intake event or start of a food intake event at a given date and time (or within a given time window) in the future. Accordingly, the dietary prediction system 2104 considers physical behavior events that were detected in the past, for purposes of anticipating or predicting the occurrence of similar or correlated physical behavior events that have yet to occur. The predictive information 2116 generated by the dietary prediction system 2104 may indicate the probability that a meal will start soon, or a set of probabilities that a meal will occur within a set of specified time windows. As an example, the dietary prediction system 2104 may output a probability or confidence level that a food intake event will start in the next 15 minutes. In accordance with certain embodiments, the dietary prediction system outputs such a probability or confidence level when there is no meal currently in progress. Each prediction, or the overall set of predictions, may be accompanied by further information such as the predicted contents of the meal, the predicted amount of calories to be consumed, the predicted pace of eating, the predicted number of bites, the predicted duration of the meal, the predicted eating method(s) or utensil(s) used, or other information. Each of these predictions may or may not be in the form of a probability distribution over the set of possible values.

As an example, the dietary prediction system 2104 may predict that a food intake event is expected to start within the next ten minutes, and that the confidence level of this prediction is 83%. The dietary prediction system 2104 may further provide eating method confidence levels, such as: 12% eating with fork, 75% eating with fingers, 7% eating with spoon, 6% eating with chopsticks. The dietary prediction system 2104 may further output a prediction for the meal duration, such as: 90% probability the meal will last more than three minutes, 50% probability the meal will last more than seven minutes, 10% probability the meal will last more than 13.7 minutes. Different outputs and output formats are also possible. Furthermore, the predictions that are outputted by the dietary prediction system 2104 may be updated periodically or as more information about the imminent food intake event, or other relevant ancillary information, becomes available.

The dietary prediction system 2104 may, for example, process historical food intake event data from a user to determine the percentage of time that the user started a food intake event at a given time of day or within a given time window in the past. That percentage measurement can then be used to determine the likelihood that a start of a food intake event will occur for that user at a given time or within a given time window in the future. For example, if the dietary tracking and feedback system 1902 provides a user's historical food intake data over a 35 day period, and in 30 of the 35 days, a start of a food intake event was detected or occurred in a time window between 6:00 PM and 6:15 PM, the dietary prediction system 2104 could then determine and signal that there is an 85.7% probability that the same user will start a food intake event between 6:00 PM and 6:15 PM on a day in the future. This data could be used in a real-time predictive implementation, where the dietary prediction system 2104 provides to the medication dosing calculation unit 1906 the probability of a food intake event starting in the next 15 minutes. Other time intervals are also possible. The dietary prediction system 2104 could provide this information periodically to the medication dosing calculation unit 1906, when triggered by an external signal, or when queried by the medication dosing calculation unit 1906.

The dietary prediction system 2104 can improve the accuracy of its predictions by taking into account additional information such as calendar information (e.g., the day of the week, the season, or the month). In the above example, there were five days where no food intake event was recorded between 6:00 PM and 6:15 PM. If those five days were all Sundays, the dietary prediction system 2104 could then determine that there is a close to 100% probability that a user will start a food intake event between 6:00 PM and 6:15 PM on Mondays through Saturdays, and a close to 0% probability for the same time window on Sundays.

The dietary prediction system 2104 may also improve the accuracy of its predictions by taking into account any of the ancillary inputs 2106. Examples of ancillary inputs 2106 include, without limitation: location data, orientation data, data related to physical and other activities (e.g., walking, running, biking, swimming, sleeping, driving, cooking), heart rate data, blood glucose levels and other biometric data, data related to stress levels, and speech input. Ancillary inputs 2106 may also include further contextual information such as which people, devices, and noises are nearby. Ancillary inputs 2106 may be associated with a particular time or time window preceding a food intake event, a time or time window related to the start, probable start, or imminent start of a food intake event, a time or time window related to taking place of a food intake event or a time or time window following a food intake event. Ancillary inputs 2106 may have a temporal relationship with the food intake event, and the parameter of interest for the prediction may be the relative time that elapses between the detection of one or more ancillary inputs 2106 or a change in one or more ancillary inputs 2106 and the time of the start of a food intake event. For example, an ancillary input 2106 may be location and the feature of interest may be the relative time that elapses between the arrival time at that location and the start of a food intake event. In another example, the ancillary input 2106 may be a physical activity, and the feature of interest may be the relative time that elapses between the end of the physical activity and the start of a food intake event. Other examples are also possible.

The following is an example where the dietary prediction system 2104 records location information as one of the ancillary inputs 2106. This example assumes that the dietary tracking and feedback system 1902 provides a user's historical food intake data over a 35-day period. In 30 of the 35 days, there was a food intake event that began in a time window between 6:00 PM and 6:15 PM. This example also assumes that for the 30 days where there was a food intake occurrence recorded between 6:00 PM and 6:15 PM, the user was at home at 6:00 PM, and for the five days where there was no start of a food intake occurrence recorded between 6:00 PM and 6:15 PM, the user was at work at 6:00 PM. Using this information, the dietary prediction system 2104 indicates at 6:00 PM that a food intake event is likely to begin in the next 15 minutes, based on the location information provided by the ancillary inputs 2106. If the user is home at 6:00 PM, the dietary prediction system 2104 may determine that there is a close to 100% probability that there will be a start of a food intake event for this user in the next 15 minutes. If the user is at work at 6:00 PM, the dietary prediction system may determine there is a close to 0% probability that there will be a start of a food intake event for this user in the next 15 minutes.

The dietary prediction system 2104 may further process the percentage of historical occurrences before sending it to the medication dosing calculation unit 1906. For example, the dietary prediction system 2104 may clip, scale, smoothen, or quantize the probability data. The dietary prediction system 2104 may, for example, use a scale from 1 to 10 to rate the probability and communicate the output of the rating to the medication dosing calculation unit 1906. The dietary prediction system 2104 may also compute a metric representative of the amount of historical data available to signal a confidence level of the prediction. For example, if the prediction is based on 100 historical data points, the confidence level of the prediction would be lower compared to a scenario where the prediction is based on 10,000 historical data points.

In another example, the dietary prediction system 2104 may use data from the dietary tracking and feedback system 1902 in combination with the ancillary inputs 2106 that provide location information to compute the probability that a start of a food intake event will occur at a certain time or within a certain time window after a user left or arrived at a specific location, based on the historical probability/likelihood. For example, the dietary prediction system 2104 can compute the probability that the start of a food intake event will occur in a time window 15 to 30 minutes or 30 to 45 minutes after the user arrives home.

In another example, the dietary prediction system 2104 may use data from the dietary tracking and feedback system 1902 in combination with ancillary inputs 2106 that provide location information to adjust/improve the calculated probability that food intake took place at a certain time or within a certain time window before a user left or arrived at a specific location, based on the historical probability/likelihood. For example, the dietary prediction system 2104 can compute the probability that the food intake occurred in a time window 15 to 30 minutes or 30 to 45 minutes before the user leaves the house.

The dietary prediction system 2104 may improve the accuracy of its predictions by taking into account ancillary inputs 2106 associated with events that are not food intake events per se, but that may have a temporal relationship to the start or occurrence of a food intake event. In certain embodiments, such events are at least in part detected using gesture recognition technology based on motion sensor information from one or more wearable devices. Examples of such detectable events include, without limitation: a user filling a bowl with cereal; the user opening a refrigerator or a freezer, a cutting motion, a user placing a napkin on their lap, opening a can or other type of container, starting a microwave oven, opening a wrapper, a scooping motion, pouring a beverage, sitting down, moving a chair to table, and setting a table with dishes or utensils. In this regard, the dietary prediction system 2104 may interface to the ancillary event detection system 2102 (which uses motion sensor information from one or more wearable devices) to determine that someone is setting the table. Accordingly, "setting the table" ancillary event information is sent to the dietary prediction system 2104 as an ancillary input 2106. The dietary prediction system 2104 may use the data from the dietary tracking and feedback system 1902 in combination with the ancillary inputs 2106 to compute the percentage of time that a start of a food intake event occurred within a specified time window following an ancillary event detection, and use that information to predict the probability that the start of a food intake event will occur in a specific time window in the future.

As another example, the dietary prediction system 2104 may use data from the dietary tracking and feedback system 1902 in combination with ancillary inputs 2106 that provide ancillary event information to compute the probability distribution of the contents of a meal currently in progress, based on the historical probability/likelihood given the user's recent activities. For example, the dietary prediction system 2104 can compute the probability that the user is eating an energy bar (after determining, detecting, or predicting that the user has just finished a workout).

The dietary prediction system 2104 may process data received from the dietary tracking and feedback system 1902, optionally in combination with ancillary inputs 2106 to predict other characteristics of a current or future food intake event. Examples of such predicted characteristics include, without limitation: the predicted duration of the food intake event, or metrics indicative of amounts likely to be consumed during the food intake event. To this end, the dietary prediction system 2104 may process historical food intake event data from a user to determine the percentage of time that a user started a food intake event at a given time of day or within a given time window in the past, along with statistical information about those food intake events to determine the probability and characteristics of a future food intake event at the same time or within the same time window. For example, the dietary prediction system 2104 may determine that a food intake event starting or occurring between 6:00 PM and 6:15 PM has a mean duration of 12 minutes. The dietary prediction system 2104 may also analyze the historical data to compute median duration, minimum duration, maximum duration, standard deviation, and/or duration corresponding to X % probability. Other statistical metrics are also possible. The dietary prediction system 2104 may send one or more of those parameters to the medication dosing calculation unit 1906 for consideration. Similar statistical characteristics may be computed to predict the pace of eating, the amounts consumed, etc.

Figure 22:
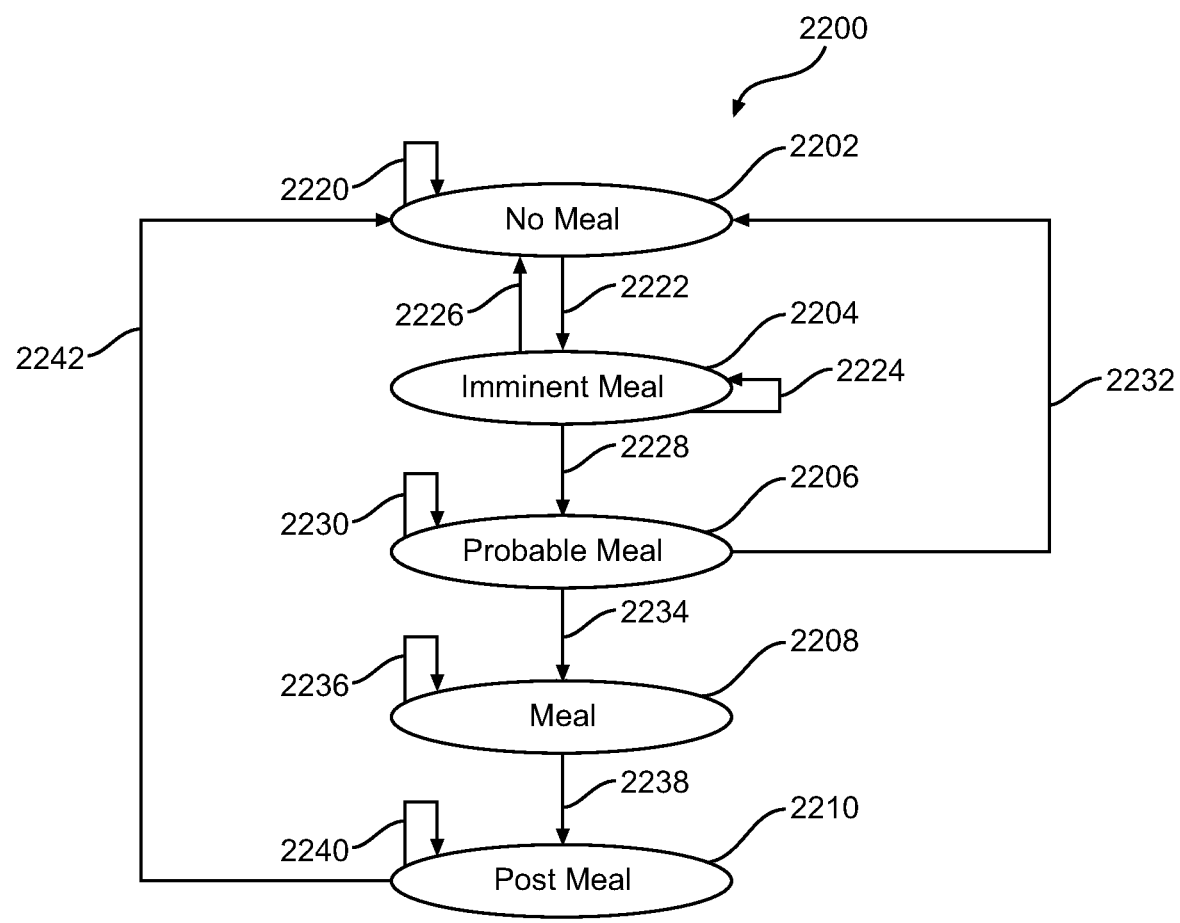
FIG. 22 is a state diagram that applies to an exemplary embodiment of a medication dosing calculation unit utilized by a medication dispensing system.

FIG. 22 is a state diagram 2200 that applies to an exemplary embodiment of the medication dosing calculation unit 1906. For this particular implementation, the states depicted in FIG. 22 are based on inputs received from the dietary tracking and feedback system 1902 and the dietary prediction system 2104. Thus, the medication dosing calculation unit 1906 may adjust its medication dosing and medication delivery schedule based on its present meal state. The state diagram 2200 of FIG. 22 contemplates the following meal states: No Meal 2202; Imminent Meal 2204; Probable Meal 2206; Meal 2208; and Post Meal 2210. Additional and/or alternative meal states can be defined and supported, as appropriate for the particular implementation of the medication dosing calculation unit 1906. In FIG. 22, an arrow leading from one state to another state represents a change in the current meal state, and an arrow leading from a state back to itself indicates that the current meal state does not change.

In accordance with certain embodiments, the medication dosing calculation unit 1906 is implemented as (or with) an automated closed loop insulin delivery system. When the dietary prediction system 2104 predicts the start or occurrence (or the probable start or occurrence) of a food intake event at a certain time or within a certain time window in the future, the medication dosing calculation unit 1906 may change its state from the No Meal state 2202 to the Imminent Meal state 2204. Upon transitioning from the No Meal state 2202 to the Imminent Meal state 2204, or some time thereafter, the medication dosing calculation unit 1906 may increase the basal insulin dosing or lower the blood glucose target. The medication dosing calculation unit 1906 may take into account the current and/or past glucose level reading information received from the measurement sensor processing unit 1909 when deciding if and by how much to increase the basal insulin dosing and/or to what target to set the blood glucose target. The medication dosing calculation unit 1906 may also determine to administer one or more doses or micro-doses of insulin on a preconfigured or adjustable delivery schedule. The insulin dosing and delivery schedule may take into account additional characteristics about the anticipated future food intake event that it receives from the dietary prediction system 2104 (e.g., predictive information about meal duration or estimated amounts). The medication dosing calculation unit 1906 may also take into account other parameters as described elsewhere herein when determining an insulin dosing and delivery schedule while in the Imminent Meal state 2204.

Based on one or more inputs received from the dietary tracking and feedback system 1902, the medication dosing calculation unit 1906 may transition from the Imminent Meal state 2204 to the Probable Meal state 2206, from the Probable Meal state 2206 to the Meal state 2208, or from the Meal state 2208 to the Post Meal state 2210. During each state transition or some time thereafter, the medication dosing calculation unit 1906 may modify its insulin dosing and insulin delivery schedule in an appropriate manner.

During or after a state transition, or while in a given state, the medication dosing calculation unit 1906 may adjust its dosing and/or delivery schedule based on additional characteristics provided by the dietary tracking and feedback system 1902 or the dietary prediction system 2104, or by taking into account other parameters as described elsewhere herein.

State Transition Example 1

For this example, the medication dosing calculation unit 1906 obtains the following information from the dietary tracking and feedback system 1902: Probable Meal Start, which is set to a value of "1" if the criteria to declare a detected probable start of a meal has been met, and is otherwise set to a value of "0"; Meal Start, which is set to a value of "1" if the criteria to declare a detected start of a meal has been met, and is otherwise set to a value of "0"; and Meal End, which is set to a value of "1" if the criteria to declare a detected end of a meal has been met, and is otherwise set to a value of "0". For this example, the medication dosing calculation unit 1906 obtains the following information from the dietary prediction system 2104: Meal Prediction Confidence, which is a confidence level measurement that indicates the probability that the start of a meal will occur within a specified period of time from the current time.

Referring to the state diagram 2200, if the medication dosing calculation unit 1906 is in the No Meal state 2202 and the Meal Prediction Confidence is less than a meal prediction threshold confidence value, then the No Meal state 2202 is preserved (as indicated by the loopback arrow 2220). If, however, the Meal Prediction Confidence is greater than or equal to the meal prediction threshold confidence value, the meal state changes from the No Meal state 2202 to the Imminent Meal state 2204 (as indicated by the arrow 2222).

If the medication dosing calculation unit 1906 is in the Imminent Meal state 2204, the Meal Prediction Confidence is greater than or equal to the meal prediction threshold confidence value, and Probable Meal Start is set to "0", then the Imminent Meal state 2204 is preserved (as indicated by the loopback arrow 2224). If the medication dosing calculation unit 1906 is in the Imminent Meal state 2204, the Meal Prediction Confidence is less than the meal prediction threshold confidence value, and Probable Meal Start is set to "0", then the meal state returns to the No Meal state 2202 (as indicated by the arrow 2226). If, however, Probable Meal Start is set to "1", then the meal state changes from the Imminent Meal state 2204 to the Probable Meal state 2206 (as indicated by the arrow 2228).

If the medication dosing calculation unit 1906 is in the Probable Meal state 2206, the amount of time spent in the Probable Meal state 2206 is less than or equal to a predetermined probable meal timeout period, and Meal Start is set to "0", then the Probable Meal state 2206 is preserved (as indicated by the loopback arrow 2230). If the medication dosing calculation unit 1906 is in the Probable Meal state 2206 and the amount of time spent in the Probable Meal state 2206 is greater than the probable meal timeout period, then the meal state returns to the No Meal state 2202 (as indicated by the arrow 2232). If, however, the amount of time spent in the Probable Meal state 2206 is less than or equal to the probable meal timeout period, and Meal Start is set to "1", then the meal state changes from the Probable Meal state 2206 to the Meal state 2208 (as indicated by the arrow 2234).

If the medication dosing calculation unit 1906 is in the Meal state 2208, and Meal End is set to "0", then the Meal state 2208 is preserved (as indicated by the loopback arrow 2236). If, however, Meal End is set to "1", then the meal state changes from the Meal state 2208 to the Post Meal state 2210 (as indicated by the arrow 2238).

If the medication dosing calculation unit 1906 is in the Post Meal state 2210, and the amount of time spent in the Post Meal state 2210 is less than or equal to a designated post meal timeout period, then the Post Meal state 2210 is preserved (as indicated by the loopback arrow 2240). If, however, the amount of time spent in the Post Meal state 2210 is greater than the post meal timeout period, then the meal state changes from the Post Meal state 2210 to the No Meal state 2202 (as indicated by the arrow 2242).

State Transition Example 2

For this example, the medication dosing calculation unit 1906 obtains the following information from the dietary tracking and feedback system 1902: Detected Meal Start Confidence, which is a confidence level measurement that indicates the probability that the start of a meal has occurred; and Detected Meal End Confidence, which is a confidence level measurement that indicates the probability that the end of a meal has occurred. For this example, the medication dosing calculation unit 1906 obtains the following information from the dietary prediction system 2104: Meal Prediction Confidence, as described above for the State Transition Example 1.

Referring to the state diagram 2200, if the medication dosing calculation unit 1906 is in the No Meal state 2202 and the Meal Prediction Confidence is less than the meal prediction threshold confidence value, then the No Meal state 2202 is preserved (as indicated by the loopback arrow 2220). If, however, the Meal Prediction Confidence is greater than or equal to the meal prediction threshold confidence value, the meal state changes from the No Meal state 2202 to the Imminent Meal state 2204 (as indicated by the arrow 2222).

If the medication dosing calculation unit 1906 is in the Imminent Meal state 2204, the Meal Prediction Confidence is greater than or equal to the meal prediction threshold confidence value, and the Detected Meal Start Confidence is less than or equal to a probable meal start confidence threshold value, then the Imminent Meal state 2204 is preserved (as indicated by the loopback arrow 2224). If the medication dosing calculation unit 1906 is in the Imminent Meal state 2204, the Meal Prediction Confidence is less than the meal prediction threshold confidence value, and the Detected Meal Start Confidence is less than or equal to the probable meal start confidence value, then the meal state returns to the No Meal state 2202 (as indicated by the arrow 2226). If, however, the Detected Meal Start Confidence is greater than or equal to the probable meal start confidence threshold, then the meal state changes from the Imminent Meal state 2204 to the Probable Meal state 2206 (as indicated by the arrow 2228).

If the medication dosing calculation unit 1906 is in the Probable Meal state 2206, the amount of time spent in the Probable Meal state 2206 is less than or equal to a predetermined probable meal timeout period, and the Detected Meal Start Confidence is less than a meal start confidence threshold value, then the Probable Meal state 2206 is preserved (as indicated by the loopback arrow 2230). If the medication dosing calculation unit 1906 is in the Probable Meal state 2206 and the amount of time spent in the Probable Meal state 2206 is greater than the probable meal timeout period, then the meal state returns to the No Meal state 2202 (as indicated by the arrow 2232). If, however, the amount of time spent in the Probable Meal state 2206 is less than or equal to the probable meal timeout period, and the Detected Meal Start Confidence is greater than or equal to the meal start confidence threshold value, then the meal state changes from the Probable Meal state 2206 to the Meal state 2208 (as indicated by the arrow 2234).

If the medication dosing calculation unit 1906 is in the Meal state 2208, and the Detected Meal End Confidence is less than a meal end confidence threshold value, then the Meal state 2208 is preserved (as indicated by the loopback arrow 2236). If, however, the Detected Meal End Confidence is greater than or equal to the meal end confidence threshold value, then the meal state changes from the Meal state 2208 to the Post Meal state 2210 (as indicated by the arrow 2238).

If the medication dosing calculation unit 1906 is in the Post Meal state 2210, and the amount of time spent in the Post Meal state 2210 is less than or equal to a designated post meal timeout period, then the Post Meal state 2210 is preserved (as indicated by the loopback arrow 2240). If, however, the amount of time spent in the Post Meal state 2210 is greater than the post meal timeout period, then the meal state changes from the Post Meal state 2210 to the No Meal state 2202 (as indicated by the arrow 2242).

In certain embodiments, a medication dosing and dispensing system may initiate one or more of the following when the dietary prediction system 2104 predicts the start or occurrence, or the probable start or occurrence, of a food intake event at a certain time or within a certain time window in the future: interacting with the user to provide information or a reminder; interacting with the user to prompt for user input; sending a message to a remote computer system; sending a message to another person; sending a message to the user.

In certain embodiments, one or more outputs of the dietary prediction system 2104 may be sent to the measurement sensor unit 1904 and/or the measurement sensor processing unit 1909. When the dietary prediction system 2104 predicts a future or imminent start of a food intake event, the output of the dietary prediction system 2104 may be used to initiate one or more of the following, without limitation: (1) activate additional circuitry such as, for example, activating an additional sensor or a data recording mechanism; (2) activate a higher performance mode of one or more circuit or components of the system; (3) adjust the amount of power supplied to a circuit or component of the system; (4) adjust the latency of a communication channel, such as increasing the sensor read out frequency or update rate at which sensor data is transferred from the measurement sensor unit 1904 to the measurement sensor processing unit 1909, or increasing the sensor read out frequency or update rate at which outputs of the measurement sensor processing unit 1909 are sent to the medication dosing calculation unit 1906; (5) a change in sensor sampling rate, such as an increased or decreased sampling rate of one or more sensors in the measurement sensor units 1904.

An end of a food intake event might be detected by considering whether a certain time has expired since a last bite or sip movement or when other data (metadata about the wearer, motion-detection sensor data, and/or historical data of the wearer, or a combination of those) indicates the end. Based on these factors, the system makes a determination that a food intake event is not likely and then changes the state of the electronic device to an inactive monitoring state, possibly a lower power mode. The lower power mode might be implemented by reducing the sampling rate of an accelerometer and/or gyroscope, powering down the gyroscope, reducing the update rate at which sensor data is transferred from the electronic device (such as the electronic device 218 shown in FIG. 2) to the support device (such as the mobile device 219 shown in FIG. 2), or compressing the data before transferring the data from the sensing electronic device to the support electronic device.

The medication dispensing system 2100 and its dietary tracking and feedback system 1902 were described previously (with particular reference to FIG. 19 and FIG. 21). In accordance with certain embodiments of the system 2100, one or more outputs from systems that are "external" to the physical behavior tracking components or processing logic are used to determine the confidence levels associated with detected events and/or to reduce the time required to declare that a physical behavior event (e.g., a dietary event) has been detected. In this regard, FIG. 21 includes three arrows drawn with dashed lines. These dashed arrows represent additional information that can be obtained and processed by the dietary tracking and feedback system 1902. Although other sources of external data can be received and processed by the dietary tracking and feedback system 1902, the illustrated embodiment obtains any or all of the following, without limitation: one or more of the ancillary inputs 2106 provided by the ancillary event detection system 2102; predictive information 2116 generated by the dietary prediction system 2104; and sensor data 2140 generated by the measurement sensor processing unit 1909.

In accordance with this embodiment, the dietary tracking and feedback system 1902 receives additional information from the measurement sensor processing unit 1909, the dietary prediction system 2104, and/or the ancillary event detection system 2102. As an example, the dietary tracking and feedback system 1902 may process such additional information to adjust the confidence level that a food intake event is occurring or to accelerate its decision that a food intake event is occurring or is likely occurring.

As another example, when the dietary prediction system 2104 predicts an imminent food intake event, it may send this information to the dietary tracking and feedback system 1902. Moreover, the dietary prediction system 2104 may output a probability or confidence level that a food intake event will start in the next 15 minutes. In certain scenarios, the dietary prediction system 2104 may output such a probability or confidence level when there is no meal in progress. Each prediction, or the overall set of predictions, may be accompanied by further information such as the predicted contents of the meal, the predicted amount of calories to be consumed, the predicted pace of eating, the predicted number of bites, the predicted duration of the meal, the predicted eating method(s) or utensil(s) used, or other information. Each of these predictions may or may not be in the form of a probability distribution over the set of possible values. This data can be sent to the dietary tracking and feedback system 1902 for appropriate handling. The predictions that are provided by the dietary prediction system 2104 may be updated periodically or as more information about the imminent food intake event, or other relevant ancillary information, becomes available.

As mentioned previously, the dietary tracking and feedback system 1902 detects the actual start or the probable start of a food intake event, based at least in part on data received from the sensor units 1900. In certain embodiments, the dietary tracking and feedback system 1902 may determine a probability that a food intake event is occurring, and provide the probability information to the medication dosing calculation unit 1906. When making a determination of whether or not a probable or actual start of a food intake event has occurred, and/or when computing the probability that a food intake event is occurring, the dietary tracking and feedback system 1902 may take into account any amount of predictive information 2116 obtained from the dietary prediction system 2104.

As another example, if the dietary tracking and feedback system 1902 determines with a 65% probability or confidence level that a food intake event is occurring, and the dietary prediction system 2104 predicted with a high probability that a food intake event would occur around this time, then the dietary tracking and feedback system 1902 can upwardly adjust its confidence level that a food intake event is currently occurring. Similarly, if the dietary prediction system 2104 predicted a very low probability that a food intake event would occur around this time, then the dietary tracking and feedback system 1902 can downwardly revise its confidence level. In certain embodiments, the dietary tracking and feedback system 1902 may adjust the requirements or criteria used to determine that a food intake event is occurring. For example, the dietary tracking and feedback system 1902 may reduce or increase the number of bite gesture detections required to declare that a meal is occurring. The dietary tracking and feedback system 1902 may take into account other predictive information 2116 output by the dietary prediction system 2104 when declaring food intake events or characteristics of food intake events, and such consideration can impact the manner in which the dietary tracking and feedback system 1902 influences the operation of the medication dosing calculation unit 1906.

In certain embodiments, the measurement sensor processing unit 1909 sends sensor data 2140 or sensor-related signals to the dietary tracking and feedback system 1902. The sensor data 2140 or signals may indicate that a meal event is occurring. For example, if the measurement sensor unit 1904 is a CGM unit, the measurement sensor processing unit 1909 may include logic that analyzes signals received from the measurement sensor unit 1904 and looks for certain patterns, such as a rise in CGM readings, or a change in first or higher order derivative of CGM readings to determine if a food intake event is likely occurring, optionally with an associated probability or confidence level. Other patterns are also possible. The measurement sensor processing unit 1909 may send this information (e.g., sensor data 2140) for use as an input to the dietary tracking and feedback system 1902.

The dietary tracking and feedback system 1902 may also determine a probability that a food intake event is occurring, and provide the probability to the medication dosing calculation unit 1906. When making a determination of whether or not a probable or actual start of a food intake event has occurred, and/or when computing the probability that a food intake event is occurring, the dietary tracking and feedback system 1902 may take into account sensor data 2140 obtained from the measurement sensor processing unit 1909. As an example, if the dietary tracking and feedback system 1902 determines with a 35% probability or confidence level that a food intake event is occurring, and the measurement sensor processing unit 1909 also detects with a high probability that a food intake event is occurring and provides this information to the dietary tracking and feedback system 1902, then the dietary tracking and feedback system 1902 can upwardly adjust its confidence level associated with the determination of the food intake event. Similarly, if the measurement sensor processing unit 1909 does not indicate a food intake event, the dietary tracking and feedback system 1902 may downwardly revise the associated confidence level. Thereafter, the confidence level can be adjusted upwards or downwards as appropriate.

In certain embodiments, the dietary tracking and feedback system 1902 may take into account information, data, or measurements provided by the ancillary event detection system. Thus, any of the ancillary inputs 2106 can also be utilized by the dietary tracking and feedback system 1902. The dietary tracking and feedback system 1902 can process the ancillary inputs 2106 (along with other information) to determine if a food intake event is occurring or likely occurring, and the associated probability or confidence level.

Figure 23:
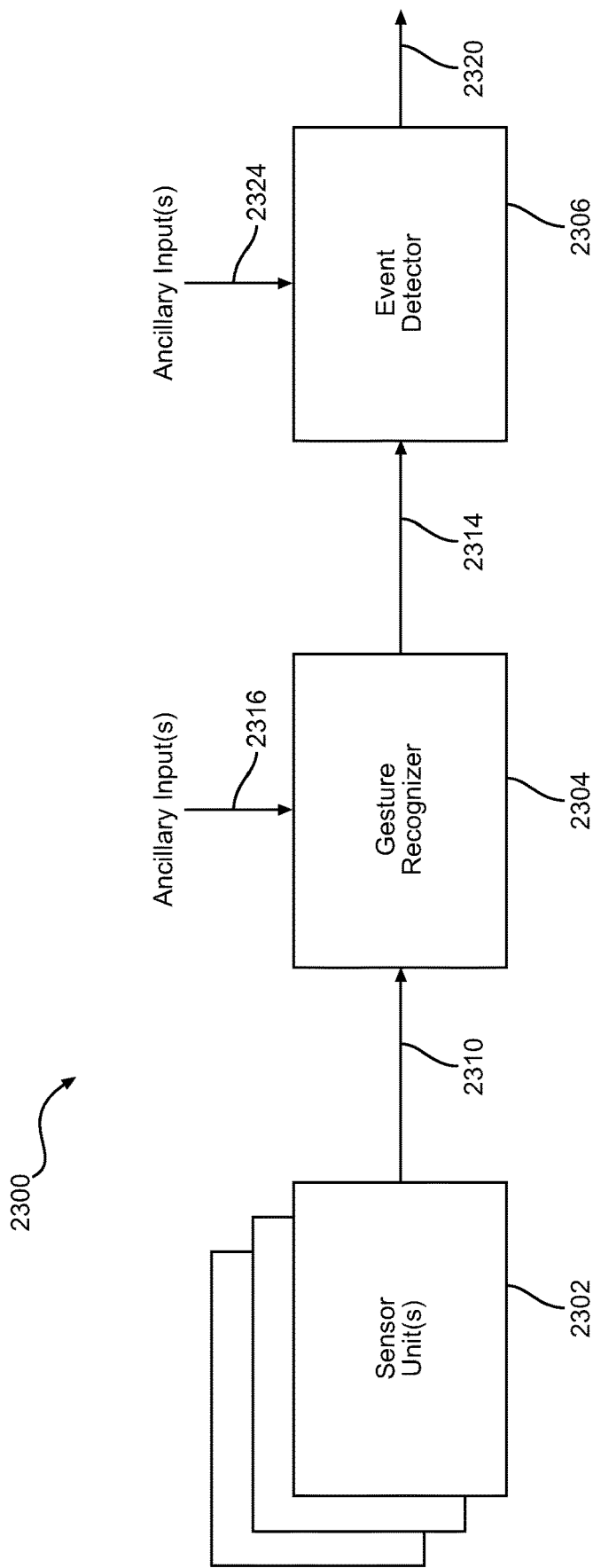
FIG. 23 is a simplified block diagram representation of an embodiment of a gesture-informed physical behavior event detector system.

FIG. 23 is a simplified block diagram representation of an embodiment of a gesture-informed physical behavior event detector system 2300. The depicted embodiment of the system 2300 includes one or more sensor units 2302, a gesture recognizer unit 2304, and a physical behavior event detector 2306. The sensor units 2302 generate one or more sensor data streams 2310, which can be provided to the gesture recognizer unit 2304. A sensor unit 2302 can be realized as any of the following, without limitation: an accelerometer; a gyroscope; or a magnetometer. Although not always required, a sensor unit 2302 can be embedded in a wearable device, component, or article. For example, a wearable device may be worn around the wrist (e.g., an activity tracker or smart watch), around the finger (e.g., a ring), or attached to or worn on a different part of the arm or hand.

The sensor data streams 2310 are provided to the gesture recognizer unit 2304 for processing. To this end, sensor data communicated via the sensor data streams 2310 may be sent in raw format. Alternatively, a sensor unit 2302 may perform some processing (e.g., filtering, compression, or formatting) on raw sensor data before sending the processed sensor data to the gesture recognizer unit 2304. The gesture recognizer unit 2304 analyzes the incoming sensor data and converts the incoming sensor data into a stream of corresponding gestures 2314. The gesture recognizer unit 2304 may use one or more ancillary inputs 2316 to aid in the gesture determination process. Nonlimiting examples of an ancillary input include: time of day; the probability of a specific gesture occurring based on statistical analysis of historical gesture data for that user; geographical location; heart rate; other physiological sensor inputs. Other ancillary inputs are also possible.

Figure 24:
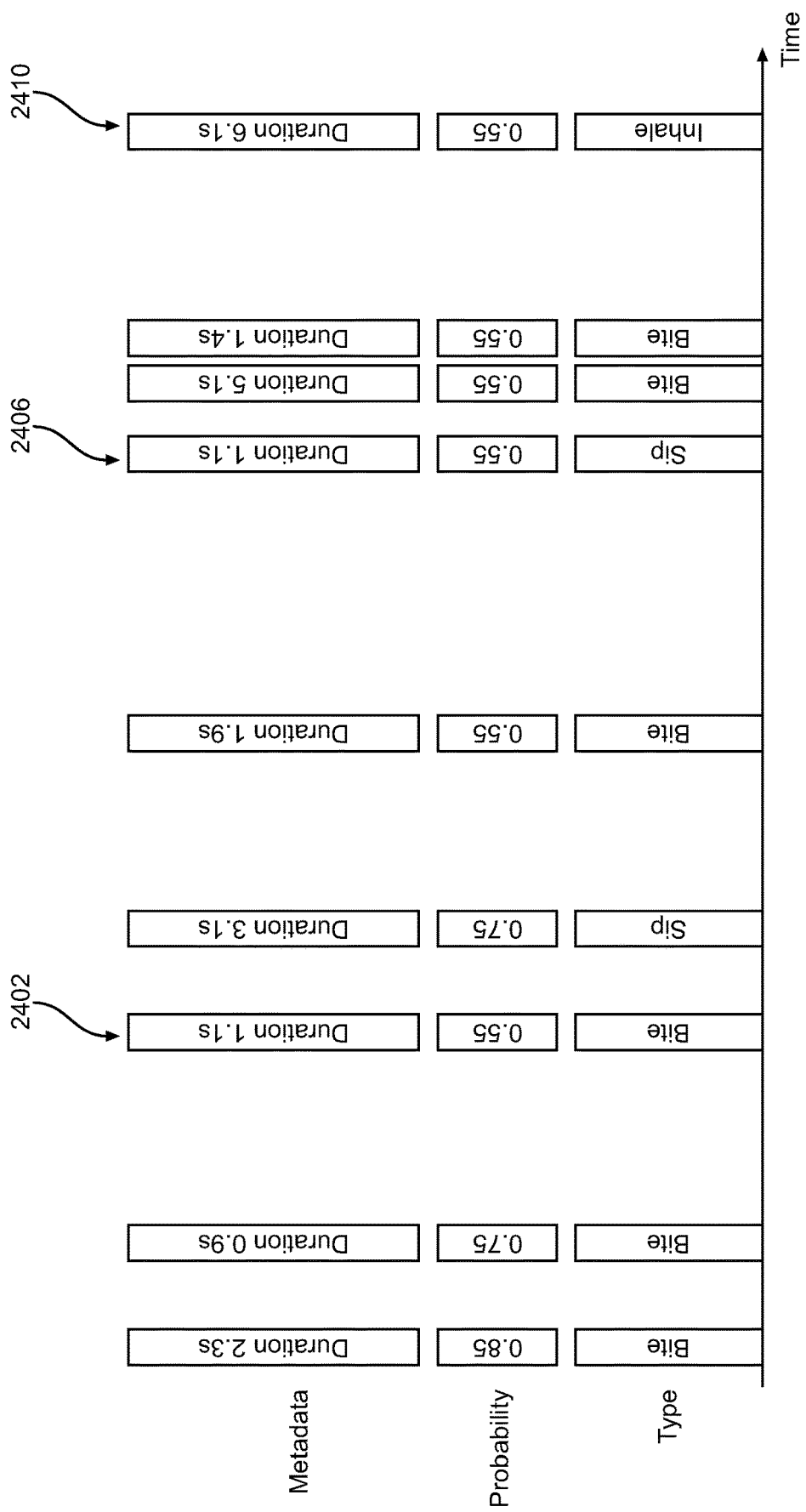
FIG. 24 is a diagram that schematically depicts output of a gesture recognizer unit over time.

FIG. 24 is a diagram that schematically depicts output of the gesture recognizer unit 2304 over time, in accordance with one example. When the gesture recognizer unit 2304 detects a gesture, it generates and sends an output signal that contains at least one of the following: the gesture type (if the gesture recognizer unit 2304 only detects one type of gesture, then this information may be omitted or replaced with a simple binary output signal); the confidence level or probability that the gesture type was determined correctly; and additional metadata such as, for example, the timestamp or the duration of the detected gesture. In this regard, one output 2402 depicted in FIG. 24 corresponds to a detected bite gesture having a probability of 0.55 and a duration of 1.1 seconds. Another output 2406 indicates a detected sip gesture having a probability of 0.55 and a duration of 1.1 seconds. Another output 2410 represents a detected inhale gesture having a probability of 0.55 and a duration of 6.1 seconds.

Figure 25:
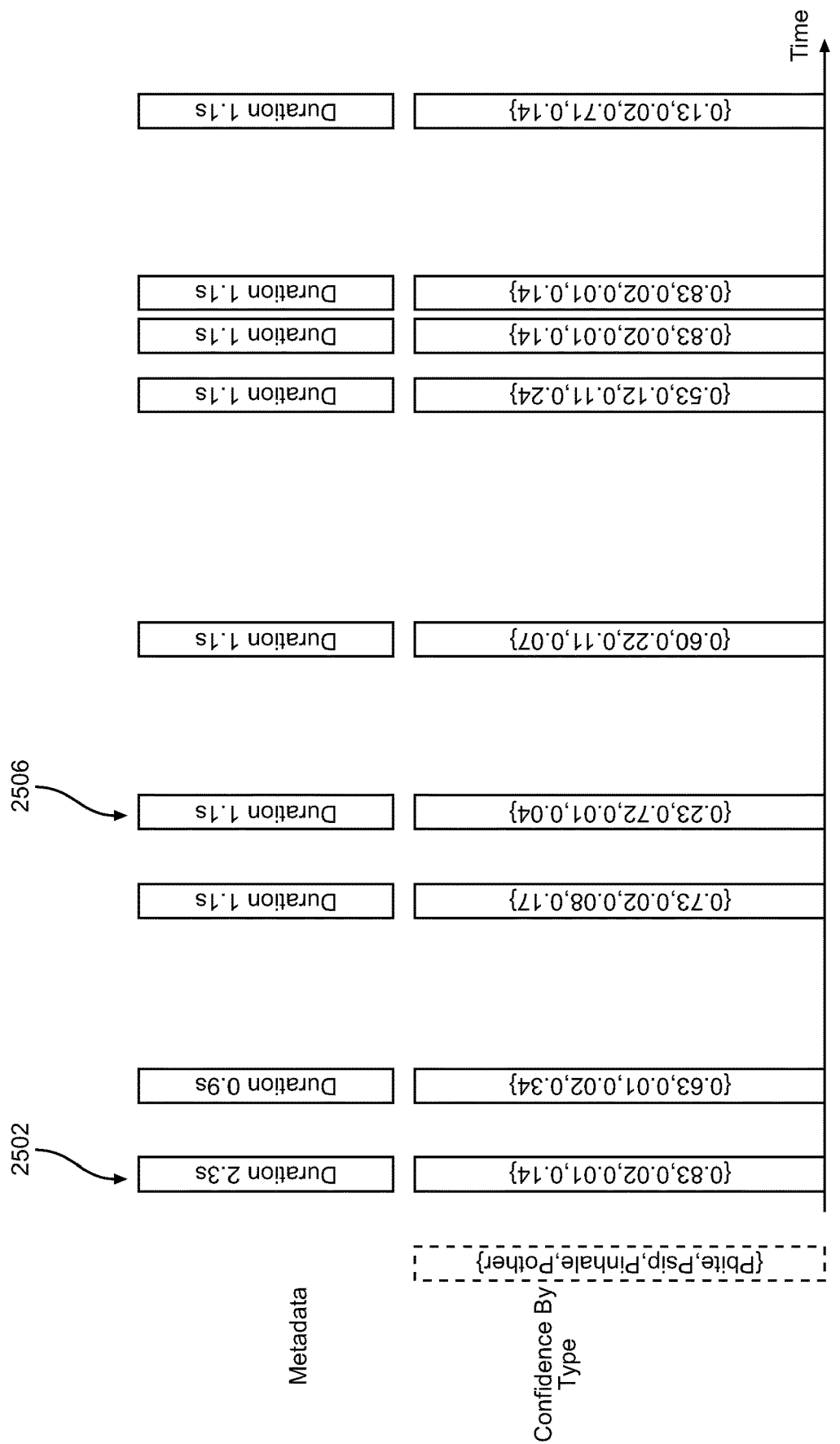
FIG. 25 is a diagram that schematically depicts output of a gesture recognizer unit over time.

FIG. 25 is a diagram that schematically depicts output of the gesture recognizer unit 2304 over time, in accordance with another example. The output shown in FIG. 25 is formatted differently than the output shown in FIG. 24 (other output formats are also possible). In contrast to the example shown in FIG. 24, the output depicted in FIG. 25 includes confidence measurements for different possible gestures, along with corresponding metadata, e.g., the duration of the detected gesture. Although not always required, the implementation contemplated by FIG. 25 considers the following gesture types: bite; sip; and inhale. Accordingly, the output for each detected gesture includes three corresponding confidence measurements—one for a bite gesture, one for a sip gesture, and one for an inhale gesture. The example of FIG. 25 also provides a fourth confidence measurement corresponding to "other" or an "unknown" gesture. In this regard, one output 2502 depicted in FIG. 25 corresponds to a detected gesture having a duration of 2.3 seconds. The output 2502 indicates the following confidence measurements: bite confidence=0.83; sip confidence=0.02; inhale confidence=0.01; "other gesture" confidence=0.14. Accordingly, there is a very high probability that the output 2502 corresponds to a bite gesture. Another output 2506 identifies the following confidence measurements: bite confidence=0.23; sip confidence=0.72; inhale confidence=0.01; "other gesture" confidence=0.04. Thus, there is a very high probability that the output 2506 corresponds to a sip gesture.

Referring again to FIG. 23, the output of the gesture recognizer unit—the detected gestures 2314—are sent to event detector 2306. The event detector 2306 analyzes the incoming stream of gestures 2314 to determine if the start of an event of interest has occurred, whether an event is ongoing, whether an event has ended, or the like. For example, if the event detector 2306 is implemented as a meal detector intended to capture eating/drinking events, it will be suitably configured to determine if the start of a meal has occurred, if a meal is in progress, or if a meal has ended. Other examples of detectable physical behavior or activities (e.g., auxiliary activities) include, without limitation: drinking; smoking; brushing teeth; combing hair; talking on the phone; driving a car; inhaling or injecting a medication; and activities related to hand hygiene or personal hygiene.

The sensor unit(s) 2302, the gesture recognizer unit 2304, and the event detector 2306 may all be housed in the same piece of hardware or may be distributed across multiple pieces of hardware. For example, the sensor unit(s) 2302 may be housed in a wearable device that communicates wirelessly with a second electronic device that houses the gesture recognizer unit 2304 and the event detector 2306. The second electronic device could, for example, be a mobile phone, a medical device such as an insulin pump, an electronic patient health monitor, or the like.

In certain embodiments, the sensor unit(s) 2302, the gesture recognizer unit 2304, and the event detector 2306 are all embedded within a wearable device. The wearable device communicates wirelessly with a second electronic device and the output of the event detector 2306 is sent wirelessly to the second electronic device. As mentioned above, the second electronic device may be implemented as any of the following, without limitation: a mobile phone, a medical device such as an insulin pump, a patient monitor, or the like. In accordance with an alternate arrangement, multiple sensor units 2302 are used and the sensor units 2302 are distributed across at least two wearable devices. Other configurations and partitioning of components across multiple hardware platforms are also possible.

The event detector 2306 obtains the incoming stream of gestures 2314, processes the gestures 2314, and makes a determination about an event state or change in event state based on a review of the received gestures 2314. The event detector 2306 can process the received gestures 2314 to generate a suitably formatted output 2320 that identifies an event state or a change in an event state. The output 2320 can be provided to another system, device, and/or processing logic. The event detector 2306 may use a variety of parameters and decision criteria to determine an event state or a change in event state.

As mentioned above, the event detector 2306 may be implemented as a meal detector. In this context, a meal detector may be configured to have the following states, without limitation: no meal in progress; imminent meal; probable meal in progress; meal in progress; post meal. Different meal states and state transitions were described above with reference to FIG. 22, and the related description may also apply to an implementation of the event detector 2306.

Figure 26:
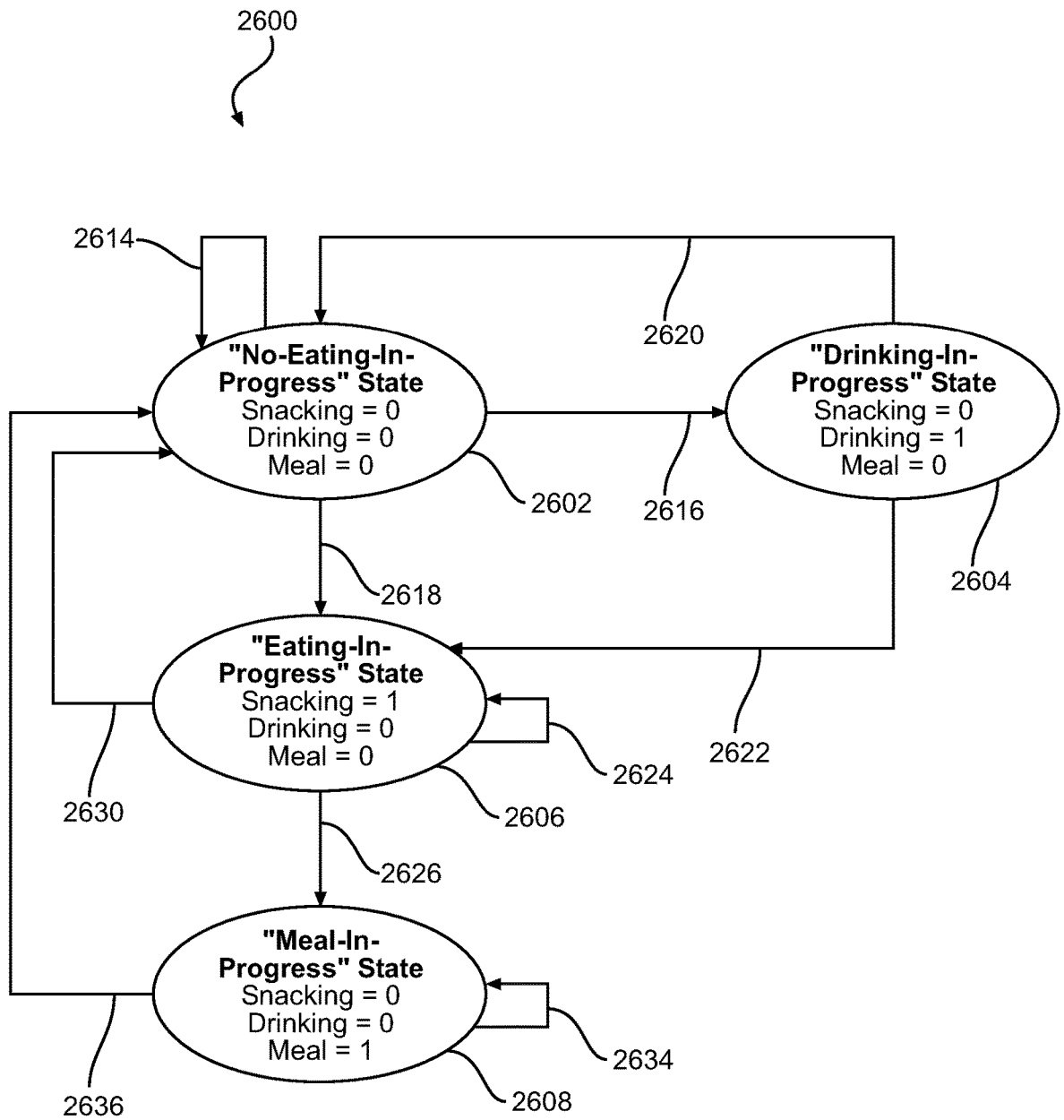
FIG. 26 is a state diagram that applies to an exemplary embodiment of a physical behavior event detector.

FIG. 26 is a state diagram 2600 that applies to an exemplary embodiment of the event detector 2306. For this particular implementation, the states depicted in FIG. 26 are determined based on the gestures 2314 received from the gesture recognizer unit 2304. The state diagram 2600 of FIG. 26 contemplates the following states: No Eating In Progress 2602; Drinking In Progress 2604; Eating In Progress 2606; and Meal In Progress 2608. Additional and/or alternative states can be defined and supported, as appropriate for the particular implementation of the event detector 2306. In FIG. 26, an arrow leading from one state to another state represents a change in the current meal state, and an arrow looping from a state back to itself indicates that the current state does not change.

Based on one or more gestures 2314 received from the gesture recognizer unit 2304, the event detector 2306 may transition from one state to another, while reporting its current state in the form of the output 2320. This example assumes that the event detector 2306 maintains binary indicators for "Snacking" and "Drinking" and "Meal", where a value of "0" refers to a negative condition and a value of "1" refers to a positive condition. Accordingly, the No Eating In Progress state 2602 is indicated when Snacking=0, Drinking=0, and Meal=0. If the event detector 2306 is in the No Eating In Progress state 2602 and no bite gesture is detected, then the No Eating In Progress state 2602 is preserved (as indicated by the loopback arrow 2614). If a sip gesture is detected, then the state changes from the No Eating In Progress state 2602 to the Drinking In Progress state 2604 (as indicated by the arrow 2616). If a bite gesture is detected, then the state changes from the No Eating In Progress state 2602 to the Eating In Progress state 2606 (as indicated by the arrow 2618).

The Drinking In Progress state 2604 is indicated when Snacking=0, Drinking=1, and Meal=0. If the event detector 2306 is in the Drinking In Progress state 2604 and no sip gesture is detected within a specified period of time (e.g., within the last five minutes), then the state changes from the Drinking In Progress state 2604 to the No Eating In Progress state 2602 (as indicated by the arrow 2620). If a bite gesture is detected while the event detector 2306 is in the Drinking In Progress state 2604, then the state changes from the Drinking In Progress state 2604 to the Eating In Progress state 2606 (as indicated by the arrow 2622). For this embodiment, transitioning from the Drinking In Progress state 2604 to the Eating In Progress state 2606 results in the current sip count being carried over into the eating event. The sip count is carried over such that it can be utilized (along with detected bites) when determining whether to remain in the Eating In Progress state 2606 or change to a different state. Thus, counting of sips and bites may continue while in the Eating In Progress state 2606.

The Eating In Progress state 2606 is indicated when Snacking=1, Drinking=0, and Meal=0. If the event detector 2306 is in the Eating In Progress state 2606, a bite gesture or a sip gesture is detected, and designated meal qualification criteria is not met, then the event detector 2306 remains in the Eating In Progress state (as indicated by the loopback arrow 2624). If the event detector 2306 is in the Eating In Progress state 2606, a bite gesture or a sip gesture is detected, and the designated meal qualification criteria is met, then the state changes from the Eating In Progress state 2606 to the Meal In Progress state 2608 (as indicated by the arrow 2626). The meal qualification criteria may include any number of rules or conditions that must be satisfied before the event detector declares that a meal is in progress. The following meal qualification criteria is utilized for this particular example: at least ten bite gestures detected at a median pace of at least 0.8 bites per minute. It should be appreciated that the particular meal qualification criteria may vary from one implementation of the event detector 2306 to another, as appropriate for the embodiment, and as appropriate for the type of event(s) under consideration. If the event detector 2306 is in the Eating In Progress state 2606 and no bite gesture or sip gesture is detected within a specified period of time (e.g., within the last ten minutes), then the state changes from the Eating In Progress state 2606 to the No Eating In Progress state 2602 (as indicated by the arrow 2630).

The Meal In Progress state 2608 is indicated when Snacking=0, Drinking=0, and Meal=1. If the event detector 2306 is in the Meal In Progress state 2608 and a bite gesture or a sip gesture is detected, then the event detector 2306 remains in the Meal In Progress state (as indicated by the loopback arrow 2634). If the event detector 2306 is in the Meal In Progress state 2608 and no bite gesture or sip gesture is detected within a specified period of time (e.g., within the last ten minutes), then the state changes from the Meal In Progress state 2608 to the No Eating In Progress state 2602 (as indicated by the arrow 2636).

FIG. 26 illustrates states and transitions for one exemplary implementation of the event detector 2306, which is configured as a meal detector. In practice, a meal detector can consider parameters such as: the number of gestures classified as bite gestures; the confidence level of bites gestures; inter-bite gesture spacing; elapsed time since detection of the first bite gesture; elapsed time since detection of the last bite gesture; and estimated amounts consumed. Other parameters are also possible.

The decision criteria for determining when to change from a Probable Meal In Progress state to a Meal In Progress state may include, without limitation: reaching or exceeding a specified bite gesture count threshold with a specified inter-bite gesture spacing maximum/time out; reaching or exceeding a specified bite gesture count threshold where each bite reaches or exceeds a specified bite gesture classification confidence level with a specified inter-bite gesture spacing maximum/timeout; reaching or exceeding a specified bite gesture count threshold within a specified time window since detection of the first bite gesture. Other criteria are also possible.

The decision criteria for determining when to change to a Post Meal state or a No Meal In Progress state may include, without limitation: elapsed time since detection of the last bite gesture exceeding a specified time threshold; elapsed time since entering the current state exceeding a specified time threshold. Other criteria are also possible.

A meal detector may signal a change from the No Meal In Progress state to the Meal In Progress state when the state change has occurred ("push approach"). Alternatively, a meal detector may make a state determination only when being queried or on a fixed predetermined schedule ("pull approach"). For example, a system external to the meal detector may request the current meal detector state every two minutes.

In certain embodiments, the event detector 2306 may output a probability or confidence level associated with a state determination. Such probability or confidence level may be updated periodically or when queried.

The event detector 2306 may be a meal detector and the meal detector may process a sequence of bite gestures, optionally along with the confidence level that the gesture was correctly classified as a bite gesture by the gesture recognizer unit 2304 to determine a probability that a meal has started or is in progress. The meal detector may recompute this probability periodically on a fixed schedule, when queried by another module or system, or when one or more new gestures have been received from the gesture recognizer unit 2304. Moreover, the output 2320 of the event detector 2306 may be a probability that is indicative of the overall probability that an event has started or is ongoing.

As shown in FIG. 23, the event detector 2306 may use ancillary inputs 2324 to make a state determination or compute a state probability. For example, if the event detector 2306 is implemented as a meal detector, then the event detector 2306 (or a system interfacing with the event detector 2306) may derive the probability that a user is eating from the historical eating records from the user, and the meal detector may take this probability into account when determining whether or not to declare the Meal In Progress state. As an example, if the historical probability that a user is eating is 90% (suggesting that in nine out of ten cases in the past, the user was determined to be eating at this time or within a time window around this time in the past), the meal detector may use a lower bite count threshold to change to the Meal In Progress state. In contrast, if the historical probability that the user is eating is only 10% (suggesting that only in one out of ten cases in the past, the user was determined to be eating at this time or within a time window around this time in the past), the meal detector may decide to use a higher bite count threshold. In case of a probabilistic meal detector, the meal detector may weigh the probability that a meal has started or is in progress with the historical probability.

Heart rate may be another ancillary input 2324. Blood glucose readings (or blood sugar readings derived from interstitial fluid) and/or changes in blood glucose readings (or blood sugar readings derived from interstitial fluid) may be another ancillary input 2324. An ancillary input 2324 may be an input provided by the user, such as a confirmation that the user is eating, or it may be a measurement or data provided by an electronic device, a sensor component, or the like.

The event detector 2306 may also take into account inputs from an external event prediction system (such as the dietary prediction system 2104 described above with reference to FIG. 21) to make a state or state change determination or compute a state probability. If the external event prediction system is a meal prediction system, and the meal prediction system informs the event detector 2306 that there is a high likelihood that the user is about to start eating, the event detector 2306 may use more aggressive criteria to declare the Meal In Progress state (e.g., lower bite count threshold) or boost the computed Meal In Progress state probability. If the external event prediction system is a sleep prediction system, and the sleep prediction system informs the event detector 2306 that there is a high likelihood that the user is sleeping, the event detector 2306 may use more conservative criteria to declare the Meal In Progress state (e.g., increase bite count threshold) or reduce the computed Meal In Progress state probability. If an event prediction system predicts that the likelihood of an event occurring is low, the confidence levels of the gestures 2314 considered by the event detector 2306 may be reduced by an absolute amount or a proportional factor.

Figure 27:
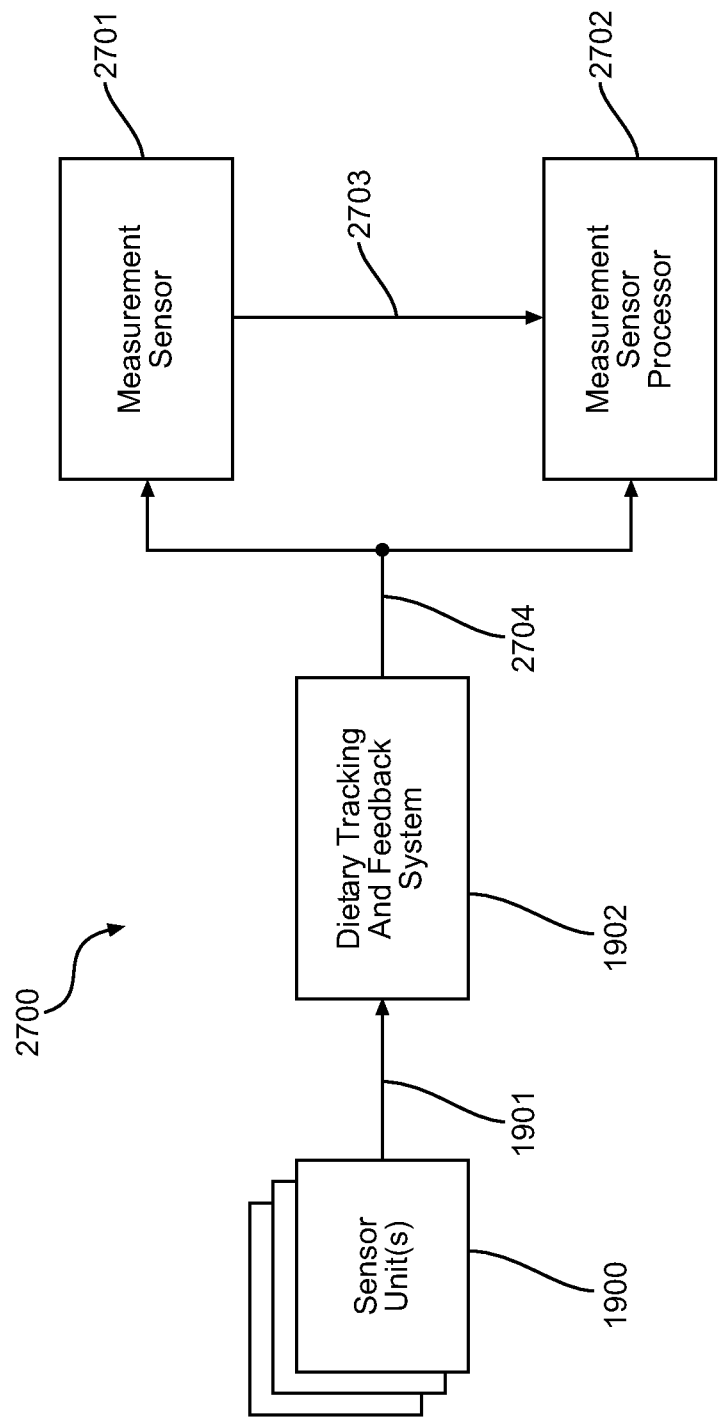
FIG. 27 is a simplified block diagram representation of functional components of a medication dispensing system.

FIG. 27 is a simplified high-level functional diagram of certain components of a medication dispensing system 2700 that employs physical behavior detection (in the form of a dietary/meal tracking and feedback system). The illustrated system 2700 includes various blocks that represent functional modules, devices or hardware elements, and/or processing logic. Moreover, the depicted embodiment of the system 2700 includes functional modules and related processing logic that are similar to those described above with reference to the exemplary systems shown in FIG. 19 and FIG. 21. Accordingly, common reference numbers are used in FIGS. 19, 21, and 27 to indicate similar, identical, or equivalent blocks or signals. In this regard, the system 2700 includes or cooperates with sensor units 1900, the dietary tracking and feedback system 1902, at least one measurement sensor 2701 (e.g., a measurement sensor unit 1904 as depicted in FIG. 21) that generates sensor data indicative of a physiological characteristic of the user, and a measurement sensor processor 2702 (e.g., a measurement sensor processing unit 1909 as depicted in FIG. 21) that processes the sensor data generated by the measurement sensor 2701. For clarity and ease of illustration, the other components and interconnections shown in FIG. 21 are omitted from FIG. 27. It should be appreciated that the components depicted in FIG. 27 are suitably configured, arranged, and operated for compatibility with the arrangement shown in FIG. 21.

As mentioned above, sensor data 1901 from the sensor units 1900 is processed by the dietary tracking and feedback system 1902, which generates an output associated with a detected physical behavior event, e.g., a meal event. The measurement sensor 2701 generates sensor output 2703 that is provided to the measurement sensor processor 2702. Output of the measurement sensor processor 2702 is utilized as needed. For example, the output of the measurement sensor processor 2702 can be provided to the medication dosing calculation unit 1906 (see FIG. 21). In certain implementations, the output of the measurement sensor processor 2702 can be provided to the dietary tracking and feedback system 1902 as an input to consider when determining whether a gesture-based physical behavior event of interest has occurred or is likely to occur, as described previously.

In certain deployments of the system 2700, the measurement sensor 2701 includes or is realized as a continuous glucose monitor or a continuous glucose sensor device. A continuous glucose monitor works well when the detected occurrence of the gesture-based physical behavior event corresponds to a food intake event. In such an embodiment, the medication can be insulin, and the system calculates and dispenses a dosage of insulin in response to the detected food intake event and in response to the user's blood glucose level as measured by the continuous glucose monitor.

In accordance with the embodiment presented here, output 2704 of the dietary tracking and feedback system 1902 may be provided to the measurement sensor unit 1904 and/or to the measurement sensor processing unit 1909. In turn, certain functions, features, settings, or operations of the measurement sensor unit 1904 and/or the measurement sensor processing unit 1909 can be adjusted, varied, or otherwise modified based on the output 2704 received from the dietary tracking and feedback system 1902.

For example, when the dietary tracking and feedback system 1902 detects the actual or probable start of an event of interest, it may send a suitably formatted output 2704 or signal to the measurement sensor unit 1904 and/or the measurement sensor processing unit 1909. Upon receiving the output 2704, or some time thereafter, the measurement sensor unit 1904 and/or the measurement sensor processing unit 1909 may initiate an appropriate state change. Such a state change may include any of the following, without limitation: (1) activating a higher performance mode of one or more circuits or components; (2) supplying additional power to one or more circuits; (3) increasing the sampling rate of the measurement sensor unit 1904; (4) reducing latency of a communication channel such as an increased sensor read out frequency, or a reduced latency in communication between the measurement sensor processing unit 1909 and the medication dosing calculation unit 1906 (see FIG. 21); (5) increasing buffer space allocated for data storage. Other actions are also possible.

Equivalently, when the dietary tracking and feedback system 1902 detects the end or probable end of an event of interest, it may send an output 2704 or an output signal to the measurement sensor unit 1904 and/or the measurement sensor processing unit 1909. Upon receiving the output 2704, or some time thereafter, the measurement sensor unit 1904 and/or the measurement sensor processing unit 1909 may initiate a state change. Such a state change may include any of the following, without limitation: (1) deactivating one or more circuits or components; (2) placing one or more circuits or components in a lower performance mode; (3) placing one or more circuits or components in a lower power mode; (4) reducing the power supplied to one or more circuits or components; (5) reducing the sampling rate of one or more circuits or components; (6) increasing the latency of a communication channel such as reducing a sensor read out frequency; (7) reducing a buffer space allocated for data storage. Other actions are also possible. In this way, the system may conserve battery life and/or processing capacity.

For consistency with FIG. 19 and FIG. 21, the system 2700 has been described with reference to the dietary tracking and feedback system 1902. In practice, however, any type of physical behavior can be tracked and detected in the context of the system 2700. Accordingly, the measurement sensor unit 1904 and/or the measurement sensor processing unit can be adjusted in an ongoing manner based on the detection of physical behavior events that need not be explicitly linked to eating, drinking, meal consumption, etc.

Figure 28:
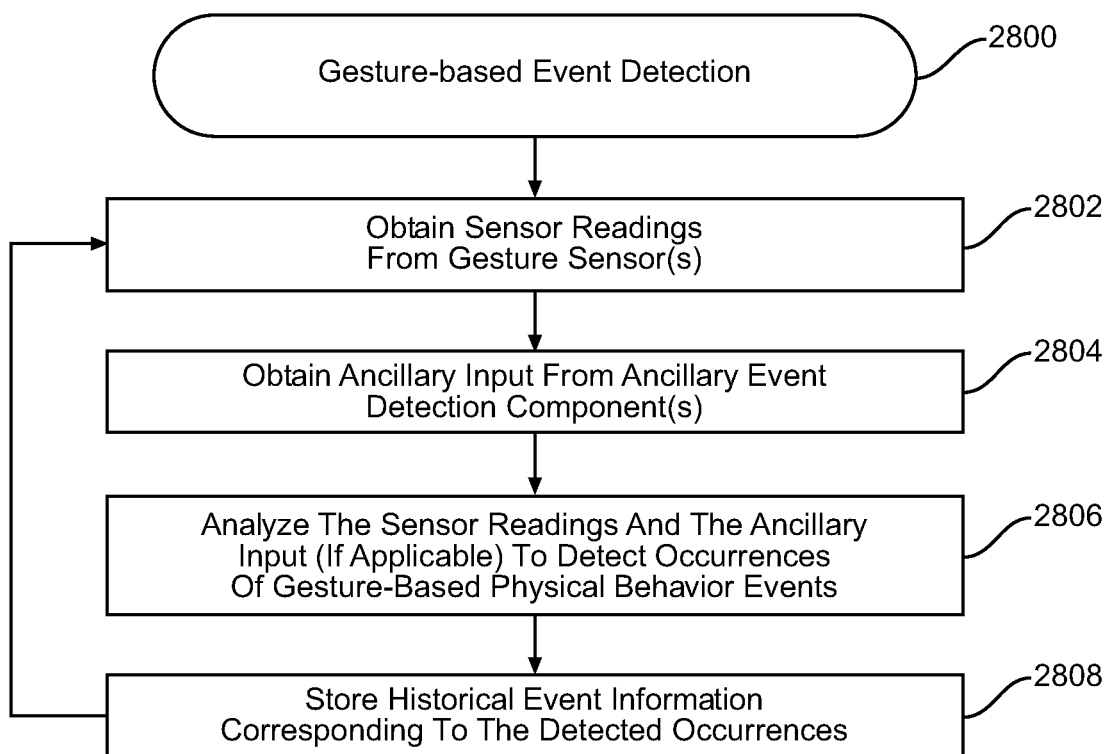
FIG. 28 is a flow chart that illustrates an exemplary embodiment of a gesture-based physical behavior detection process.
Figure 29:
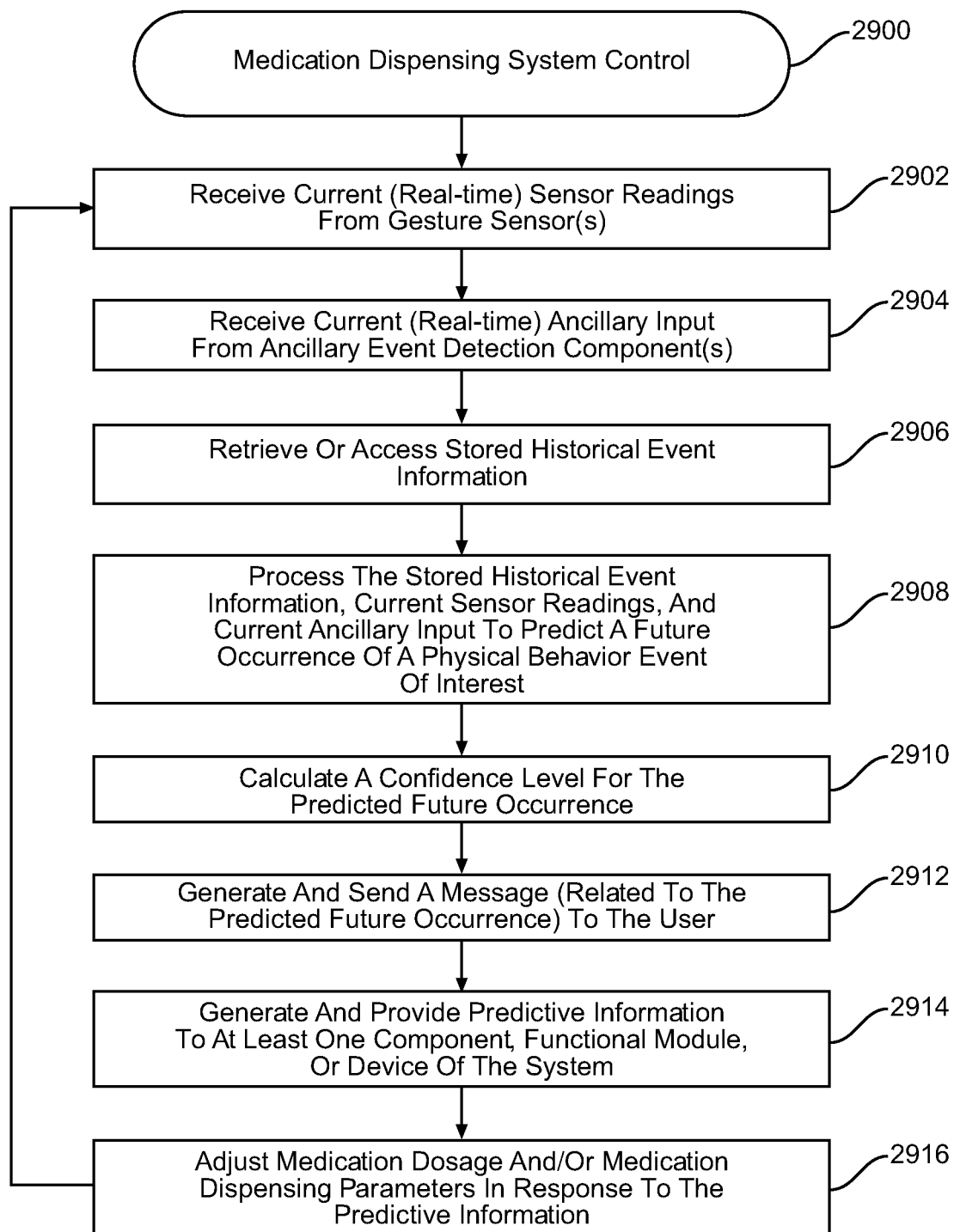
FIG. 29 is a flow chart that illustrates an exemplary embodiment of a process for controlling operation of a medication dispensing system, based on a predicted occurrence of a behavior event.

FIG. 28 is a flow chart that illustrates an exemplary embodiment of a gesture-based physical behavior detection process 2800, and FIG. 29 is a flow chart that illustrates an exemplary embodiment of a process 2900 for controlling operation of a medication dispensing system in a manner that is influenced by detected gestures.

The physical behavior detection process 2800 relates to the manner in which the dietary tracking and feedback system 1902 operates to detect user gestures and associated gesture-based physical behavior events, which in turn can be used by the dietary prediction system 2104 in an ongoing manner. Accordingly, this description of the process 2800 refers to historical or previously-detected events that can be leveraged by the system while detecting ongoing events in a real-time manner.

The illustrated embodiment of the process 2800 obtains sensor readings from one or more gesture sensors (task 2802), e.g., the sensor units 1900 shown in FIG. 21 or sensors used by the sensor units 1900. As explained above, the sensor readings indicate, measure, or identify movement, motion, or positional change of at least one specific body part of the user. Optionally, the process 2800 may obtain ancillary input from at least one ancillary input component, such as the components, units, or sensors associated with the ancillary event detection system 2102 (task 2804). In certain embodiments, the ancillary event detection system 2102 and its associated ancillary input components are distinct from the gesture sensors. In this regard, the gesture sensors may be realized as user-worn or user-carried sensor devices having accelerometer and/or gyroscope elements, and the ancillary input components may be realized as physically distinct and separate devices that are designed to sense or detect other conditions, phenomena, user status, and/or environmental states that are not directly related to body movement or user gestures. For the dietary tracking embodiment described here, the gesture sensors are configured and operated to obtain sensor data used to detect physical gestures that are directly related to (or directly indicate) eating or drinking movements, such as bites, sips, chewing, motion corresponding to the use of eating utensils, etc. For such an embodiment, the ancillary input may include any type or amount of information that might be correlated to or only indirectly associated with an eating event, a drinking event, or a food intake event.

The process 2800 continues by analyzing the received sensor readings and the received ancillary input (if applicable) to detect or declare occurrences of certain gesture-based physical behavior events (task 2806). In practice, the analysis performed at task 2806 primarily relies on the information obtained from the gesture sensors, as described in detail above. Nonetheless, ancillary input can also be leveraged to better inform the decision made at task 2806, to improve the reliability of the determination, and the like. This description assumes that the process 2800 detects a number of gesture-based physical behavior events over time, and assumes that information and/or metadata associated with detected events is saved in a suitably configured data storage device. More specifically, the process 2800 stores historical event information corresponding to the detected occurrences of the gesture-based physical behavior events (task 2808). The stored event information may include any of the following, without limitation: the type of gesture detected (e.g., bite, sip, inhale, knife cut gesture, utensil usage gesture); the number of times each type of gesture was detected during a period of time (e.g., the last 24 hours, the last hour, the last 15 minutes or any other period of time); a probability or confidence measure for the detected gesture; the duration of the gesture; time/date stamp data; ancillary data associated with the ancillary input; the type of event detected (e.g., eating a meal, drinking coffee, eating a snack, cooking); a probability or confidence measure for the detected event; the duration of the event. Over time, a rich database of historical event information can be maintained to provide a good foundation for the prediction system.

Referring to FIG. 29, the following description of the system control process 2900 assumes that at least a baseline amount of historical event information has already been saved for use with ongoing processing of real-time gesture sensor measurements. The illustrated embodiment of the process 2900 receives current sensor readings obtained from the gesture sensors in real-time (task 2902). The process 2900 may also receive at least one ancillary input 2106 from the detection system 2102, which is distinct from the gesture sensors (task 2904). The gesture sensors and corresponding sensor readings, and the detection system 2102 and corresponding ancillary input 2106 were described in detail above. The current gesture sensor readings and ancillary input (if applicable) can be reviewed with historical event information to carry out the prediction techniques described herein. Accordingly, the process 2900 retrieves or accesses at least some of the stored historical event information (task 2906).

The stored historical event information is processed at task 2908 to predict a future occurrence of a physical behavior event of interest. Although not always required, the processing at task 2908 may also consider the current gesture sensor readings and/or the current ancillary input when generating the prediction. Task 2908 analyzes the historical event information to predict whether a particular physical behavior event is likely to occur in the future. At least some of the current sensor readings can be compared to stored historical event information during this analysis. Various prediction methodologies and examples were described above with reference to FIG. 21 and, more specifically, with reference to the dietary prediction system 2104. The process 2900 can leverage any of the previously described techniques and methodologies to predict future occurrences of physical behavior events.

In certain embodiments, task 2908 may also consider the current gesture sensor readings, which might increase the accuracy of the prediction. Accordingly, task 2908 may predict the future occurrence of the event based on certain characteristics of a currently detected gesture-based physical behavior event. Task 2908 may also consider current ancillary input(s) to increase the accuracy of the prediction. In this regard, the process 2900 may calculate a probability or confidence level for the predicted future occurrence of the event (task 2910). For example, the process 2900 may declare that a predicted food intake event will occur within the next 15 minutes, with a corresponding probability or confidence level, such as 83% probability. The probability or confidence level may be calculated from a review of the historical event information, with or without additional sensor data or status information collected in real-time.

In certain embodiments, the process 2900 generates and sends a message to the user—the message conveys information or content that is related to the predicted future occurrence of the event of interest (task 2912). For example, task 2912 may initiate delivery or display of a notification, email, or text message to the user, where the delivered content identifies the predicted event, a predicted time of the event, the probability or confidence level, and possibly a recommendation or advice regarding actions that the user should take (e.g., medication dosage, carbohydrate consumption, or the like).

The process 2900 may also generate and provide predictive information to at least one component, functional module, or device of the system (task 2914). For this example, the dietary prediction system 2104 of FIG. 21 provides predictive information 2116 to the medication dosing calculation unit 1906 and, optionally, to the dietary tracking and feedback system 1902. In this context, the predictive information provided at task 2914 may include any of the following, without limitation: the predicted event (e.g., food intake, eating dinner, drinking a beverage, consuming a snack, performing a physical activity that is being monitored); the probability or confidence measure for the predicted event; and a predicted start time, end time, and/or duration of the predicted event. The predictive information provided at task 2914 can be used to adjust medication dosage, medication dispensing parameters, or both (task 2916). In this regard, the predicted future occurrence of the physical behavior event of interest and its calculated confidence level can be processed to influence the medication dosage and/or medication dispensing parameters. In accordance with the insulin delivery implementation described herein, the predicted event is a food intake event, the medication managed by the system is insulin, and task 2916 calculates an appropriate dosage of insulin to be administered under the assumption that the predicted food intake event will actually occur. As another example, the message sent at task 2912 may inform the user that the system has predicted an upcoming food intake event, and recommend an appropriate bolus dose of insulin for the predicted food intake event.

Figure 30:
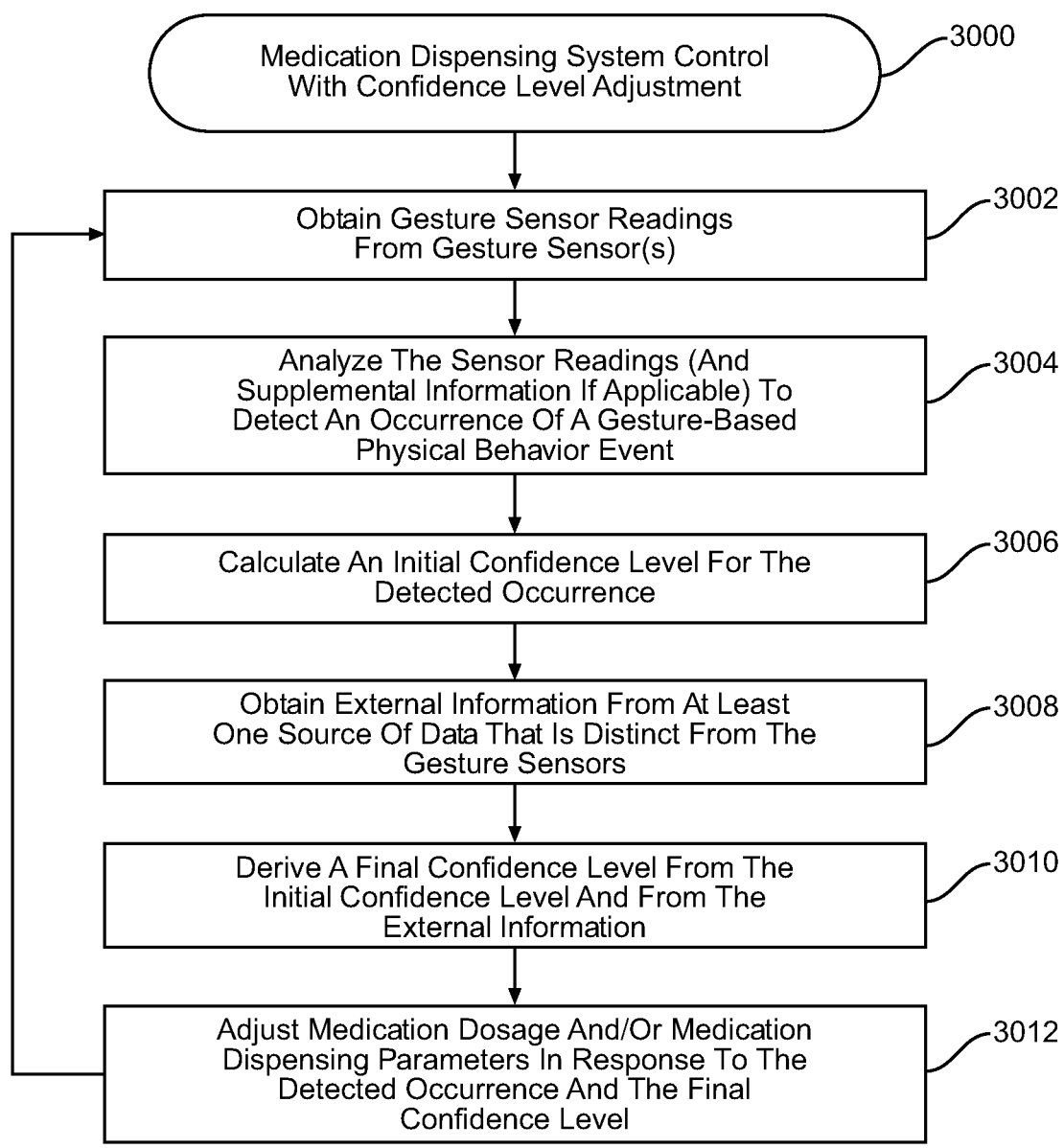
FIG. 30 is a flow chart that illustrates an exemplary embodiment of a process for controlling operation of a medication dispensing system, which includes the adjustment of a confidence level for a detected gesture-based behavior event.

FIG. 30 is a flow chart that illustrates an exemplary embodiment of a process 3000 for controlling operation of a medication dispensing system, which includes the adjustment of a confidence level for a detected behavior event. The process 3000 may be implemented as a part of, or performed in association with, one or more of the other system control processes described elsewhere herein. Indeed, one or more of the tasks shown in FIG. 30 may be similar or equivalent to counterpart tasks described with reference to FIG. 28 or FIG. 29. For the sake of brevity and clarity, similar or equivalent tasks or aspects of the process 3000 will not be redundantly described in detail here.

The illustrated embodiment of the process 3000 obtains gesture sensor readings from one or more gesture sensors of the system (task 3002), as described above with reference to task 2802 of FIG. 28 and in other contexts. The sensor readings are analyzed and processed to detect an occurrence of a gesture-based physical behavior event (task 3004). In certain embodiments, the analysis and processing performed at task 3004 also considers supplemental information (data generated by sources other than the gesture sensors), as described above with reference to task 2806 of FIG. 28 and in other contexts.

The process 3000 calculates an initial confidence level for the detected occurrence of the gesture-based physical behavior event (task 3006), as described above with reference to task 2910 of FIG. 29 and in other contexts. The process 3000 continues by obtaining external information from at least one source of data this is distinct from the gesture sensors (task 3008). In this regard, the external information can be supplemental or ancillary data other than the gesture sensor data. For example, the at least one source of data may include the ancillary detection system 2102 (see FIG. 21 and the related description), which is physically distinct from the gesture sensors. As explained above, the ancillary detection system 2102 may include or cooperate with at least one component configured to generate user status information that is not directly related to user gestures or the detection of user gestures. The external information processed at task 3008 may include any amount of the user status information provided by the component(s) of the ancillary detection system 2102. Accordingly, the user status information may include any of the various types of ancillary input 2106 mentioned above with reference to FIG. 21.

As another example, the at least one source of data may include a measurement sensor unit 1904 (see FIG. 21 and the related description) that generates sensor data indicative of a physiological characteristic of the user. Alternatively or additionally, the at least one source of data may include the measurement sensor processing unit 1909 that cooperates with the measurement sensor unit 1904. For this example, therefore, the external information processed at task 3008 may include the sensor data generated by the measurement sensor unit 1904 and/or the measurement sensor processing unit 1909.

As another example, the at least one source of data may include a prediction system configured to predict future occurrences of gesture-based physical behavior events, wherein the external information includes predictive information generated by the prediction system. In this context, the predictive information describes, characterizes, or defines a predicted future occurrence of a gesture-based physical behavior event. In certain embodiments, the detected occurrence of the gesture-based physical behavior event corresponds to a food intake event, and the prediction system is implemented as the dietary prediction system 2104 (see FIG. 21 and the associated description).

Any or all of the available external information can be used to modify, adjust, or verify the initial confidence level calculated at task 3006. More specifically, the process 3000 may continue by deriving a final confidence level for the detected occurrence of the gesture-based physical behavior event (task 3010). The final confidence level is derived from the initial confidence level and from at least some of the external information obtained from the source(s) of external data. Thus, if the external information further indicates that the gesture-based physical behavior event of interest has occurred or is likely to occur, then task 3008 can increase the initial confidence level. Conversely, if the external information does not support or agree with the determination made at task 3004, then task 3008 can decrease the initial confidence level. If the external information is "neutral" or is otherwise insufficient to influence the initial confidence level, then task 3008 can preserve the initial confidence level.

The process 3000 may continue by adjusting the medication dosage and/or the medication dispensing parameters in response to the detected occurrence of the gesture-based physical behavior event and in response to the final confidence level (task 3012). Task 3012 is similar to task 2916 described above with reference to FIG. 29. For a detected food intake event, task 3012 can calculate the dosage of insulin to be delivered to the user, along with certain insulin dispensing parameters. The final confidence level may be used to influence the aggressiveness of the medication treatment, the dosage, or the like. For example, if the final confidence level is very high, then a first dosage of insulin may be calculated for the detected food intake event. If, however, the final confidence level is below a confidence threshold (e.g., only about 80%), then a second (lower) dosage of insulin may be calculated as a safe measure. The rate of insulin delivery may also be adjustable based on the final confidence level. These and other examples are contemplated by the process 3000.

Figure 31:
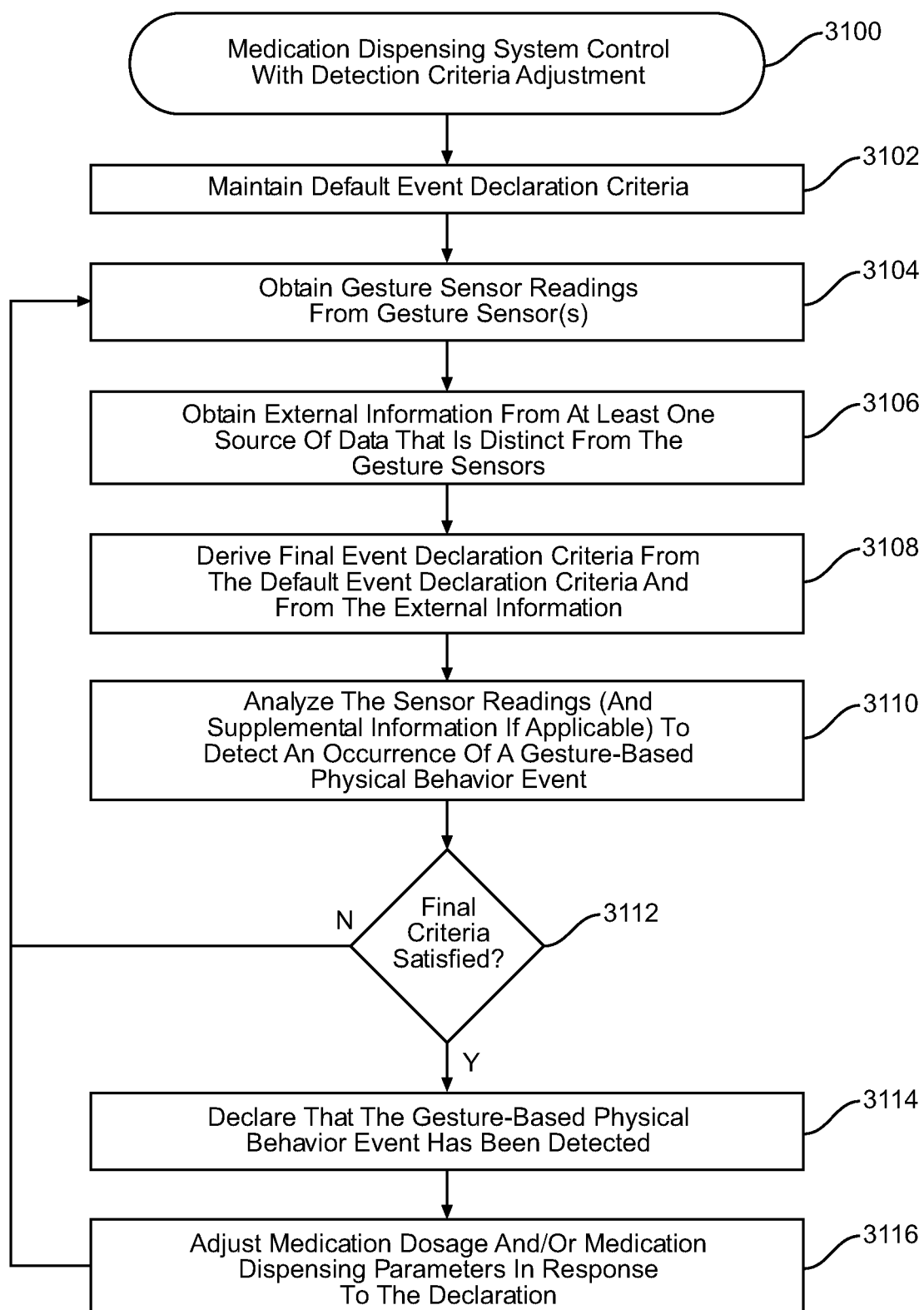
FIG. 31 is a flow chart that illustrates an exemplary embodiment of a process for controlling operation of a medication dispensing system, which includes the adjustment of criteria used to determine whether a gesture-based behavior event has occurred.

FIG. 31 is a flow chart that illustrates an exemplary embodiment of a process 3100 for controlling operation of a medication dispensing system, which includes the adjustment of criteria used to determine whether a gesture-based behavior event has occurred. The process 3100 may be implemented as a part of, or performed in association with, one or more of the other system control processes described elsewhere herein. Indeed, one or more of the tasks shown in FIG. 31 may be similar or equivalent to counterpart tasks described with reference to FIG. 28, FIG. 29, or FIG. 30. For the sake of brevity and clarity, similar or equivalent tasks or aspects of the process 3100 will not be redundantly described in detail here.

The illustrated embodiment of the process 3100 maintains default event declaration criteria for use in determining whether a gesture-based physical behavior event of interest has occurred or is likely to occur (task 3102). The default criteria can be maintained in a suitably configured and formatted memory or data storage element of the system. Examples of event declaration criteria were described above with reference to FIGS. 23-26. Event declaration criteria may include, for example: the type of gesture(s) detected; the number of each gesture detected per unit of time; probability or confidence levels associated with detected gestures; the presence of designated sequences or patterns of gestures; and the like. In this regard, default event declaration criteria can be maintained for any number of gesture-based physical behavior events that the system intends to monitor.

The process 3100 obtains gesture sensor readings from one or more gesture sensors of the system (task 3104), as described above with reference to task 2802 of FIG. 28 and in other contexts. The process 3100 also obtains external information from at least one source of data this is distinct from the gesture sensors (task 3106). The external information and possible sources of external information were described above with reference to task 3008 of the process 3000, and that description also applies here in the context of process 3100. Accordingly, the at least one source of data may include, without limitation: the ancillary detection system 2102; the measurement sensor unit(s) 1904; the measurement sensor processing unit 1909; and/or a prediction system such as the dietary prediction system 2104.

Any or all of the available external information can be used to modify, adjust, or preserve the default event declaration criteria. More specifically, the process 3100 may continue by deriving final event declaration criteria for use in determining whether the gesture-based physical behavior event of interest has occurred or is likely to occur (task 3108). The final event declaration criteria are derived from the default event declaration criteria and from at least some of the external information obtained from the source(s) of external data. Thus, if the external information indicates with high confidence that the gesture-based physical behavior event of interest has occurred or is likely to occur, then task 3108 can decrease or relax the requirements of the default event declaration criteria. Conversely, if the external information indicates with low confidence that the event of interest has occurred or is likely to occur, or that the event of interest has not or will not occur, then task 3108 can increase or tighten the requirements of the default event declaration criteria for that event. If the external information is "neutral" or is otherwise insufficient to influence the default event declaration criteria, then task 3108 can preserve the default criteria.

The gesture sensor readings are analyzed and processed to detect an occurrence of the gesture-based physical behavior event of interest (task 3110). In certain embodiments, the analysis and processing performed at task 3110 also considers supplemental information (data generated by sources other than the gesture sensors), as described above with reference to task 2806 of FIG. 28 and in other contexts. The system applies and considers the final event declaration criteria to determines whether the gesture-based physical behavior event of interest has occurred or is likely to occur (query task 3112). When the obtained gesture sensor readings satisfy the final event declaration criteria (the "Yes" branch of query task 3112), the process 3100 declares a detection of that particular gesture-based physical behavior event (task 3114). If the criteria is not satisfied (the "No" branch of query task 3112), then the process 3100 may exit or return to task 3104 for continued monitoring and processing of gesture sensor readings.

The process 3100 may continue by adjusting the medication dosage and/or the medication dispensing parameters in response to the declared occurrence of the gesture-based physical behavior event (task 3116). Task 3116 is similar to task 2916 described above with reference to FIG. 29. For a detected food intake event, task 3116 can calculate the dosage of insulin to be delivered to the user, along with certain insulin dispensing parameters.

Figure 32:
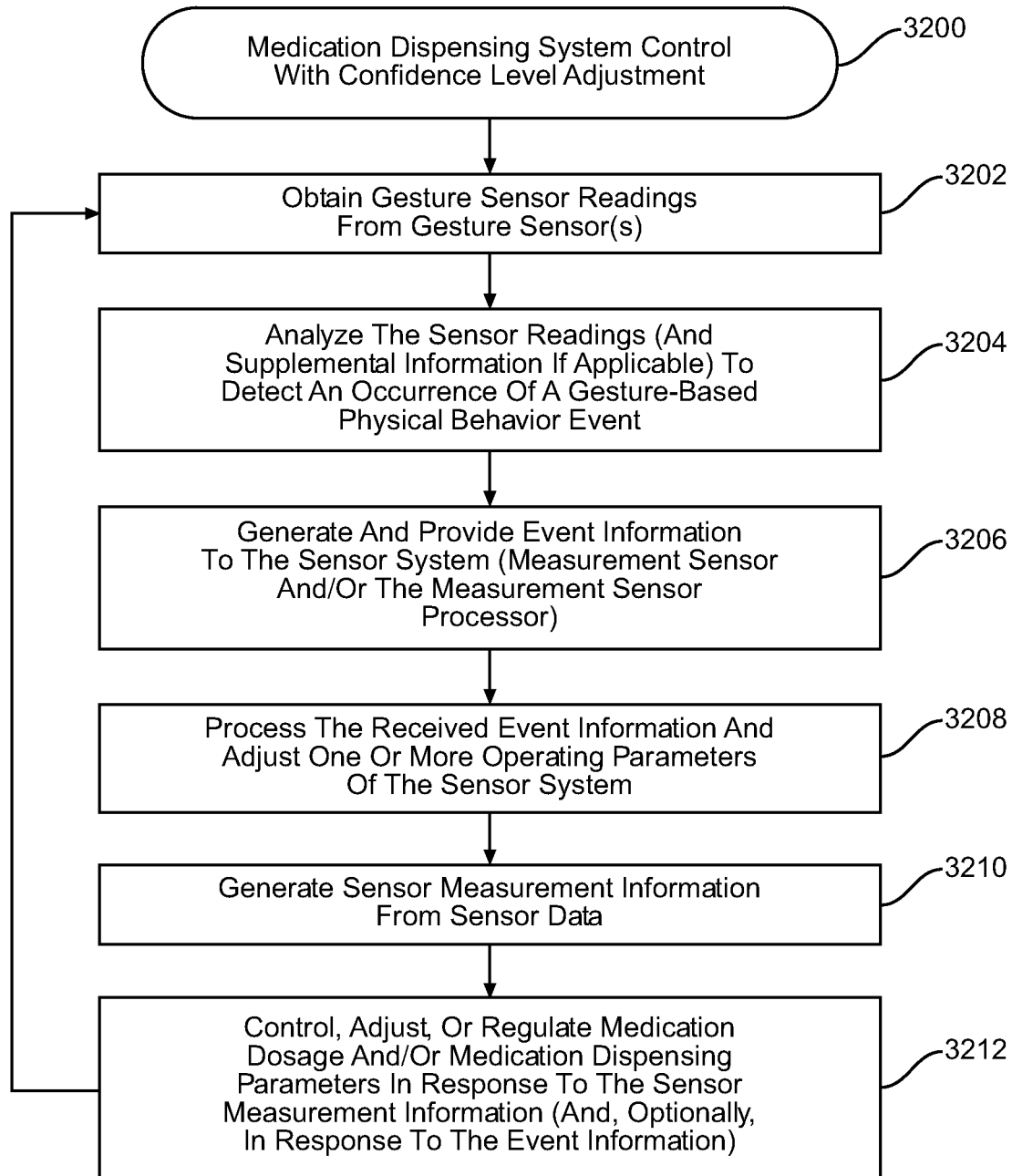
FIG. 32 is a flow chart that illustrates an exemplary embodiment of a process for controlling operation of a medication dispensing system, which includes the adjustment of at least one sensor system operating parameter in response to the detection of a gesture-based behavior event.

FIG. 32 is a flow chart that illustrates an exemplary embodiment of a process 3200 for controlling operation of a medication dispensing system, which includes the adjustment of at least one sensor system operating parameter in response to the detection of a gesture-based behavior event. The process 3200 may be implemented as a part of, or performed in association with, one or more of the other system control processes described elsewhere herein. Indeed, one or more of the tasks shown in FIG. 32 may be similar or equivalent to counterpart tasks described with reference to FIGS. 28-31. For the sake of brevity and clarity, similar or equivalent tasks or aspects of the process 3200 will not be redundantly described in detail here.

The illustrated embodiment of the process 3200 obtains gesture sensor readings from one or more gesture sensors of the system (task 3202), as described above with reference to task 2802 of FIG. 28 and in other contexts. The sensor readings are analyzed and processed to detect an occurrence of a gesture-based physical behavior event (task 3204). In certain embodiments, the analysis and processing performed at task 3204 also considers supplemental information (data generated by sources other than the gesture sensors), as described above with reference to task 2806 of FIG. 28 and in other contexts.

In response to the detection of a gesture-based physical behavior event, the process 3200 generates and provides corresponding event information to a component of the sensor system (task 3206), wherein the sensor system includes, for example, the measurement sensor 2701 and/or the measurement sensor processor 2702 shown in FIG. 27. The event information includes data that describes, characterizes, or defines the detected occurrence of the gesture-based physical behavior event, such as a food intake event. For a food intake event, the event information may include, for example, any of the information specified above with reference to task 2808 of the process 2800 (see FIG. 28 and the related description). The event information can be arranged, formatted, and expressed in an appropriate manner for purposes of controlling the adjustment of operating parameter(s) of the sensor system, to initiate the adjustment or regulation of such operating parameter(s), or the like. In practice, therefore, the event information is formatted and communicated in a way that is compatible with the sensor system. In certain embodiments, the event information can also be arranged, formatted, and expressed in an appropriate manner for purposes of controlling the adjustment of medication dosage and/or medication dispensing parameters of the system, as explained in more detail above.

This description assumes that at least one component of the sensor system receives and processes the event information (task 3208). More specifically, the received event information is processed to initiate the adjustment of one or more operating parameters of the sensor system. Thus, at least one operating parameter of the measurement sensor 2701 and/or at least one operating parameter of the measurement sensor processor 2702 can be adjusted in accordance with the provided event information. In this regard, task 3208 may be associated with one or more of the following, without limitation: changing an amount of power supplied to the measurement sensor and/or the measurement sensor processor; altering a measurement sampling rate of the measurement sensor; modifying the timing of output generated by the measurement sensor processor; varying a performance mode of the measurement sensor and/or the measurement sensor processor. Other adjustments can also be made, as appropriate for the particular embodiment (see, for example, FIG. 27 and the foregoing description of the system 2700).

As mentioned above, the measurement sensor 2701 generates sensor data that indicates the measured physiological characteristic of the user, such as blood glucose. The measurement sensor processor 2702 generates corresponding sensor measurement information from the sensor data (task 3210). The sensor data and/or the sensor measurement information is generated, processed, and/or communicated in a manner that is influenced by the provided event information (because the event information initiates the adjustment of one or more operating parameters of the sensor system).

The process 3200 may continue by controlling, adjusting, or regulating the medication dosage and/or the medication dispensing parameters in response to the sensor measurement information (task 3212). In certain embodiments, task 3212 controls, adjusts, or regulates the medication dosage and/or the medication dispensing parameters in response to the detected occurrence of the gesture-based physical behavior event, as indicated by the event information. For a detected food intake event, task 3212 can calculate the dosage of insulin to be delivered to the user and manage the dispensing of the insulin dose. The medication dosage and/or the medication dispensing parameters can be controlled, adjusted, or regulated using any of the techniques or methodologies described previously. For example, the medication dosage and/or dispensing parameters can be adjusted based on the current sensor values, predicted levels of the measured characteristic, the type of gesture(s) detected, confidence levels associated with detected gesture(s), bite count, sip count, current or historical ancillary (external) information, or the like.

EXAMPLES

Example 1

An automated medication dosing and dispensing system comprising: sensors to detect movement and other physical inputs related to a user of the automated medication dosing and dispensing system; a computer-readable storage medium comprising program code instructions; and a processor, wherein the program code instructions are configurable to cause the processor to perform a method comprising the steps of: determining, from sensor readings obtained from the sensors, occurrence of a gesture-based physical behavior event of the user; and adjusting medication dosage, medication dispensing parameters, or both medication dosage and medication dispensing parameters in response to the determining.

Example 2

The system of Example 1, wherein at least one of the sensor readings measures a movement of a body part of the user.

Example 3

The system of Example 1, further comprising an event detection module to determine, from the sensor readings, gestures of the user.

Example 4

The system of Example 1, wherein the method further comprises the step of sending a message to the user, wherein the message relates to the adjusting.

Example 5

The system of Example 1, wherein the gesture-based physical behavior event corresponds to user activity that is unrelated to a food intake event.

Example 6

The system of Example 5, wherein the user activity that is unrelated to the food intake event comprises a smoking event, a personal hygiene event, and/or a medication related event.

Example 7

The system of Example 1, wherein the gesture-based physical behavior event corresponds to a food intake event.

Example 8

The system of Example 1, wherein the adjusting is performed upon detection of an actual, probable, or imminent start of the gesture-based physical behavior event.

Example 9

The system of Example 1, wherein the adjusting is based on characteristics of the gesture-based physical behavior event.

Example 10

The system of Example 9, wherein: the gesture-based physical behavior event corresponds to a food intake event; and the adjusting is based on at least one of the following characteristics of the food intake event: time duration; pace; start time; end time; number of bites; number of sips; eating method; type of utensils used; type of containers used; amount of chewing before swallowing; chewing speed; amount of food consumed; amount of carbohydrates consumed, time between bites; time between sips; content of food consumed.

Example 11

The system of Example 1, wherein: the medication managed by the system is insulin; and the adjusting step calculates a dosage of insulin to be administered and a schedule for delivery of the calculated dosage of insulin.

Example 12

The system of Example 1, wherein the sensors comprise an accelerometer that measures movement of an arm of the user and a gyroscope that measures rotation of the arm of the user.

Example 13

A method of operating an automated medication dosing and dispensing system having sensors to detect movement and other physical inputs related to a user, the method comprising the steps of: obtaining, using a processor of the automated medication dosing and dispensing system, a set of sensor readings, wherein at least one sensor reading of the set of sensor readings measures a movement of a body part of a user; determining, from the set of sensor readings, occurrence of a gesture-based physical behavior event of the user; and adjusting medication dosage, medication dispensing parameters, or both medication dosage and medication dispensing parameters in response to the determining.

Example 14

The method of Example 13, further comprising the step of performing a computer-based action in response to the determining, wherein the computer-based action is one or more of: obtaining other information to be stored in memory in association with data representing the gesture-based physical behavior event; interacting with the user to provide information or a reminder; interacting with the user to prompt for user input; sending a message to a remote computer system; sending a message to another person; sending a message to the user.

Example 15

The method of Example 13, wherein the gesture-based physical behavior event corresponds to user activity that is unrelated to a food intake event.

Example 16

The method of Example 15, wherein the user activity that is unrelated to the food intake event comprises a smoking event, a personal hygiene event, and/or a medication related event.

Example 17

The method of Example 13, wherein the gesture-based physical behavior event corresponds to a food intake event.

Example 18

The method of Example 13, wherein the adjusting is performed upon detection of an actual, probable, or imminent start of the gesture-based physical behavior event.

Example 19

The method of Example 13, wherein the adjusting is based on characteristics of the gesture-based physical behavior event.

Example 20

The method of Example 19, wherein: the gesture-based physical behavior event corresponds to a food intake event; and the adjusting is based on at least one of the following characteristics of the food intake event: time duration; pace; start time; end time; number of bites; number of sips; eating method; type of utensils used; type of containers used; amount of chewing before swallowing; chewing speed; amount of food consumed; time between bites; time between sips; content of food consumed.

Example 21

An automated medication dosing and dispensing system comprising: sensors to detect movement related to a user of the automated medication dosing and dispensing system; a computer-readable storage medium comprising program code instructions; and a processor, wherein the program code instructions are configurable to cause the processor to perform a method comprising the steps of: determining, from sensor readings obtained from the sensors, a start or an anticipated start of a current food intake event of the user; reviewing historical data collected for previously recorded food intake events of the user; identifying a correlation between the current food intake event and a number of the previously recorded food intake events; and adjusting medication dosage, medication dispensing parameters, or both medication dosage and medication dispensing parameters based on the identified correlation.

Example 22

The system of Example 21, wherein at least one of the sensor readings measures a movement of a body part of the user.

Example 23

The system of Example 21, further comprising an event detection module to determine, from the sensor readings, a physical behavior event of the user.

Example 24

The system of Example 23, wherein the event detection module determines gestures of the user that characterize the current food intake event.

Example 25

The system of Example 21, wherein the adjusting is based on at least one of the following characteristics of the food intake event: time duration; pace; start time; end time; number of bites; number of sips; eating method; type of utensils used; type of containers used; amount of chewing before swallowing; chewing speed; amount of food consumed; time between bites; time between sips; content of food consumed.

Example 26

The system of Example 21, wherein: the medication managed by the system is insulin; and the adjusting step calculates a dosage of insulin to be administered and a schedule for delivery of the calculated dosage of insulin.

Example 27

The system of Example 21, wherein the sensors comprise an accelerometer that measures movement of an arm of the user and a gyroscope that measures rotation of the arm of the user.

Example 28

The system of Example 21, wherein the historical data comprises parameters that are not directly linked to the food intake event.

Example 29

The system of Example 28, wherein the parameters include at least one of: location information; time of day the user wakes up; stress level; sleeping behavior patterns; calendar event details; phone call information; email metadata.

Example 30

A method of operating an automated medication dosing and dispensing system having sensors to detect movement related to a user, the method comprising the steps of: determining, from sensor readings obtained from the sensors, a start or an anticipated start of a current food intake event of the user; reviewing historical data collected for previously recorded food intake events of the user; identifying a correlation between the current food intake event and a number of the previously recorded food intake events; and adjusting medication dosage, medication dispensing parameters, or both medication dosage and medication dispensing parameters based on the identified correlation.

Example 31

The method of Example 30, wherein at least one of the sensor readings measures a movement of a body part of the user.

Example 32

The method of Example 30, further comprising the step of determining, from the sensor readings, physical behavior events of the user.

Example 33

The method of Example 32, wherein the physical behavior events determined from the sensor readings include gestures of the user that characterize the current food intake event.

Example 34

The method of Example 30, wherein the adjusting is based on at least one of the following characteristics of the food intake event: time duration; pace; start time; end time; number of bites; number of sips; eating method; type of utensils used; type of containers used; amount of chewing before swallowing; chewing speed; amount of food consumed; time between bites; time between sips; content of food consumed.

Example 35

The method of Example 30, wherein: the medication managed by the system is insulin; and the adjusting step calculates a dosage of insulin to be administered and a schedule for delivery of the calculated dosage of insulin.

Example 36

The method of Example 30, wherein the sensors comprise an accelerometer that measures movement of an arm of the user and a gyroscope that measures rotation of the arm of the user.

Example 37

The method of Example 30 wherein the historical data comprises parameters that are not directly linked to the food intake event.

Example 38

The method of Example 37, wherein the parameters include at least one of: location information; time of day the user wakes up; stress level; sleeping behavior patterns; calendar event details; phone call information; email metadata.

Example 39

The method of Example 30, wherein the adjusting is performed upon detection of an actual or imminent start of the current food intake event.

Example 40

The method of Example 30, wherein the adjusting is based on characteristics of the current gesture-based physical behavior event.

Example 41

An automated medication dosing and dispensing system comprising: sensors to detect physical movement of a user of the automated medication dosing and dispensing system; computer-readable storage media comprising program code instructions; and at least one processor, wherein the program code instructions are configurable to cause the at least one device to perform a method comprising the steps of: detecting, based on analysis of sensor readings obtained from the sensors, occurrences of gesture-based physical behavior events; storing historical event information corresponding to the detected occurrences of gesture-based physical behavior events; processing the stored historical event information to predict a future occurrence of a physical behavior event of interest; and adjusting medication dosage, medication dispensing parameters, or both medication dosage and medication dispensing parameters in response to the predicted future occurrence of the physical behavior event of interest.

Example 42

The system of Example 41, wherein the processing step comprises processing the stored historical event information and at least one ancillary input received from a detection system that is distinct from the sensors.

Example 43

The system of Example 41, wherein the processing step comprises processing the stored historical event information and current sensor readings obtained from the sensors in real-time, including comparing the current sensor readings to the stored historical event information.

Example 44

The system of Example 41, wherein at least one of the sensor readings measures a movement of a specific body part of the user.

Example 45

The system of Example 41, wherein the method performed by the at least one processor further comprises the step of sending a message to the user, wherein the message relates to the predicted future occurrence of the physical behavior event of interest.

Example 46

The system of Example 41, wherein: the detected occurrences of gesture-based physical behavior events correspond to food intake events; and the adjusting is performed in response to a predicted food intake event.

Example 47

The system of Example 41, wherein: the medication managed by the system is insulin; and the adjusting step calculates a dosage of insulin to be administered.

Example 48

The system of Example 41, wherein: the method performed by the at least one processor further comprises the step of calculating a confidence level for the predicted future occurrence of the physical behavior event of interest; and the adjusting is performed in response to the confidence level.

Example 49

A method of operating an automated medication dosing and dispensing system having sensors that detect movement of a user, the method comprising the steps of: obtaining sensor readings from the sensors; detecting, based on analysis of the obtained sensor readings, occurrences of gesture-based physical behavior events; storing historical event information corresponding to the detected occurrences of gesture-based physical behavior events; processing, with at least one processor of the automated medication dosing and dispensing system, the stored historical event information to predict a future occurrence of a physical behavior event of interest; and adjusting medication dosage, medication dispensing parameters, or both medication dosage and medication dispensing parameters in response to the predicted future occurrence of the physical behavior event of interest.

Example 50

The method of Example 49, wherein the processing step comprises processing the stored historical event information and at least one ancillary input received from a detection system that is distinct from the sensors.

Example 51

The method of Example 50, wherein: the detected occurrences of gesture-based physical behavior events correspond to food intake events; and the at least one ancillary input comprises information that is not directly related to food intake events.

Example 52

The method of Example 49, wherein at least one of the sensor readings measures a movement of a specific body part of the user.

Example 53

The method of Example 49, further comprising the step of sending a message to the user, wherein the message relates to the predicted future occurrence of the physical behavior event of interest.

Example 54

The method of claim 49, wherein: the detected occurrences of gesture-based physical behavior events correspond to food intake events; and the adjusting is performed in response to a predicted food intake event.

Example 55

The method of Example 49, wherein: the medication managed by the system is insulin; and the adjusting step calculates a dosage of insulin to be administered.

Example 56

The method of Example 49, further comprising the step of calculating a confidence level for the predicted future occurrence of the physical behavior event of interest, wherein the adjusting is performed in response to the confidence level.

Example 57

A method of operating an automated medication dosing and dispensing system having sensors that detect movement, the method comprising the steps of: obtaining sensor readings from the sensors, the sensor readings indicating movement of at least one body part of the user; detecting, based on analysis of the obtained sensor readings, occurrences of gesture-based physical behavior events; storing historical event information corresponding to the detected occurrences of gesture-based physical behavior events; receiving at least one ancillary input from a detection system that is distinct from the sensors; processing, with at least one processor of the automated medication dosing and dispensing system, the stored historical event information and the at least one ancillary input to predict a future occurrence of a physical behavior event of interest; and adjusting medication dosage, medication dispensing parameters, or both medication dosage and medication dispensing parameters in response to the predicted future occurrence of the physical behavior event of interest.

Example 58

The method of Example 57, wherein: the detected occurrences of gesture-based physical behavior events correspond to food intake events; the at least one ancillary input comprises information that is not directly related to food intake events; and the adjusting is performed in response to a predicted food intake event.

Example 59

The method of Example 57, further comprising the step of calculating a confidence level for the predicted future occurrence of the physical behavior event of interest, wherein the adjusting is performed in response to the confidence level.

Example 60

The method of Example 57, wherein the processing step predicts the future occurrence of the physical behavior event of interest based on characteristics of a currently detected gesture-based physical behavior event.

Example 61

An automated medication dosing and dispensing system comprising: gesture sensors to detect physical movement of a user of the automated medication dosing and dispensing system; computer-readable storage media comprising program code instructions; and at least one processor, wherein the program code instructions are configurable to cause the at least one processor to perform a method comprising the steps of: detecting, based on analysis of gesture sensor readings obtained from the gesture sensors, an occurrence of a gesture-based physical behavior event; calculating an initial confidence level for the detected occurrence of the gesture-based physical behavior event; deriving a final confidence level, for the detected occurrence of the gesture-based physical behavior event, from the initial confidence level and from external information obtained from at least one source of data that is distinct from the gesture sensors; and adjusting medication dosage, medication dispensing parameters, or both medication dosage and medication dispensing parameters in response to the detected occurrence of the gesture-based physical behavior event and the final confidence level.

Example 62

The system of Example 61, wherein: the at least one source of data comprises an ancillary event detection system that is physically distinct from the gesture sensors; the ancillary event detection system comprises at least one component to generate user status information that is not directly related to user gestures; and the external information comprises the user status information.

Example 63

The system of Example 61, wherein: the at least one source of data comprises a measurement sensor that generates sensor data indicative of a physiological characteristic of the user; the external information comprises the sensor data; and the medication dosage or the medication dispensing parameters are determined based on the sensor data.

Example 64

The system of Example 63, wherein the measurement sensor comprises a continuous glucose monitor.

Example 65

The system of Example 61, wherein: the at least one source of data comprises a prediction system to predict future occurrences of gesture-based physical behavior events; and the external information comprises predictive information generated by the prediction system, the predictive information describing, characterizing, or defining a predicted future occurrence of a gesture-based physical behavior event.

Example 66

The system of Example 61, wherein: the detected occurrence of the gesture-based physical behavior event corresponds to a food intake event; the medication managed by the system is insulin; and the adjusting step calculates a dosage of insulin to be administered.

Example 67

A method of operating an automated medication dosing and dispensing system having gesture sensors that detect physical movement of a user, the method comprising the steps of: obtaining gesture sensor readings from the gesture sensors; detecting, based on analysis of the obtained gesture sensor readings, an occurrence of a gesture-based physical behavior event; calculating an initial confidence level for the detected occurrence of the gesture-based physical behavior event; deriving a final confidence level, for the detected occurrence of the gesture-based physical behavior event, from the initial confidence level and external information obtained from at least one source of data that is distinct from the gesture sensors; and adjusting medication dosage, medication dispensing parameters, or both medication dosage and medication dispensing parameters in response to the detected occurrence of the gesture-based physical behavior event and the final confidence level.

Example 68

The method of Example 67, wherein: the at least one source of data comprises an ancillary event detection system that is physically distinct from the gesture sensors; the ancillary event detection system comprises at least one component to generate user status information that is not directly related to user gestures; and the external information comprises the user status information.

Example 69

The method of Example 67, wherein: the at least one source of data comprises a measurement sensor that generates sensor data indicative of a physiological characteristic of the user; and the external information comprises the sensor data.

Example 70

The method of Example 67, wherein: the at least one source of data comprises a prediction system to predict future occurrences of gesture-based physical behavior events; and the external information comprises predictive information generated by the prediction system, the predictive information describing, characterizing, or defining a predicted future occurrence of a gesture-based physical behavior event.

Example 71

An automated medication dosing and dispensing system comprising: gesture sensors to detect physical movement of a user of the automated medication dosing and dispensing system; computer-readable storage media comprising program code instructions; and at least one processor, wherein the program code instructions are configurable to cause the at least one processor to perform a method comprising the steps of: maintaining default event declaration criteria for use in determining whether a gesture-based physical behavior event of interest has occurred or is likely to occur; obtaining gesture sensor readings from the gesture sensors; deriving final event declaration criteria, for use in determining whether the gesture-based physical behavior event of interest has occurred or is likely to occur, from the default event declaration criteria and from external information obtained from at least one source of data that is distinct from the gesture sensors; analyzing the obtained gesture sensor readings to determine whether the final event declaration criteria is satisfied; when the obtained gesture sensor readings satisfy the final event declaration criteria, declaring a detection of the gesture-based physical behavior event of interest; and adjusting medication dosage, medication dispensing parameters, or both medication dosage and medication dispensing parameters in response to the declaring.

Example 72

The system of Example 71, wherein the deriving step decreases requirements of the default event declaration criteria when the external information indicates with high confidence that the gesture-based physical behavior event of interest has occurred, increases requirements of the default event declaration criteria when the external information indicates with low confidence that the gesture-based physical behavior event of interest has occurred, or preserves the default event declaration criteria when the external information is insufficient to influence the default event declaration criteria.

Example 73

The system of Example 71, wherein: the at least one source of data comprises an ancillary event detection system that is physically distinct from the gesture sensors; the ancillary event detection system comprises at least one component to generate user status information that is not directly related to user gestures; and the external information comprises the user status information.

Example 74

The system of Example 71, wherein: the at least one source of data comprises a measurement sensor that generates sensor data indicative of a physiological characteristic of the user; and the external information comprises the sensor data.

Example 75

The system of Example 74, wherein the measurement sensor comprises a continuous glucose monitor.

Example 76

The system of Example 71, wherein: the at least one source of data comprises a prediction system to predict future occurrences of gesture-based physical behavior events; and the external information comprises predictive information generated by the prediction system, the predictive information describing, characterizing, or defining a predicted occurrence of a gesture-based physical behavior event.

Example 77

The system of Example 71, wherein: the gesture-based physical behavior event of interest corresponds to a food intake event; the medication managed by the system is insulin; and the adjusting step calculates a dosage of insulin to be administered.

Example 78

A method of operating an automated medication dosing and dispensing system having gesture sensors that detect physical movement of a user, the method comprising the steps of: maintaining default event declaration criteria for use in determining whether a gesture-based physical behavior event of interest has occurred or is likely to occur; obtaining gesture sensor readings from the gesture sensors; deriving final event declaration criteria, for use in determining whether the gesture-based physical behavior event of interest has occurred or is likely to occur, from the default event declaration criteria and from external information obtained from at least one source of data that is distinct from the gesture sensors; analyzing the obtained gesture sensor readings to determine whether the final event declaration criteria is satisfied; when the obtained gesture sensor readings satisfy the final event declaration criteria, declaring a detection of the gesture-based physical behavior event of interest; and adjusting medication dosage, medication dispensing parameters, or both medication dosage and medication dispensing parameters in response to the declaring.

Example 79

The method of Example 78, wherein the deriving step decreases requirements of the default event declaration criteria when the external information indicates with high confidence that the gesture-based physical behavior event of interest has occurred, increases requirements of the default event declaration criteria when the external information indicates with low confidence that the gesture-based physical behavior event of interest has occurred, or preserves the default event declaration criteria when the external information is insufficient to influence the default event declaration criteria.

Example 80

The method of Example 78, wherein: the gesture-based physical behavior event of interest corresponds to a food intake event; the medication managed by the system is insulin; and the adjusting step calculates a dosage of insulin to be administered.

Example 81

An automated medication dosing and dispensing system comprising: gesture sensors to detect physical movement of a user of the automated medication dosing and dispensing system; a measurement sensor to generate sensor data indicative of a physiological characteristic of the user; a measurement sensor processor to process the sensor data generated by the measurement sensor; computer-readable storage media comprising program code instructions; and at least one processor, wherein the program code instructions are configurable to cause the at least one processor to perform a method comprising the steps of: detecting, based on analysis of gesture sensor readings obtained from the gesture sensors, an occurrence of a gesture-based physical behavior event; providing, to at least one of the measurement sensor and the measurement sensor processor, event information corresponding to the detected occurrence of the gesture-based physical behavior event; and adjusting an operating parameter of the at least one of the measurement sensor and the measurement sensor processor, in accordance with the provided event information.

Example 82

The system of Example 81, wherein the method performed by the at least one processor further comprises the step of: regulating medication dosage, medication dispensing parameters, or both medication dosage and medication dispensing parameters in response to the detected occurrence of the gesture-based physical behavior event.

Example 83

The system of Example 81, wherein the method performed by the at least one processor further comprises the steps of: generating, by the measurement sensor processor, sensor measurement information from the sensor data; and regulating medication dosage, medication dispensing parameters, or both medication dosage and medication dispensing parameters in response to the sensor measurement information.

Example 84

The system of Example 83, wherein the regulating step adjusts the medication dosage, the medication dispensing parameters, or both the medication dosage and the medication dispensing parameters in response to the detected occurrence of the gesture-based physical behavior event.

Example 85

The system of Example 83, wherein: the detected occurrence of the gesture-based physical behavior event corresponds to a food intake event; the system manages dosing and dispensing of insulin; and the regulating step calculates a dosage of insulin to be administered.

Example 86

The system of Example 81, wherein the measurement sensor comprises a continuous glucose monitor.

Example 87

The system of Example 81, wherein the provided event information comprises data that describes, characterizes, or defines a food intake event.

Example 88

The system of Example 81, wherein the adjusting step comprises: changing an amount of power supplied to the at least one of the measurement sensor and the measurement sensor processor; altering a measurement sampling rate of the measurement sensor; modifying timing of output generated by the measurement sensor processor; or varying a performance mode of at least one of the measurement sensor and the measurement sensor processor.

Example 89

A method of operating an automated medication dosing and dispensing system comprising gesture sensors to detect physical movement of a user, a measurement sensor to generate sensor data indicative of a physiological characteristic of the user, and a measurement sensor processor to process the sensor data, the method comprising the steps of: obtaining gesture sensor readings from the gesture sensors; detecting, based on analysis of the obtained gesture sensor readings, an occurrence of a gesture-based physical behavior event; providing, to at least one of the measurement sensor and the measurement sensor processor, event information corresponding to the detected occurrence of the gesture-based physical behavior event, the event information formatted to control adjustment of an operating parameter of the at least one of the measurement sensor and the measurement sensor processor, in accordance with the provided event information.

Example 90

The method of Example 89, wherein the provided event information is formatted to control adjustment of medication dosage, medication dispensing parameters, or both medication dosage and medication dispensing parameters of the system.

Example 91

The method of Example 90, wherein: the detected occurrence of the gesture-based physical behavior event corresponds to a food intake event; the system manages dosing and dispensing of insulin; and the provided event information influences calculation of a dosage of insulin to be administered.

Example 92

The method of Example 89, wherein the provided event information comprises data that describes, characterizes, or defines a food intake event.

Example 93

The method of Example 89, further comprising the step of adjusting the operating parameter, wherein the adjusting step comprises: changing an amount of power supplied to the at least one of the measurement sensor and the measurement sensor processor; altering a measurement sampling rate of the measurement sensor; modifying timing of output generated by the measurement sensor processor; or varying a performance mode of at least one of the measurement sensor and the measurement sensor processor.

Example 94

A method of operating an automated medication dosing and dispensing system comprising gesture sensors to detect physical movement of a user, a measurement sensor to generate sensor data indicative of a physiological characteristic of the user, and a measurement sensor processor to process the sensor data, the method comprising the steps of: obtaining gesture sensor readings from the gesture sensors; detecting, based on analysis of the obtained gesture sensor readings, an occurrence of a gesture-based physical behavior event; providing, to at least one of the measurement sensor and the measurement sensor processor, event information corresponding to the detected occurrence of the gesture-based physical behavior event; and adjusting one or more operating parameters of at least one of the measurement sensor and the measurement sensor processor, in accordance with the provided event information.

Example 95

The method of Example 94, further comprising the step of: regulating medication dosage, medication dispensing parameters, or both medication dosage and medication dispensing parameters in response to the detected occurrence of the gesture-based physical behavior event.

Example 96

The method of Example 94, further comprising the steps of: generating, by the measurement sensor processor, sensor measurement information from the sensor data; and regulating medication dosage, medication dispensing parameters, or both medication dosage and medication dispensing parameters in response to the sensor measurement information.

Example 97

The method of Example 96, wherein the medication dosage or the medication dispensing parameters are determined based on the sensor measurement information.

Example 98

The method of Example 94, wherein: the detected occurrence of the gesture-based physical behavior event corresponds to a food intake event; the system manages dosing and dispensing of insulin; and the provided event information influences calculation of a dosage of insulin to be administered.

Example 99

The method of Example 94, wherein the provided event information comprises data that describes, characterizes, or defines a food intake event.

Example 100

The method of claim 94, wherein the adjusting step comprises: changing an amount of power supplied to the at least one of the measurement sensor and the measurement sensor processor; altering a measurement sampling rate of the measurement sensor; modifying timing of output generated by the measurement sensor processor; or varying a performance mode of at least one of the measurement sensor and the measurement sensor processor.

CONCLUSION

As described above, there are various methods and apparatus that can be used as part of a medication dispensing regimen and alternatives provided herein. Conjunctive language, such as phrases of the form "at least one of A, B, and C," or "at least one of A, B and C," unless specifically stated otherwise or otherwise clearly contradicted by context, is otherwise understood with the context as used in general to present that an item, term, etc., may be either A or B or C, or any nonempty subset of the set of A and B and C. For instance, in the illustrative example of a set having three members, the conjunctive phrases "at least one of A, B, and C" and "at least one of A, B and C" refer to any of the following sets: {A}, {B}, {C}, {A, B}, {A, C}, {B, C}, {A, B, C}. Thus, such conjunctive language is not generally intended to imply that certain embodiments require at least one of A, at least one of B and at least one of C each to be present.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

The various tasks performed in connection with an illustrated process may be performed by software, hardware, firmware, or any combination thereof, which may be implemented with any of the devices, systems, or components described herein. It should be appreciated that a described process may include any number of additional or alternative tasks, the tasks shown in a flow chart need not be performed in the illustrated order, and a described process may be incorporated into a more comprehensive procedure or process having additional functionality not described in detail herein. Moreover, one or more of the tasks shown in a flow chart could be omitted from an embodiment of the described process as long as the intended overall functionality remains intact.

The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Further embodiments can be envisioned to one of ordinary skill in the art after reading this disclosure. In other embodiments, combinations or sub-combinations of the above-disclosed invention can be advantageously made. The example arrangements of components are shown for purposes of illustration and it should be understood that combinations, additions, re-arrangements, and the like are contemplated in alternative embodiments of the present invention. Thus, while the invention has been described with respect to exemplary embodiments, one skilled in the art will recognize that numerous modifications are possible.

For example, the processes described herein may be implemented using hardware components, software components, and/or any combination thereof. The specification and drawings are, accordingly, to be regarded in an illustrative rather than a restrictive sense. It will, however, be evident that various modifications and changes may be made thereunto without departing from the broader spirit and scope of the invention as set forth in the claims and that the invention is intended to cover all modifications and equivalents within the scope of the following claims.

All references, including publications, patent applications, and patents, cited herein are hereby incorporated by reference to the same extent as if each reference were individually and specifically indicated to be incorporated by reference and were set forth in its entirety herein.

What is claimed is:

1. An automated medication dosing and dispensing system comprising:
    gesture sensors to detect physical movement of a user of the automated medication dosing and dispensing system;
    computer-readable storage media comprising program code instructions; and
    at least one processor, wherein the program code instructions are configurable to cause the at least one processor to perform a method comprising the steps of:
        detecting, based on analysis of gesture sensor readings obtained from the gesture sensors, an occurrence of a gesture-based physical behavior event;
        calculating an initial confidence level for the detected occurrence of the gesture-based physical behavior event, wherein the initial confidence level represents an initial probability that the occurrence of the gesture-based physical behavior event was correctly detected;
        deriving a final confidence level, for the detected occurrence of the gesture-based physical behavior event, from the initial confidence level and from external information obtained from at least one source of data that is distinct from the gesture sensors, wherein the final confidence level represents a final probability that the occurrence of the gesture-based physical behavior event was correctly detected; and
        adjusting medication dosage, medication dispensing parameters, or both medication dosage and medication dispensing parameters of the automated medication dosing and dispensing system in response to the detected occurrence of the gesture-based physical behavior event and the final confidence level.

2. The system of claim 1, wherein:
    the at least one source of data comprises an ancillary event detection system that is physically distinct from the gesture sensors;
    the ancillary event detection system comprises at least one component to generate user status information that is not directly related to user gestures; and
    the external information comprises the user status information.

3. The system of claim 1, wherein:
    the at least one source of data comprises a measurement sensor that generates sensor data indicative of a physiological characteristic of the user;
    the external information comprises the sensor data; and
    the medication dosage or the medication dispensing parameters are determined based on the sensor data.

4. The system of claim 3, wherein the measurement sensor comprises a continuous glucose monitor.

5. The system of claim 1, wherein:
    the at least one source of data comprises a prediction system to predict future occurrences of gesture-based physical behavior events; and
    the external information comprises predictive information generated by the prediction system, the predictive information describing, characterizing, or defining a predicted future occurrence of a gesture-based physical behavior event.

6. The system of claim 1, wherein:
    the detected occurrence of the gesture-based physical behavior event corresponds to a food intake event;
    the medication managed by the system is insulin; and
    the adjusting step calculates a dosage of insulin to be administered.

7. A method of operating an automated medication dosing and dispensing system having gesture sensors that detect physical movement of a user, the method comprising the steps of:
    obtaining gesture sensor readings from the gesture sensors;
    detecting, based on analysis of the obtained gesture sensor readings, an occurrence of a gesture-based physical behavior event;
    calculating an initial confidence level for the detected occurrence of the gesture-based physical behavior event, wherein the initial confidence level represents an initial probability that the occurrence of the gesture-based physical behavior event was correctly detected;
    deriving a final confidence level, for the detected occurrence of the gesture-based physical behavior event, from the initial confidence level and external information obtained from at least one source of data that is distinct from the gesture sensors, wherein the final confidence level represents a final probability that the occurrence of the gesture-based physical behavior event was correctly detected; and
    adjusting medication dosage, medication dispensing parameters, or both medication dosage and medication dispensing parameters of the automated medication dosing and dispensing system in response to the detected occurrence of the gesture-based physical behavior event and the final confidence level.

8. The method of claim 7, wherein:
    the at least one source of data comprises an ancillary event detection system that is physically distinct from the gesture sensors;
    the ancillary event detection system comprises at least one component to generate user status information that is not directly related to user gestures; and
    the external information comprises the user status information.

9. The method of claim 7, wherein:
    the at least one source of data comprises a measurement sensor that generates sensor data indicative of a physiological characteristic of the user; and
    the external information comprises the sensor data.

10. The method of claim 7, wherein:
    the at least one source of data comprises a prediction system to predict future occurrences of gesture-based physical behavior events; and
    the external information comprises predictive information generated by the prediction system, the predictive information describing, characterizing, or defining a predicted future occurrence of a gesture-based physical behavior event.

11. An automated medication dosing and dispensing system comprising:
    gesture sensors to detect physical movement of a user of the automated medication dosing and dispensing system;
    computer-readable storage media comprising program code instructions; and
    at least one processor, wherein the program code instructions are configurable to cause the at least one processor to perform a method comprising the steps of:
        maintaining default event declaration decision criteria for use in determining whether a gesture-based physical behavior event of interest has occurred or is likely to occur;
        obtaining gesture sensor readings from the gesture sensors;

deriving final event declaration decision criteria, for use in determining whether the gesture-based physical behavior event of interest has occurred or is likely to occur, from the default event declaration decision criteria and from external information obtained from at least one source of data that is distinct from the gesture sensors;

analyzing the obtained gesture sensor readings to determine whether the final event declaration decision criteria is satisfied;

when the obtained gesture sensor readings satisfy the final event declaration decision criteria, declaring a detection of the gesture-based physical behavior event of interest; and adjusting medication dosage, medication dispensing parameters, or both medication dosage and medication dispensing parameters in response to the declaring.

12. The system of claim 11, wherein the deriving step decreases requirements of the default event declaration decision criteria when the external information indicates with high confidence that the gesture-based physical behavior event of interest has occurred, increases requirements of the default event declaration decision criteria when the external information indicates with low confidence that the gesture-based physical behavior event of interest has occurred, or preserves the default event declaration decision criteria when the external information is insufficient to influence the default event declaration decision criteria.

13. The system of claim 11, wherein:
the at least one source of data comprises an ancillary event detection system that is physically distinct from the gesture sensors;
the ancillary event detection system comprises at least one component to generate user status information that is not directly related to user gestures; and
the external information comprises the user status information.

14. The system of claim 11, wherein:
the at least one source of data comprises a measurement sensor that generates sensor data indicative of a physiological characteristic of the user; and
the external information comprises the sensor data.

15. The system of claim 14, wherein the measurement sensor comprises a continuous glucose monitor.

16. The system of claim 11, wherein:
the at least one source of data comprises a prediction system to predict future occurrences of gesture-based physical behavior events; and
the external information comprises predictive information generated by the prediction system, the predictive information describing, characterizing, or defining a predicted occurrence of a gesture-based physical behavior event.

17. The system of claim 11, wherein:
the gesture-based physical behavior event of interest corresponds to a food intake event;
the medication managed by the system is insulin; and
the adjusting step calculates a dosage of insulin to be administered.

18. A method of operating an automated medication dosing and dispensing system having gesture sensors that detect physical movement of a user, the method comprising the steps of:

maintaining default event declaration decision criteria for use in determining whether a gesture-based physical behavior event of interest has occurred or is likely to occur;

obtaining gesture sensor readings from the gesture sensors;

deriving final event declaration decision criteria, for use in determining whether the gesture-based physical behavior event of interest has occurred or is likely to occur, from the default event declaration decision criteria and from external information obtained from at least one source of data that is distinct from the gesture sensors;

analyzing the obtained gesture sensor readings to determine whether the final event declaration decision criteria is satisfied;

when the obtained gesture sensor readings satisfy the final event declaration decision criteria, declaring a detection of the gesture-based physical behavior event of interest; and adjusting medication dosage, medication dispensing parameters, or both medication dosage and medication dispensing parameters in response to the declaring.

19. The method of claim 18, wherein the deriving step decreases requirements of the default event declaration decision criteria when the external information indicates with high confidence that the gesture-based physical behavior event of interest has occurred, increases requirements of the default event declaration decision criteria when the external information indicates with low confidence that the gesture-based physical behavior event of interest has occurred, or preserves the default event declaration decision criteria when the external information is insufficient to influence the default event declaration decision criteria.

20. The method of claim 18, wherein:
the gesture-based physical behavior event of interest corresponds to a food intake event;
the medication managed by the system is insulin; and
the adjusting step calculates a dosage of insulin to be administered.

* * * * *